(12) United States Patent
Miller et al.

(10) Patent No.: US 9,526,721 B2
(45) Date of Patent: Dec. 27, 2016

(54) TETRAHYDROPROTOBERBINE COMPOUNDS AND USES THEREOF IN THE TREATMENT OF NEUROLOGICAL, PSYCHIATRIC AND NEURODEGENERATIVE DISEASES

(76) Inventors: James Jackson Miller, Vancouver (CA); Anthony George Phillips, Vancouver (CA); Christopher Court Lapish, Indianapolis, IN (US); Glenn Martin Sammis, Vancouver (CA)

( * ) Notice: Subject to any disclaimer, the term of this patent is extended or adjusted under 35 U.S.C. 154(b) by 0 days.

(21) Appl. No.: 14/418,921

(22) PCT Filed: Aug. 2, 2012

(86) PCT No.: PCT/CA2012/050526
§ 371 (c)(1),
(2), (4) Date: Jun. 8, 2015

(87) PCT Pub. No.: WO2013/020229
PCT Pub. Date: Feb. 14, 2013

(65) Prior Publication Data
US 2015/0306092 A1    Oct. 29, 2015

(51) Int. Cl.
*A61K 31/4745* (2006.01)
*A61K 45/06* (2006.01)
*C07D 471/04* (2006.01)

(52) U.S. Cl.
CPC ........... *A61K 31/4745* (2013.01); *A61K 45/06* (2013.01); *C07D 471/04* (2013.01)

(58) Field of Classification Search
CPC .... A61K 31/4745; A61K 45/06; C07D 471/04
USPC ........................................................ 514/287
See application file for complete search history.

(56) References Cited

FOREIGN PATENT DOCUMENTS

WO    WO2008014661 A1 * 2/2008 ........... C07D 455/03

OTHER PUBLICATIONS

Lapish et al Int J Neuropsychopharmacol. 2012, 15(10) 1441-1455; Abstract.*
Machine translation of WO2008/014661A (2008).*

* cited by examiner

*Primary Examiner* — Yevegeny Valenrod
(74) *Attorney, Agent, or Firm* — Joseph R. Baker, Jr.; Gavrilovich, Dodd & Lindsey LLP

(57) ABSTRACT

Tetrahydroprotoberbine (THPB) compounds and their use in the treatment of neurological, psychiatric and neurodegenerative diseases is provided. The compounds include d-govadine, l-govadine and racemic govadine, as well as d-THPBs of general formula (I). Enantioselective processes for preparing compounds of formula (I), and d- and l-govadine are also provided.(I)

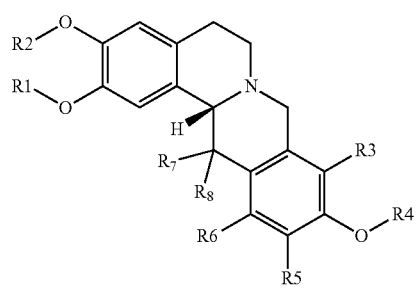

12 Claims, 15 Drawing Sheets

D.
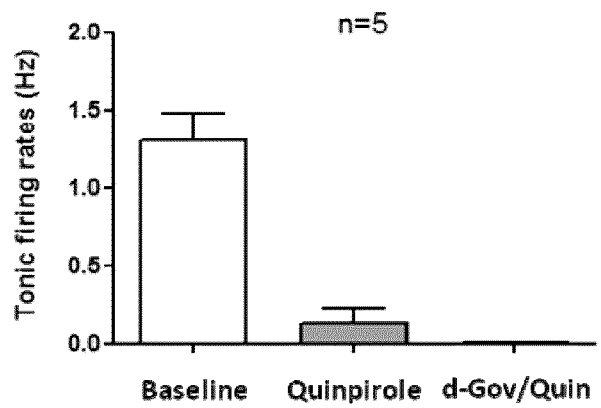
E.
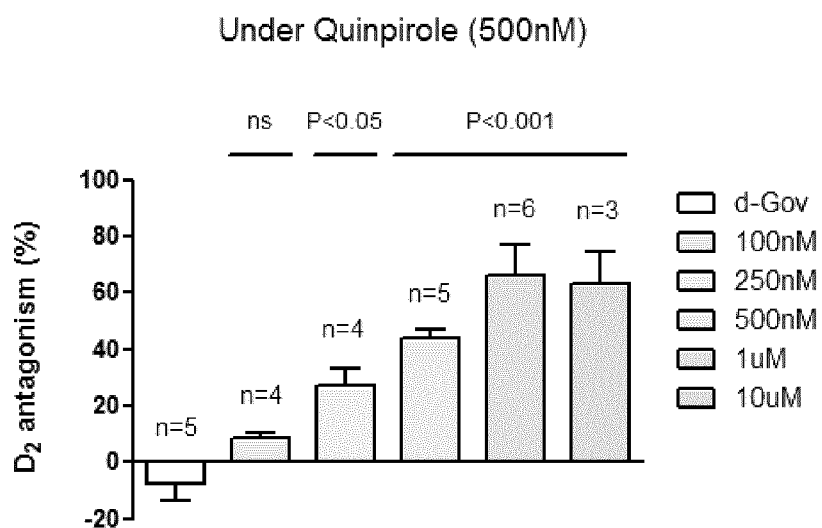
FIG. 11 (con.)

A.

B.

C.

TETRAHYDROPROTOBERBINE COMPOUNDS AND USES THEREOF IN THE TREATMENT OF NEUROLOGICAL, PSYCHIATRIC AND NEURODEGENERATIVE DISEASES

CROSS REFERENCE TO RELATED APPLICATIONS

This application is a U.S. National Stage Application filed under 35 U.S.C. §371 and claims priority to International Application No. PCT/CA2012/050526, filed Aug. 2, 2012, the disclosure of which is incorporated herein by reference in its entirety.

FIELD OF THE INVENTION

This invention pertains to the field of therapies for neurological, psychiatric and neurodegenerative diseases, in particular, to therapeutically active tetrahydroprotoberbine compounds, including stereochemically pure compounds, and their use in the treatment of such diseases.

BACKGROUND OF THE INVENTION

Dysfunction of the brain ascending dopaminergic system is responsible for a wide array of severe neuropsychiatric conditions, affecting millions of people in North America and Europe. Schizophrenia, for example, is a chronic and debilitating neurological disorder that is characterized by the presentation of positive symptoms, negative symptoms and cognitive impairments. It is believed that an imbalance in the dopaminergic system (subcortical excess and cortical deficiency) is involved in the pathophysiological processes of schizophrenia (see, for example, Abi-Dargham, A., 2004, *Int. J. Neuropsychopharmacol.*, 7 Suppl. 1:S1-S5). It is believed that decreased activity of the $D_1$ receptors in the PFC may play a significant role in the expression of negative symptoms and cognitive deficits in schizophrenic patients. However, almost all currently available antipsychotic drugs are $D_2$ dopamine receptor antagonist with some extent of serotonergic activities. As such, these antipsychotic drugs are only moderately effective in treating the positive symptoms of schizophrenia and are not effective in treating the negative symptoms and cognitive deficits in these patients.

Cognitive impairment mediated by hypoactivity in the prefronal cortex (PFC) is commonly observed in schizophrenic individuals (Goldman-Rakic, 1999, *Biol Psych* 46(5):650-661; Weinberger et al., 2001, *Biol Psych* 50(11): 825-844; Seamans and Yang, 2004, *Prog in Neurobiol* 74(1):1-58). Clinical data suggest a beneficial relationship between improved cognition and positive social and clinical outcomes (Andreasen, 2000, *Brain Res Brain Res Rev* 31(2-3):106-112), but development of effective treatments to address cognitive deficits seen in psychotic patients has been challenging. Preclinical studies provide strong support for the hypothesis that optimal dopamine concentrations in the frontal lobes facilitate cognitive function (Goldman-Rakic, 1995, *Neuron* 14(3):477-485; Phillips et al., 2004, *J Neurosci*, 24(2):547-553). Increasing the bioavailability of dopamine or local stimulation of dopamine receptors in the frontal cortex is effective in animals to improve cognitive function in circumstances where cognitive performance is suboptimal (Fletcher et al., 1996, *J Neurosci* 16(21):7055-7062; Hotte et al., 2005, *Neurobiol Learn Mem* 84(2):85-92; Floresco & Phillips, 2001, *Behav Neurosci* 204(2):396-409; Tunbridge et al., 2004, *J Neurosci* 24(23):5331-5335; Lap-ish et al., 2009, *Psychopharm* 202(1-3):521-530). Accordingly, pharmacotherapies that restore optimal PFC dopamine levels or activity at PFC dopamine receptors, may yield an effective pro-cognitive treatment strategy.

Tetrahydroprotoberberines (THPBs) are a series of alkaloids isolated from plants. Chemically, the compound l-stepholidine (also known as (−)-stepholidine or (S)-stepholidine), which is isolated from roots of the Chinese herb *Stephania intermedica lo*, is a prototypical member of the THPBs characterized by a tetracyclic ring skeleton, an isoquinoline core, and a chiral carbon at C(14) (see FIG. 1). l-stepholidine (l-SPD) appears to exhibit unique pharmacological activities in its ability to elicit activities in both the $D_1$ and $D_2$ receptors in vitro and in vivo (Gao et al., 2007, *Acta Pharmacol Sin.*, 28(5):627-33; Jin et al., 2002, *Trends Pharmacol Sci.*, 23(1):4-7; Mo et al., 2007, *Curr Med Chem.*, 14(28):2996-3002; Mo et al., 2008, *Neurobiol Aging*, August 14, [Epub ahead of print]). Synthesis of racemic dl-SPD and enantioselective synthesis of l-SPD have been reported (Chiang & Brochmann-Hanssen, 1977, *J Org Chem.*, 42:3190-3194; Cheng et al., 2009, *J Org Chem.*, 74(23):9225-8).

l-govadine is another example of a THPB that has been isolated from natural sources (Hu et al., 1998, *Zhongguo Yaowu Huaxue Zazhi*, 8:190-195). The synthesis of racemic govadine has been reported (Hu et al., 1998, ibid, Kametani & Satoh, 1967, *J. Pharm. Soc. Jpn*, 179; Chiang & Brochmann-Hanssen, 1977, ibid.; Chiang, et al., 1978, *Taiwan Yaoxue Zazhi*, 54:30; Kametani & Ihara, 1980, *J. Chem. Soc., Perkin Trans.* 1, 629; Yongzhou, 1998, *Chinese J. Med. Chem.*, 8:190; Mehra, et al., 1976, *Indian J. Chem., Sect B*, 14B:216). These routes access the desired tetrahydroisoquinoline core utilizing racemic reductions of the corresponding dihydroisoquinoline.

Investigations into the activity of certain THPBs has suggested that the l- and d-enantiomers of the compounds may possess different activities. Clement-Cormier et al. (1979, *Biochemical Pharmacology*, 28:3123-3129) reported that optical isomers of 2,3,10,11-THPB showed different activities in the antagonism of the dopamine-sensitive adenylate cyclase, as did positional isomers and methylated derivatives.

Jin et al. (1984, *Scientia Sinica*, 29:1054-1064) investigated the activities of l- and d-tetrahydropalmitine (THP) on the dopaminergic system. The results obtained in this study indicated that d-THP had no affinity for the dopamine receptors and demonstrated different effects on DOPA accumulation and dopamine levels than the l-isomer, leading the authors to conclude that l-THP is a dopamine receptor antagonist, whereas d-THP is a dopamine depletor. Similarly, Shou-Xi et al. (1989, *Acta Pharmalogica Sinica*, 10:104-110) compared the affinity of l- and d-THP for the dopamine $D_1$ and $D_2$ receptors and concluded that d-THP has no affinity for the $D_2$ receptor. Later functional studies on l- and d-THP led to the same conclusion (Sun et al., 1992, *Acta Pharmalogica Sinica*, 13:292-297; Cao et al., 1993, *Asia Pacific J Pharmacology*, 8:61-65).

Zhang and Jin (1996, *Acta Pharmalogica Sinica*, 17:18-22) compared the effects of (−)-SPD (l-SPD) with chloroscoulerine (CSL) enantiomers on the dopamine $D_1$ and $D_2$ receptors and concluded that CSL enantiomers, like l-SPD, are $D_1/D_2$ mixed antagonists, and that while all the compounds tested were $D_2$ antagonists, (+)-CSL was a very weak one. Chen et al. (1999, *Acta Pharmalogica Sinica*, 20:884-888) investigated the pharmacological behaviour of CSL enantiomers on dopamine receptors, in particular the activity of CSL enantiomers in behavioural tests in mice and rats. The study determined that d-CSL had a weaker affinity for the $D_1$ receptor and a much weaker affinity for the $D_2$ receptor than l-CSL, and that while both enantiomers inhibited apomorphine-induced stereotypy, catalepsy and amphetamine-induced jumping in test animals, d-CSL showed a weaker effect in all tests.

l-SPD has been the subject of extensive preclinical research primarily motivated by its ability to dynamically target dopamine $D_1$ and $D_2$ receptors (Mo et al., 2007, *Current Medicinal Chemistry*, 14:2996-3002; Natesan et al., 2008, *Psychopharmacology*, 199:275-289). Preclinical measures of antipsychotic efficacy such as attenuated psychostimulant induced locomotion, disrupted CAR, and the induction of catalepsy, provide evidence of l-SPD's dopamine $D_2$ antagonism (Natesan et al. 2008, ibid.).

dl-Govadine, which has a core structure similar to that of l-SPD, has been characterized as a noradrenaline $\alpha_1$ antagonist in peripheral cardiovascular tissue (Guh et al., 1999, *European J. Pharmacology*, 374:503-510. Ko et al., 1996, *J. Pharmacy and Pharmacology*, 48:629-634). Receptor binding assays showed dl-govadine to have a higher affinity than l-SPD for the dopamine $D_1$ receptor, but a lower affinity for the $D_2$ receptor (Hu et al., 1998, ibid).

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

The present invention provides for tetrahydroprotoberbine compounds that are useful as cognitive enhancers and thus may be used in the treatment of certain neurological, psychiatric and neurodegenerative diseases. In certain aspects, the tetrahydroprotoberbine compounds are stereochemically pure.

In accordance with one aspect of the present invention, there is provided a use of a compound of formula (I):

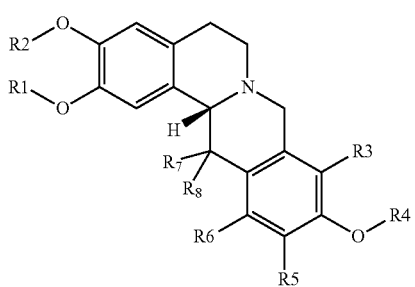

(I)

or pharmaceutically acceptable salt, solvate or prodrug thereof, for treatment of a neurological, psychiatric or neurodegenerative disease in a subject in need thereof, wherein:
R1 and R2 are independently H, alkyl, benzyl or —COR9; or R1 and R2 together form $(CH_2)_m$;

R4 is H, alkyl, benzyl, or —COR9;

R3 is H or OR10, wherein R10 is H, alkyl, benzyl or —COR9, or R10 taken together with R4 forms $(CH_2)_m$;

R5 is H or OR11, wherein R11 is H, alkyl, benzyl or —COR9, or R11 taken together with R4 forms $(CH_2)_m$;

R6 is H or halogen;

R9 is H or alkyl;

m is 1 or 2, and wherein when R10 taken together with R4 forms $(CH_2)_m$, then R5 is H or OR11, wherein R11 is H, alkyl, benzyl or —COR9, and wherein when R11 taken together with R4 forms $(CH_2)_m$, then R3 is H or OR11, wherein R11 is H, alkyl, benzyl or —COR9, and wherein at least one of R3 and R5 is other than H.

In accordance with another aspect of the present invention, there is provided a use of a compound of formula (I) as defined above, or pharmaceutically acceptable salt, solvate or prodrug thereof, in the manufacture of a medicament for treating a neurological, psychiatric or neurodegenerative disease.

In accordance with another aspect of the present invention, there is provided a use of a compound of formula (I), as defined above, or pharmaceutically acceptable salt, solvate or prodrug thereof, for increasing dopamine release in the prefrontal cortex in a subject in need thereof.

In accordance with another aspect of the present invention, there is provided a use of a compound of formula (I), as defined above, or pharmaceutically acceptable salt, solvate or prodrug thereof, in the manufacture of a medicament for increasing dopamine release in the prefrontal cortex in a subject.

In accordance with another aspect of the present invention, there is provided a use of a compound of formula (I), as defined above, or pharmaceutically acceptable salt, solvate or prodrug thereof, for treatment of a cognitive disorder in a subject in need thereof.

In accordance with another aspect of the present invention, there is provided a use of a compound of formula (I), as defined above, or pharmaceutically acceptable salt, solvate or prodrug thereof, in the manufacture of a medicament for treating a cognitive disorder.

In accordance with another aspect of the present invention, there is provided a method of treating a neurological, psychiatric or neurodegenerative disease comprising administering to a subject in need thereof an effective amount of a compound of formula (I), as defined above, or pharmaceutically acceptable salt, solvate or prodrug thereof.

In accordance with another aspect of the present invention, there is provided a method of increasing dopamine release in the prefrontal cortex comprising administering to a subject in need thereof an effective amount of a compound of formula (I), as defined above, or pharmaceutically acceptable salt, solvate or prodrug thereof.

In accordance with another aspect of the present invention, there is provided a method of treating a cognitive disorder comprising administering to a subject in need thereof an effective amount of a compound of formula (I), as defined above, or pharmaceutically acceptable salt, solvate or prodrug thereof.

In accordance with another aspect of the present invention, there is provided a compound having the structure:

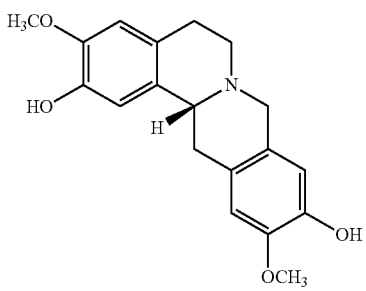

53

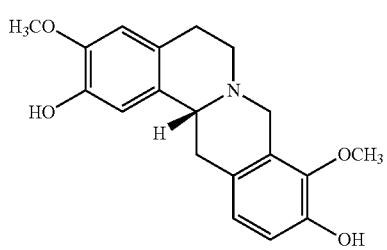

54 or a prodrug, derivative, salt, ester or solvate thereof.

In accordance with another aspect of the present invention, there is provided a pharmaceutical composition comprising a compound having the structure 53 or 54 or a prodrug, derivative, salt, ester or solvate thereof.

In accordance with another aspect of the present invention, there is provided a use of a compound having the structure 53 or 54 or a prodrug, derivative, salt, ester or solvate thereof as a cognitive enhancer.

In accordance with another aspect of the present invention, there is provided a use of a compound having the structure:

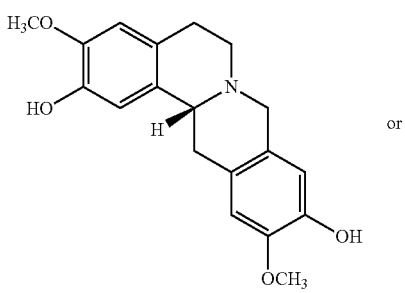

53

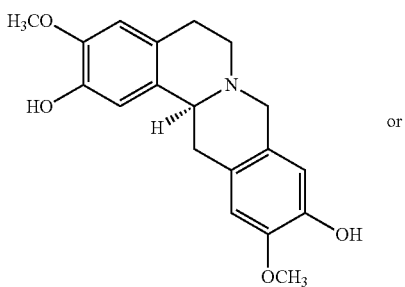

62

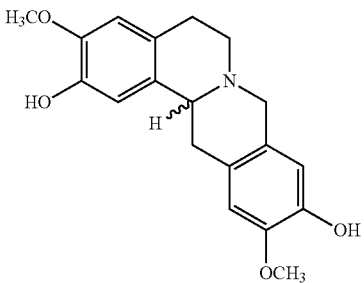

63 or a pharmaceutically acceptable salt, solvate or prodrug thereof, for treatment of a neurological, psychiatric or neurodegenerative disease in a subject in need thereof.

In accordance with another aspect of the present invention, there is provided a use of a compound having the structure 53, 62 or 63 or a pharmaceutically acceptable salt, solvate or prodrug thereof, in the manufacture of a medicament for treating a neurological, psychiatric or neurodegenerative disease.

In accordance with another aspect of the present invention, there is provided a method of treating a neurological, psychiatric or neurodegenerative disease in a subject in need thereof comprising administering to the subject an effective amount of a compound having the structure 53, 62 or 63 or a pharmaceutically acceptable salt, solvate or prodrug thereof.

In accordance with another aspect of the present invention, there is provided a use of a compound having the structure 53 or 63 or a pharmaceutically acceptable salt, solvate or prodrug thereof, for cognitive enhancement in a subject in need thereof.

In accordance with another aspect of the present invention, there is provided a of a compound having the structure 53 or 63 or a pharmaceutically acceptable salt, solvate or prodrug thereof, in the manufacture of a medicament for cognitive enhancement.

In accordance with another aspect of the present invention, there is provided a method of cognitive enhancement comprising administering to a subject an effective amount of a compound having the structure 53 or 63 or a pharmaceutically acceptable salt, solvate or prodrug thereof.

In accordance with another aspect of the present invention, there is provided a process for preparing enantiomerically pure d- or l-govadine comprising the steps:

(a) performing a coupling reaction between compounds (XVI) and (XVII) to provide amide (XVIII);

(b) performing a Bischler-Napieralski reaction on the amide (XVIII) to provide dihydroisoquinoline intermediate (XIX);

(c) reducing the dihydroisoquinoline intermediate (XIX) with a chiral catalyst to provide compound (XIV) or (XV);

(d) performing a Mannich-type cyclization on compound (XIV) or (XV) to obtain d- or l-govadine, wherein the synthesis route is as follows:

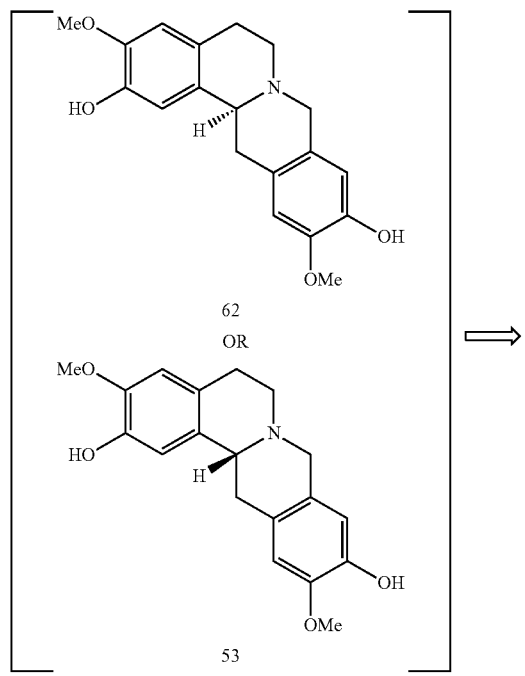

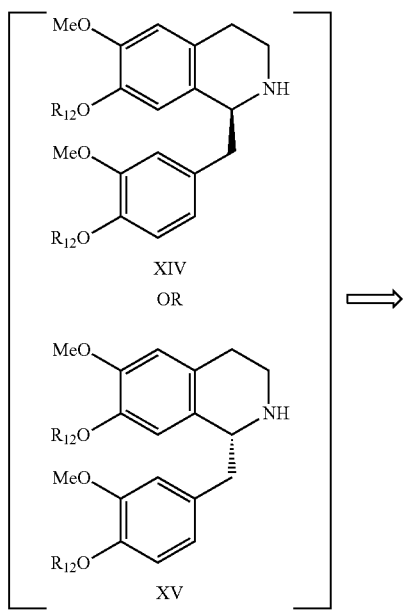

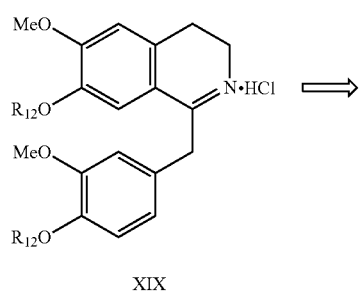

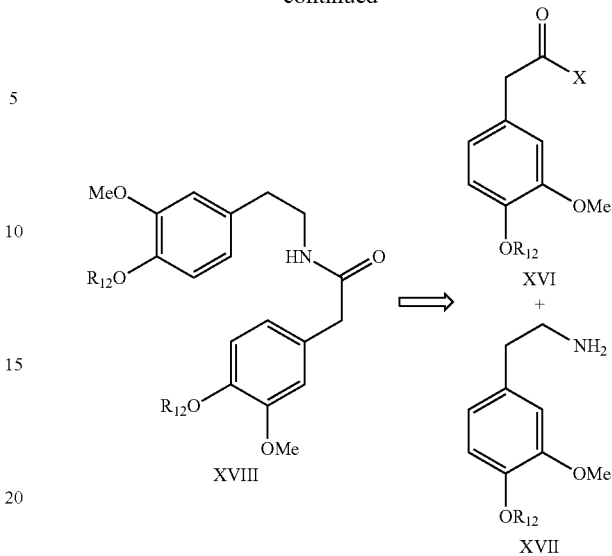

and wherein X is Cl or OH, and R12 is a protecting group.

BRIEF DESCRIPTION OF THE DRAWINGS

These and other features of the invention will become more apparent in the following detailed description in which reference is made to the appended drawings.

DETAILED DESCRIPTION OF THE INVENTION

Figure 1:
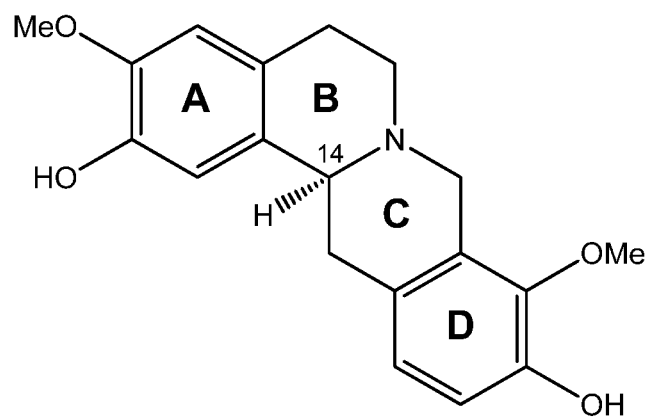
FIG. 1 presents the structure of l-stepholidine (also known as (−)- or (S)-stepholidine) showing the chiral centre at C(14) and the tetracyclic ring skeleton (rings A, B, C and D).

In one aspect, the present invention provides a class of stereochemically pure tetrahydroprotoberbine (THPB) compounds and for their use in the treatment of neurological, psychiatric (including neuropsychiatric) and neurodegenerative diseases. These compounds may generally be referred to as "d-THPB" compounds, where "d-THPB" is defined as indicated below. As described herein, d-govadine, a representative d-THPB compound of general formula (I), while showing an affinity for both the $D_1$ and $D_2$ dopamine receptors in vitro, has been shown surprisingly to increase dopamine release in the brain, indicating that d-govadine has dopamine agonistic activity, despite the antagonistic activity suggested by the in vitro receptor affinities. Moreover, while l-govadine induced an increase in dopamine in the ventral striatum/nucleus accumbens and the prefrontal cortex, d-govadine induced an increase in dopamine levels in the prefrontal cortex only. In contrast to l-govadine, d-govadine also increases cognitive function.

Accordingly, certain embodiments of the invention contemplate that d-govadine and other d-THPB compounds of general formula (I) will be useful in pharmacological contexts and, in particular in the treatment of neurological, psychiatric and neurodegenerative diseases in which dopamine agonistic activity and/or cognitive enhancement would be beneficial. A readily scalable enantioselective synthetic pathway for synthesis of compounds of general formula (I) is also provided.

As also demonstrated herein, racemic govadine is also effective in increasing dopamine release in the brain and both l-govadine and racemic govadine show properties associated with atypical antipsychotic drugs. In addition, racemic govadine, like d-govadine, shows a cognitive enhancing effect. In another aspect, therefore, the present invention provides for the use of govadine in the treatment of neurological, psychiatric and neurodegenerative diseases. Govadine may be provided in the form of d-govadine, l-govadine or racemic govadine. Certain embodiments of the invention also provide for the use of d-govadine and racemic govadine as cognitive enhancers. Some embodiments of the invention provide for the use of l-govadine and racemic govadine as anti-psychotics. A readily scalable enantioselective synthetic pathway for synthesis of d-govadine and l-govadine is also provided.

Definitions

Unless defined otherwise, all technical and scientific terms used herein have the same meaning as commonly understood by one of ordinary skill in the art to which this invention belongs.

"Enantiomerically enriched" or "enantiomerically pure," as used herein, means a stereomerically pure compound, or composition of a compound, the compound having one chiral center.

The terms "stereomerically pure" or "stereochemically pure," as used herein with reference to a compound, mean the compound or a composition thereof comprises predominantly one stereoisomer of the compound and is substantially free of other stereoisomer(s) of that compound. For example, a stereomerically pure composition of a compound having one chiral centre will be substantially free of the opposite enantiomer of the compound. A stereomerically pure composition of a compound having two or more chiral centres will be substantially free of other diastereomers of the compound. A typical stereomerically pure compound comprises about 80% by weight or greater of one stereoisomer of the compound and about 20% by weight or less of other stereoisomer(s) of the compound. For example, in various embodiments, a stereomerically pure compound comprises 90% by weight or greater of one stereoisomer of the compound and about 10% by weight or less of the other stereoisomer(s) of the compound; about 95% by weight or greater of one stereoisomer of the compound and about 5% by weight or less of the other stereoisomer(s) of the compound; about 97% by weight or greater of one stereoisomer of the compound and about 3% by weight or less of the other stereoisomer(s) of the compound; about 98% by weight or greater of one stereoisomer of the compound and about 2% by weight or less of the other stereoisomer(s) of the compound, and about 99% by weight or greater of one stereoisomer of the compound and about 1% by weight or less of the other stereoisomer(s) of the compound.

The term "alkyl," as used herein, refers to a straight chain or branched hydrocarbon of one to six carbon atoms or a cyclic hydrocarbon group of three to six carbon atoms. The alkyl group is optionally substituted with one or more substituents independently selected from hydroxyl, carboxy, halo, nitro and cyano. This term is exemplified by such groups as methyl, ethyl, n-propyl, i-propyl, n-butyl, t-butyl, l-butyl (or 2-methylpropyl), cyclopropylmethyl, i-amyl, n-amyl, hexyl, cyclopropyl, cyclobutyl, cyclopentyl, and the like.

The term "carboxy" as used herein, refers to ROC(O)—, wherein R is H or alkyl.

The terms "therapy" and "treatment," as used interchangeably herein, refer to an intervention performed with the intention of alleviating the symptoms associated with, preventing the development of, or altering the pathology of a disease, disorder or condition. Thus, the terms therapy and treatment are used in the broadest sense, and in various embodiments include one or more of the prevention (prophylaxis), moderation, reduction, and/or curing of a disease, disorder or condition at various stages. Those in need of therapy/treatment thus may include those already having the disease, disorder or condition as well as those prone to, or at risk of developing, the disease, disorder or condition and those in whom the disease, disorder or condition is to be prevented.

The term "subject" or "patient," as used herein, refers to an animal in need of treatment.

The term "animal," as used herein, refers to both human and non-human animals, including, but not limited to, mammals, birds and fish. In certain embodiments, the present invention provides for the use of govadine and the compounds of formula (I) in the treatment of human and non-human mammals.

Administration of the compounds of the invention "in combination with" one or more further therapeutic agents, is intended to include simultaneous (concurrent) administration and consecutive administration. Consecutive administration is intended to encompass various orders of administration of the therapeutic agent(s) and the compound(s) of the invention to the subject.

As used herein, the term "about" refers to an approximately +/−10% variation from a given value. It is to be understood that such a variation is always included in any given value provided herein, whether or not it is specifically referred to.

As used herein, the terms "comprising," "having," "including" and "containing," and grammatical variations thereof, are inclusive or open-ended and do not exclude additional, unrecited elements and/or method steps. The term "consisting essentially of" when used herein in connection with a composition, use or method, denotes that additional elements and/or method steps may be present, but that these additions do not materially affect the manner in which the recited composition, method or use functions. The term "consisting of" when used herein in connection with a composition, use or method, excludes the presence of additional elements and/or method steps. A composition, use or method described herein as comprising certain elements and/or steps may also, in certain embodiments consist essentially of those elements and/or steps, and in other embodiments consist of those elements and/or steps, whether or not these embodiments are specifically referred to.

As used herein, the term "d-THPB" (or "D-THPB") refers to a compound having the following stereochemistry:

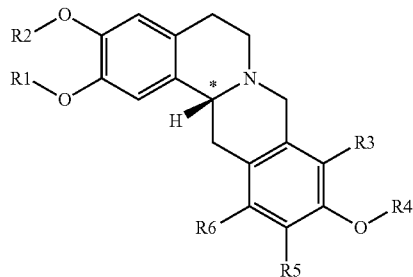

wherein the C-14 chiral centre has an R-configuration (using Cahn Ingold and Prelog nomenclature).

The term "govadine" when used herein without specification of stereochemistry, is intended to refer generally to d-govadine, l-govadine and racemic govadine.

The term "racemic" and "racemate" when used herein with reference to a THPB having d- and l-enantiomers, such as govadine, means that the compound comprises an approximately 50:50 mixture (±10%) of the d- and l-enantiomers.

It is contemplated that various embodiments discussed herein can be implemented with respect to the methods, uses or compositions of the invention, and vice versa. Furthermore, compositions and kits of the invention can be used to achieve methods and uses of the invention, and recited uses can be implemented as methods.

Stereochemically Pure Tetrahydroprotoberbine Compounds

In one aspect, the present invention provides for stereochemically pure compounds of general formula (I):

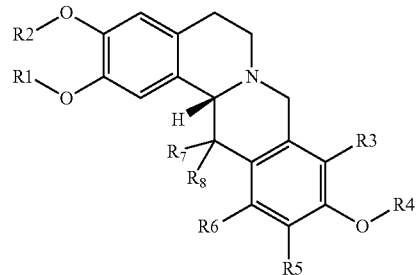

or pharmaceutically acceptable salts, solvates or prodrugs thereof, wherein:
R1 and R2 are independently H, alkyl, benzyl or —COR9; or R1 and R2 together form $(CH_2)_m$;
R4 is H, alkyl, benzyl or —COR9;
R3 is H or OR10, wherein R10 is H, alkyl, benzyl or —COR9, or R10 taken together with R4 forms $(CH_2)_m$;
R5 is H or OR11, wherein R11 is H, alkyl, benzyl or —COR9, or R11 taken together with R4 forms $(CH_2)_m$;
R6 is H or halogen;
R7 and R8 are independently H, alkyl or benzyl;
R9 is H or alkyl;
m is 1 or 2, and
wherein when R10 taken together with R4 forms $(CH_2)_m$, then R5 is H or OR11, wherein R11 is H, alkyl, benzyl or —COR9, and wherein when R11 taken together with R4 forms $(CH_2)_m$, then R3 is H or OR11, wherein R11 is H, alkyl, benzyl or —COR9, and wherein at least one of R3 and R5 is other than H.

In one embodiment, in the compound of formula (I), when R3 is H, then R5 is OR11. In some embodiments, in the compound of formula (I), when R5 is H, then R3 is OR10.

In one embodiment, in the compound of formula (I):
R1 and R2 are independently H or alkyl, or R1 and R2 together form $(CH_2)_m$;
R5 is H or O-alkyl;
R6 is H or halogen;
R7 is H;
R8 is H or alkyl; and
either R3 is H or O-alkyl, and R4 is H, or
R3 is OR10 and R10 and R4 together form $(CH_2)_m$.

In one embodiment, in the compound of formula (I):
R1 and R2 are independently H or alkyl, or R1 and R2 together form $(CH_2)_m$;
R3 is H or O-alkyl;
R6 is H or halogen;
R7 is H;
R8 is H or alkyl; and
either R4 is H, and R5 is H or O-alkyl, or
R5 is OR11 and R11 and R4 together form $(CH_2)_m$.

In one embodiment, in the compound of formula (I):
R1 and R2 are independently H or alkyl;
R3 and R5 are independently H or O-alkyl;
R4 are R7 are H;
R6 is H or halogen; and
R8 is H or alkyl.

In one embodiment, in the compound of formula (I):
R1 and R2 are independently H or alkyl;
R3 and R5 are independently H or O-alkyl;
R4, R6 and R7 are H; and
R8 is H or alkyl.

In certain embodiments, in the compound of formula (I), each alkyl is a $C_1$-$C_4$ alkyl. In some embodiments, each alkyl is a $C_1$ or $C_2$ alkyl.

In one embodiment the compound of formula (I) is a compound of formula (VII):

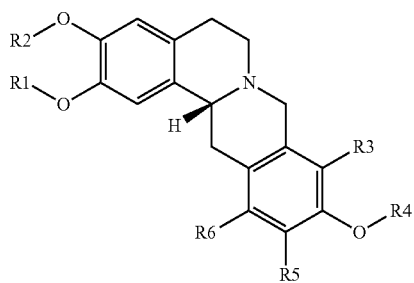

(VII)

wherein:
R1 and R2 are independently H, alkyl, benzyl or —COR9; or R1 and R2 together form $(CH_2)_m$;
R4 is H, alkyl, benzyl or —COR9;
R3 is H or OR10, wherein R10 is H, alkyl, benzyl or —COR9, or R10 taken together with R4 forms $(CH_2)_m$;
R5 is H or OR11, wherein R11 is H, alkyl, benzyl or —COR9, or R11 taken together with R4 forms $(CH_2)_m$;
R6 is H or halogen;
R9 is H or alkyl;
m is 1 or 2, and wherein when R10 taken together with R4 forms $(CH_2)_m$, then R5 is H or OR11, wherein R11 is H, alkyl, benzyl or —COR9, and wherein when R11 taken together with R4 forms $(CH_2)_m$, then R3 is H or OR11, wherein R11 is H, alkyl, benzyl or —COR9, and wherein at least one of R3 and R5 is other than H.

In one embodiment, in the compound of formula (VII):
R1 and R2 are independently H or alkyl, or R1 and R2 together form $(CH_2)_m$;
R5 is H or O-alkyl;
R6 is H or halogen, and
either R3 is H or O-alkyl, and R4 is H, or
R3 is OR10 and R10 and R4 together form $(CH_2)_m$.

In one embodiment, in the compound of formula (VII):
R1 and R2 are independently H or alkyl, or R1 and R2 together form $(CH_2)_m$;
R3 is H or O-alkyl;
R6 is H or halogen, and
either R4 is H, and R5 is H or O-alkyl, or
R5 is OR11 and R11 and R4 together form $(CH_2)_m$.

In one embodiment, in the compound of formula (VII):
R1 and R2 are independently H or alkyl;
R3 and R5 are independently H or O-alkyl;
R4 is H;
R5 is H or O-alkyl, and
R6 is H or halogen.

In one embodiment, in the compound of formula (VII):
R1 and R2 are independently H or alkyl;
R3 and R5 are independently H or O-alkyl; and
R4 and R6 are H.

In certain embodiments, in the compound of formula (VII), each alkyl is a $C_1$-$C_4$ alkyl. In some embodiments, each alkyl is a $C_1$ or $C_2$ alkyl.

In one embodiment the compound of formula (I) is a compound of formula (VIII):

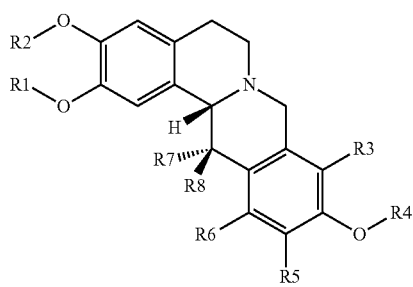

(VIII)

wherein:
R1 and R2 are independently H, alkyl, benzyl or —COR9; or R1 and R2 together form $(CH_2)_m$;
R4 is H, alkyl, benzyl or —COR9;
R3 is H or OR10, wherein R10 is H, alkyl, benzyl or —COR9, or R10 taken together with R4 forms $(CH_2)_m$;
R5 is H or OR11, wherein R11 is H, alkyl, benzyl or —COR9, or R11 taken together with R4 forms $(CH_2)_m$;
R6 is H or halogen;
R7 is alkyl;
R8 is H;
R9 is H or alkyl;
m is 1 or 2, and wherein when R10 taken together with R4 forms $(CH_2)_m$, then R5 is H or OR11, wherein R11 is H, alkyl, benzyl, or —COR9, and wherein when R11 taken together with R4 forms (CH$_2$)$_m$, then R3 is H or OR11, wherein R11 is H, alkyl, benzyl, or —COR9, and wherein at least one of R3 and R5 is other than H.

In one embodiment, in the compound of formula (VIII):
R1 and R2 are independently H or alkyl, or R1 and R2 together form (CH$_2$)$_m$;
R5 is H or O-alkyl;
R6 is H or halogen, and
either R3 is H or O-alkyl, and R4 is H, or
R3 is OR10 and R10 and R4 together form (CH$_2$)$_m$.

In one embodiment, in the compound of formula (VIII):
R1 and R2 are independently H or alkyl, or R1 and R2 together form (CH$_2$)$_m$;
R3 is H or O-alkyl;
R6 is H or halogen, and
either R4 is H, and R5 is H or O-alkyl, or
R5 is OR11 and R11 and R4 together form (CH$_2$)$_m$.

In one embodiment, in the compound of formula (VIII):
R1 and R2 are independently H or alkyl;
R3 and R5 are independently H or O-alkyl;
R4 is H; and
R6 is H or halogen.

In one embodiment, in the compound of formula (VIII):
R1 and R2 are independently H or alkyl;
R3 and R5 are independently H or O-alkyl; and
R4 and R6 are H.

In certain embodiments, in the compound of formula (VIII), each alkyl is a C$_1$-C$_4$ alkyl. In some embodiments, each alkyl is a C$_1$ or C$_2$ alkyl.

In one embodiment the compound of formula (I) is selected from:

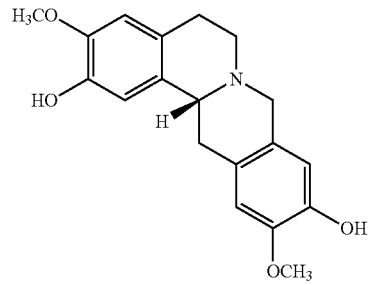
53

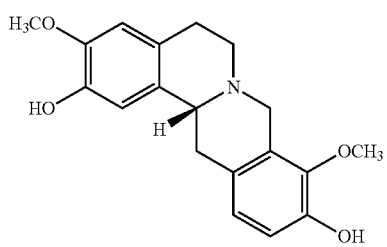
54

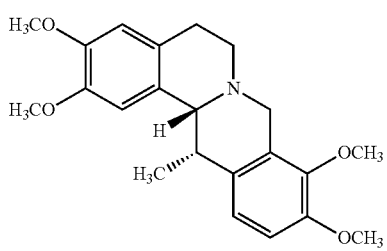
55

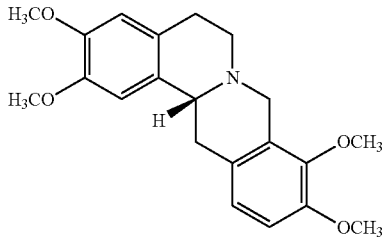
56

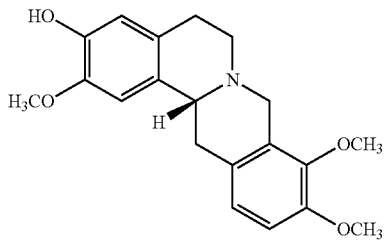
57

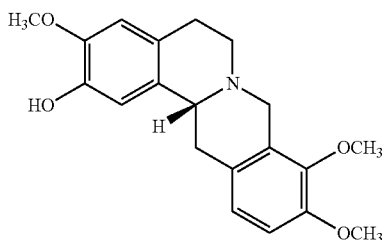
58

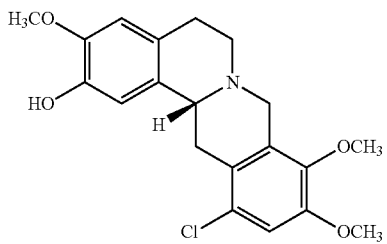
59

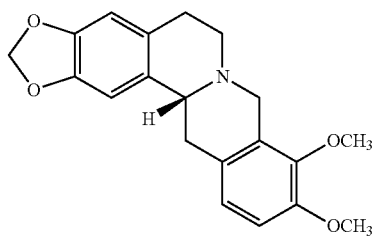
60

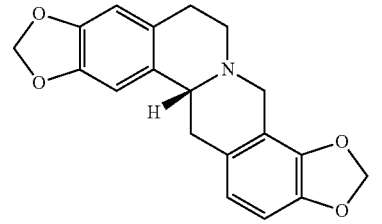
61

In one embodiment the compound of formula (I) is selected from:
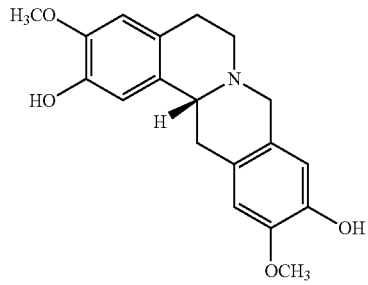
53
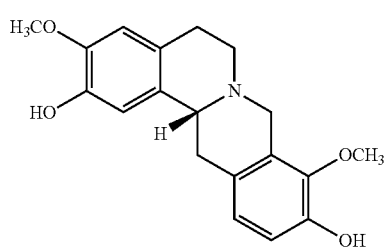
54
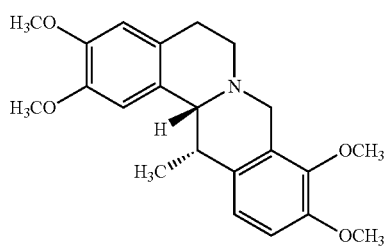
55
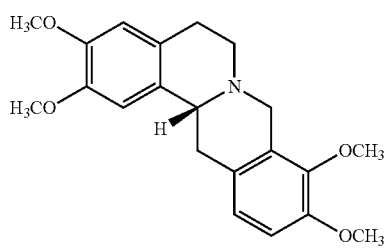
56
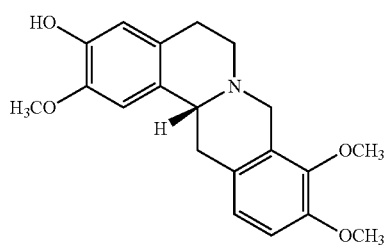
57
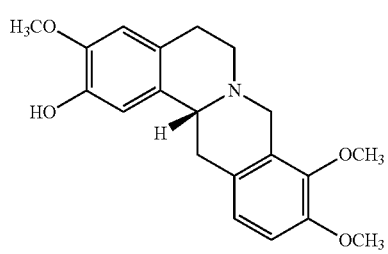
58
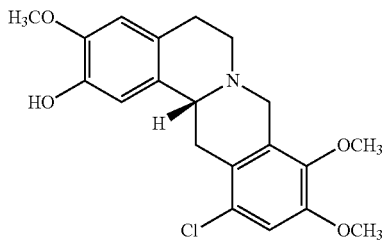
59
In one embodiment the compound of formula (I) is:
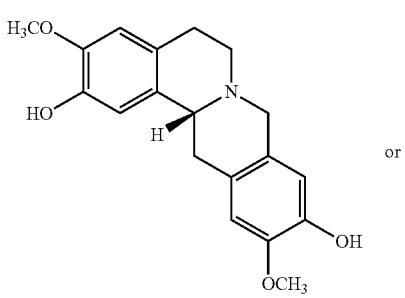
53
or
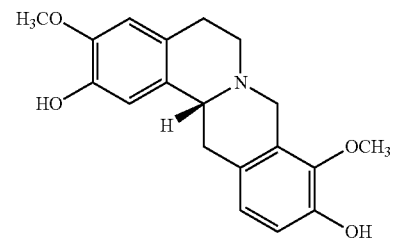
54
In one embodiment the compound of formula (I) is:
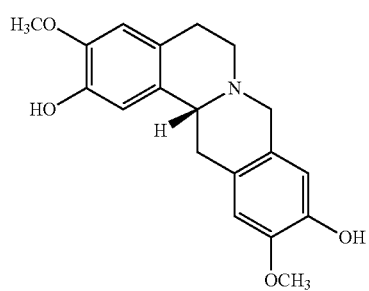
53
In one embodiment the compound of formula (I) is:
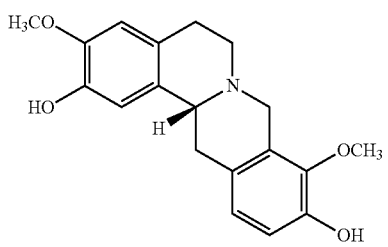
54

Also encompassed by the invention are intermediates in the preparation of compounds of Formula (I). In one embodiment, such intermediates are of general Formula (IX):

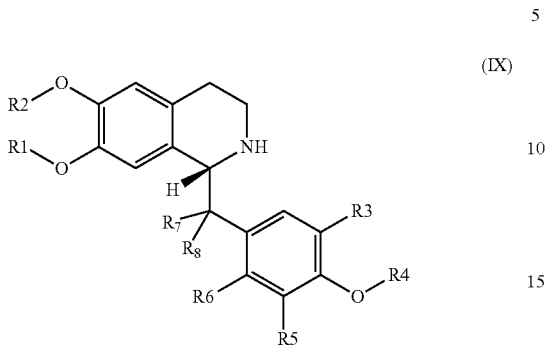

(IX)

wherein R1 through R8 are as described in any of the embodiments described above in connection with Formula (I).

Govadine

In one aspect of the invention relates to govadine, including d-govadine (53), l-govadine (62), and racemic govadine (63).

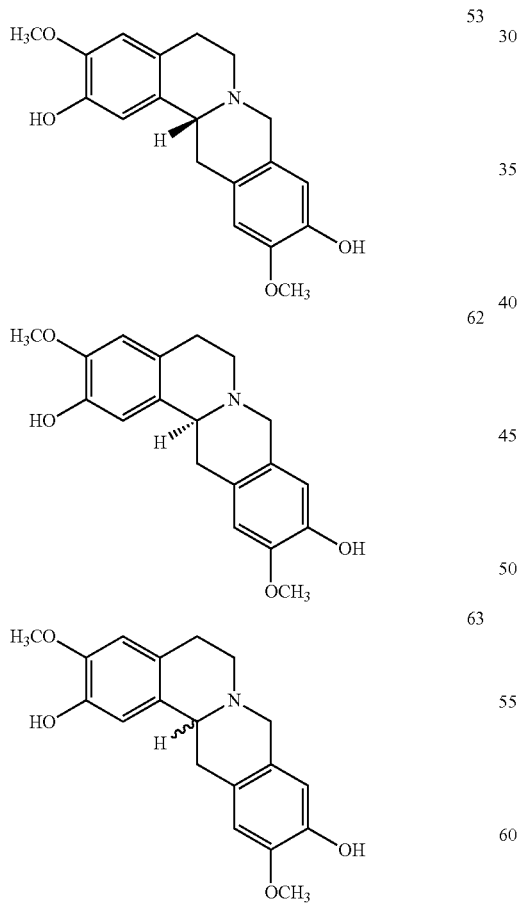

Also encompassed by certain embodiments of the invention are intermediates in the preparation of stereochemically pure d-govadine or l-govadine, such as compounds of formulae (XIV) and (XV), in which R12 is a protecting group, including compounds 22 and 23, and salts thereof.

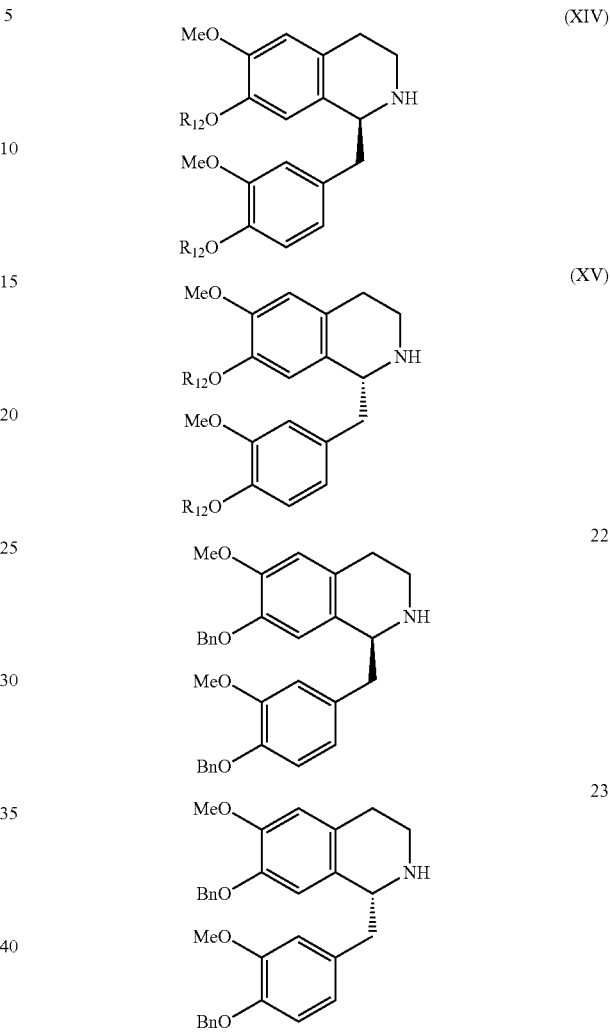

Salts, Solvates and Prodrugs

Certain embodiments of the invention relate to pharmaceutically acceptable salts, solvates and prodrugs of the compounds defined above.

Compounds according to the present invention can possess a sufficiently acidic, a sufficiently basic, or both functional groups, and accordingly react with a number of organic and inorganic bases, and organic and inorganic acids, to form pharmaceutically acceptable salts. The term "pharmaceutically acceptable salt" as used herein, refers to a salt of a compound, which is substantially non-toxic to living organisms. Typical pharmaceutically acceptable salts include those salts prepared by reaction of the compound with a pharmaceutically acceptable mineral or organic acid or an organic or inorganic base. Such salts are known as acid addition and base addition salts.

Acids commonly employed to form acid addition salts include, for example, inorganic acids such as hydrochloric acid, hydrobromic acid, hydroiodic acid, sulphuric acid, phosphoric acid, and the like, and organic acids such as p-toluenesulphonic acid, methanesulphonic acid, oxalic acid, p-bromophenylsulphonic acid, carbonic acid, succinic acid, citric acid, benzoic acid, acetic acid, and the like. Examples of such pharmaceutically acceptable salts are the sulphate, pyrosulphate, bisulphate, sulphite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulphonate, phenylacetate, phenylpropionate, phenylbutyrate, citrate, lactate, gamma-hydroxybutyrate, glycolate, tartrate, methanesulphonate, propanesulphonate, naphthalene-1-sulfonate, napththalene-2-sulfonate, mandelate and the like.

In certain embodiments, the pharmaceutically acceptable acid addition salts are those formed with mineral acids such as hydrochloric acid and hydrobromic acid, and those formed with organic acids such as maleic acid and methanesulphonic acid.

Salts of amine groups may also comprise quarternary ammonium salts in which the amino nitrogen carries a suitable organic group such as an alkyl, lower alkenyl, substituted lower alkenyl, lower alkynyl, substituted lower alkynyl, or aralkyl moiety.

Base addition salts include those derived from inorganic bases, such as ammonium or alkali or alkaline earth metal hydroxides, carbonates, bicarbonates, and the like. Bases useful in preparing salts thus include sodium hydroxide, potassium hydroxide, ammonium hydroxide, potassium carbonate, sodium carbonate, sodium bicarbonate, potassium bicarbonate, calcium hydroxide, calcium carbonate, and the like.

One skilled in the art will understand that the particular counterion forming a part of a salt in accordance with the present invention is usually not of a critical nature, so long as the salt as a whole is pharmacologically acceptable and as long as the counterion does not contribute undesired qualities to the salt as a whole.

Certain embodiments provide for pharmaceutically acceptable solvates of the compounds of the invention. For example, many of the compounds described above can combine with solvents such as water, methanol, ethanol and acetonitrile to form pharmaceutically acceptable solvates such as the corresponding hydrate, methanolate, ethanolate and acetonitrilate.

Certain embodiments provide the compounds of the invention in a prodrug form. The term "prodrug" as used herein refers to a compound that has undergone a chemical derivation such as substitution or addition of a further chemical group to change (for pharmaceutical use) one or more of its physico-chemical properties, and that yields the active compound per se by one or a series of metabolic transformations after administration to a subject. Physicochemical properties that may be changed by conversion of the compound into a prodrug form include, for example, solubility, bioavailability, absorption, distribution, site specificity, stability, release characteristics, toxicity, and the like. Examples of chemical derivatives that may be prepared in order to convert a compound into a prodrug in accordance with certain embodiments of the invention include, but are not limited to, ester derivatives, ether derivatives, carbamate derivatives, amide derivatives, imine derivatives, and derivatization with an appropriate carrier moiety directly or via a linker group. Examples of prodrugs and methods of producing a prodrug of a given active compound are well known to those skilled in the art and can be found, for example, in Krogsgaard-Larsen et al., (Textbook of Drug Design and Discovery, Taylor & Francis, New York, N.Y. (April 2002)).

The preparation of salts, solvates and prodrugs can be carried out by methods known in the art. It will be appreciated that non-pharmaceutically acceptable salts, solvates or prodrugs also fall within the scope of the invention since those may be useful in the preparation of pharmaceutically acceptable salts, solvates or prodrugs.

Preparation of Govadine and Compounds of Formula I

Tetrahydroprotoberbines of formula (I) can be prepared, for example, by a synthetic route as shown in Scheme 1, which involves the preparation of a key amide intermediate (IV) which can be produced by reacting amine (II) with acid (III) as starting materials, followed by the Bishler-Napieralski reaction with POCl$_3$ to form the planar dihydroisoquinoline intermediate (V). It is to be understood that the steps shown in Scheme 1 and the following Schemes are the key steps of the synthetic route only and the inclusion of additional intermediary steps is not precluded. For example, in certain embodiments, steps converting free acids or base to salts, crystallization and/or re-crystallization steps, various purification steps, and the like may be inserted between one or more of the steps shown in the Schemes, as would be understood by a worker skilled in the art.

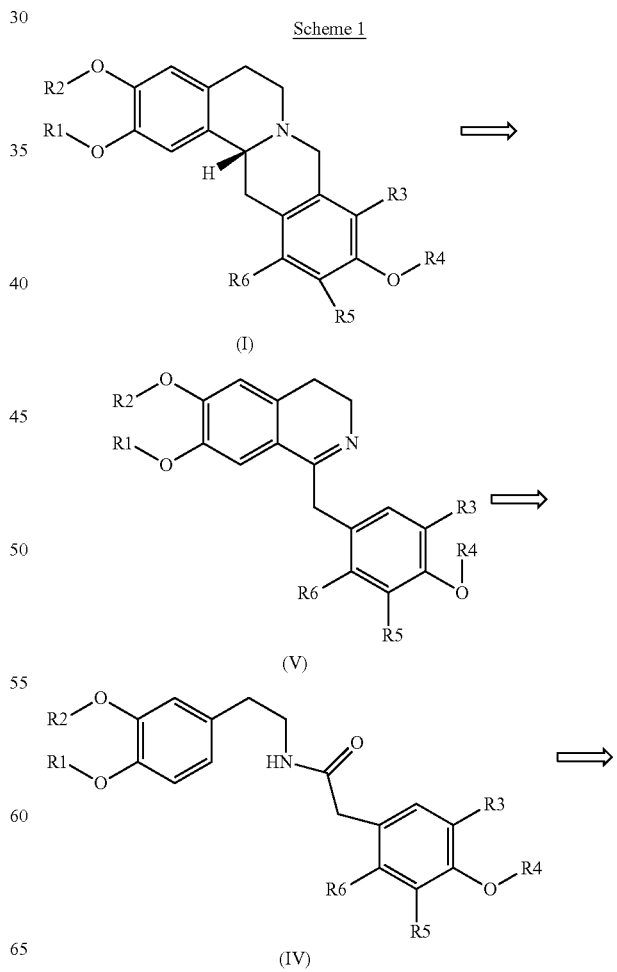

-continued

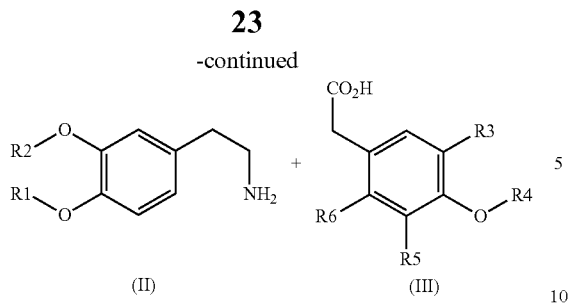

Alternatively, in Scheme 1, acid (III) may be replaced with starting compound (XIII), in which X is OH or Cl.

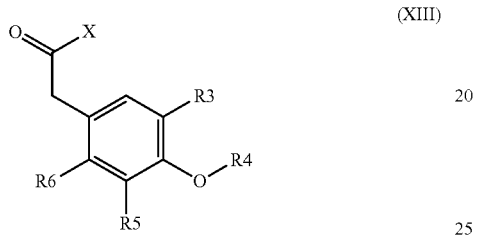

In certain embodiments, the intermediate (V) is reduced using a chiral reducing catalyst/reagent to produce intermediate (VI), followed by a Mannich-type cyclization, for example, Pictet-Spengler cyclization, of the compound (VI) to afford the desired entantiomer or diastereomer of compound (I), as shown in Scheme 2.

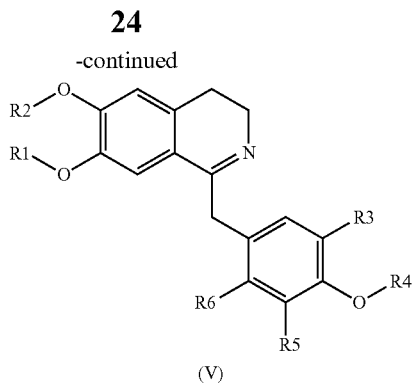

In certain embodiments, the present invention provides for a synthetic route for preparing stereochemically pure THPBs comprising five main steps as shown in Scheme 3, in which intermediate (V) is reduced using a chiral reducing catalyst/reagent. The 5-step process can be used to produce either stereoisomer of the THPB by selection of the appropriate enantiomer of a chiral reducing catalyst/reagent to reduce intermediate (V) to produce either intermediate (VI) or intermediate (XII), which is followed by a Mannich-type cyclization to produce a tetrahydroprotoberbine of formula (I) or formula (XI), respectively.

Scheme 2

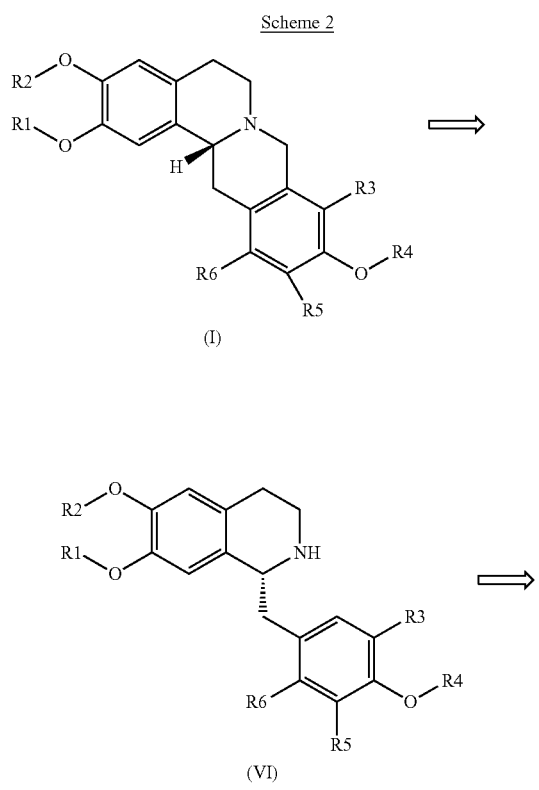

Scheme 3

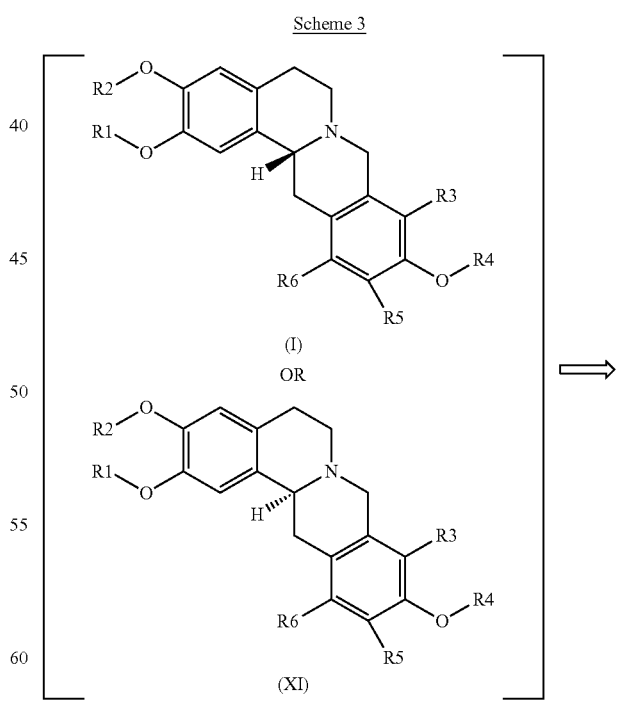

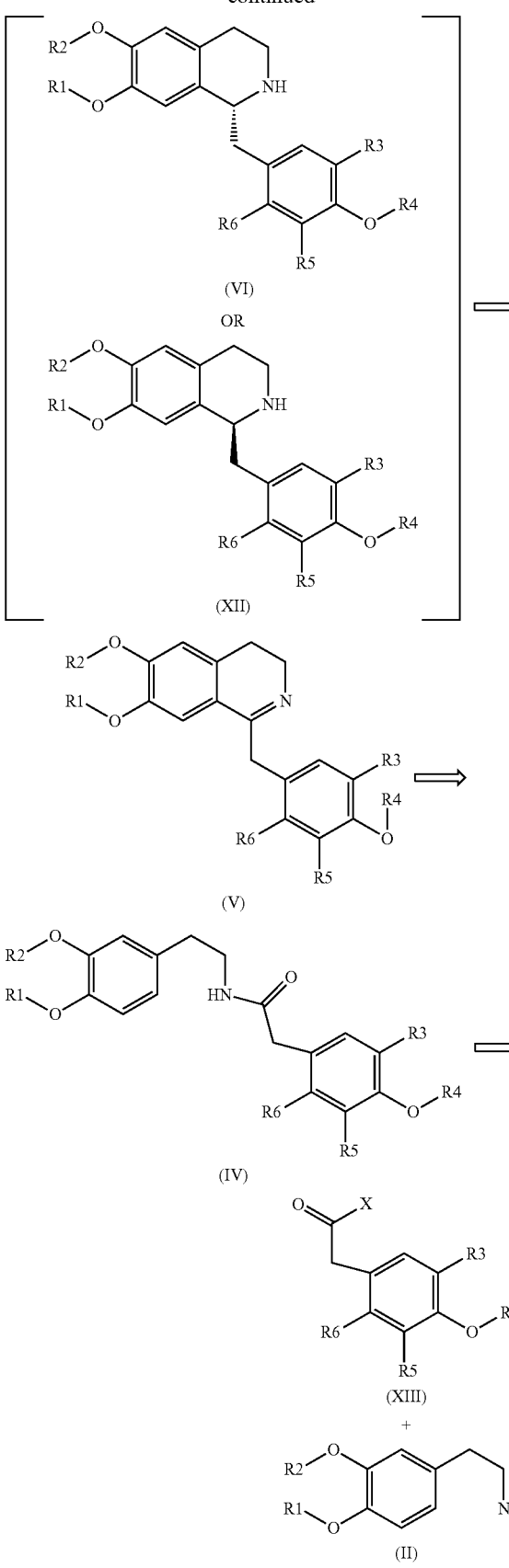

In certain embodiments, the invention provides for a synthetic route for preparing enantiomerically pure govadine comprising five main steps using the commercially available dopamine derivative 1 and homovanillic acid derivative 21 as starting materials as shown in Scheme 4. R12 is benzyl or another suitable protecting group. Suitable protecting groups can be readily selected by the skilled worker. Examples include, but are not limited to, methoxymethyl ethers, 2-(trimethylsilyl)ethoxymethyl (SEM) ethers and 4-methoxybenzyl ethers. As in Scheme 3, this route comprises coupling readily available starting materials (XVIa,b) and (XVII) to provide amide (XVIII), followed by conversion of the amide intermediate (XVIII) to the planar dihydroisoquinoline intermediate (XIX), and reducing intermediate (XIX) using a chiral reducing catalyst/reagent. The route can be used to produce either enantiomer of govadine by selection of the appropriate enantiomer of the chiral reducing catalyst/reagent in order to reduce intermediate (XIX) to produce either intermediate (XIV) or intermediate (XV). A Mannich-type cyclization followed by removal of the protecting groups produces d- or l-govadine (53 and 62, respectively).

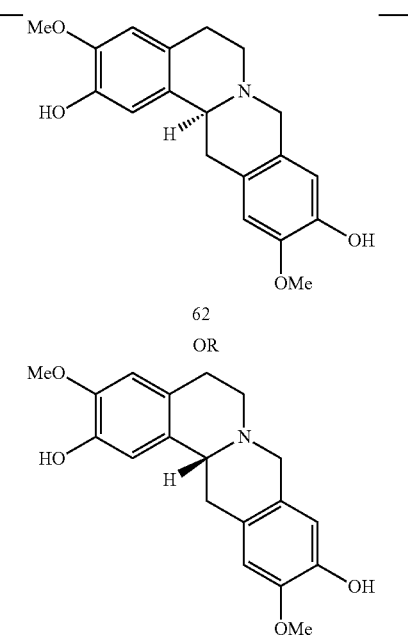

Scheme 4

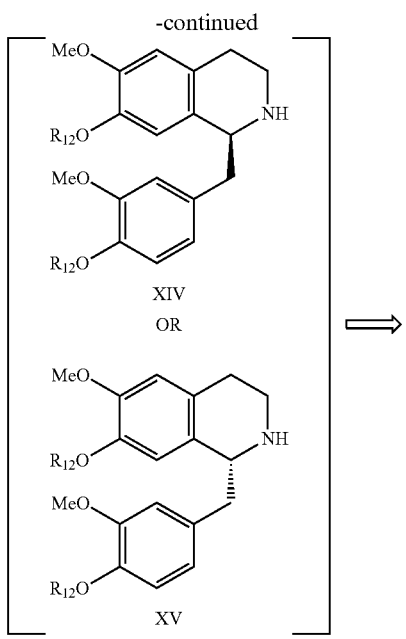

XIV

OR

XV

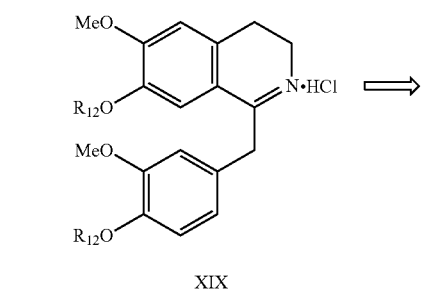

XIX coupling peptides. Non-limiting examples are provided in Example 3. Other suitable methods include, but are not limited to, coupling reactions using a carbodiimide reagent (for example, N,N'-dicyclohexylcarbodiimide (DCC) and N,N'-diisopropylcarbodiimide (DIC)) or an activated triazole reagent (for example, benzotriazol-1-yl-oxytripyrrolidinophosphonium hexafluorophosphate (PyBOP), O-benzotriazole-N,N,N',N'-tetramethyluronium hexafluorophosphate (HBTU), 2-(1H-7-azabenzotriazol-1-yl)-1,1,3,3-tetramethyluronium hexafluorophosphate (HATU), and 2-(6-chloro-1H-benzotriazole-1-yl)-1,1,3,3-tetramethylaminium hexafluorophosphate HCTU). In certain embodiments, the coupling reaction is a thermal coupling reaction. In some embodiments, the coupling reaction is a thermal coupling reaction in the absence of solvent.

Conversion of the intermediate (XVIII) to the dihydroisoquinoline intermediate (XIX) can be achieved, for example, by the Bishler-Napieralski reaction. The Bishler-Napieralski reaction typically employs condensation reagents such as $P_2O_5$, $POCl_3$ or $ZnCl_2$. In certain embodiments, the synthetic route comprises a Bishler-Napieralski reaction utilizing $POCl_3$ as a condensation reagent.

Suitable chiral reducing catalysts/reagents for reducing intermediate (XIX) include, for example, Noyori's catalyst (RuCl[(S,S)-TsDPEN(P-cymene)] or RuCl[(R,R)-TsDPEN (P-cymene)]) and other chiral catalysts known in the art.

The Mannich-type cyclization of intermediate (XIV) or intermediate (XV) can be, for example, a Pictet-Spengler cyclization.

In certain embodiments, the synthetic route comprises utilizing benzyl protecting groups as shown in Scheme 5.

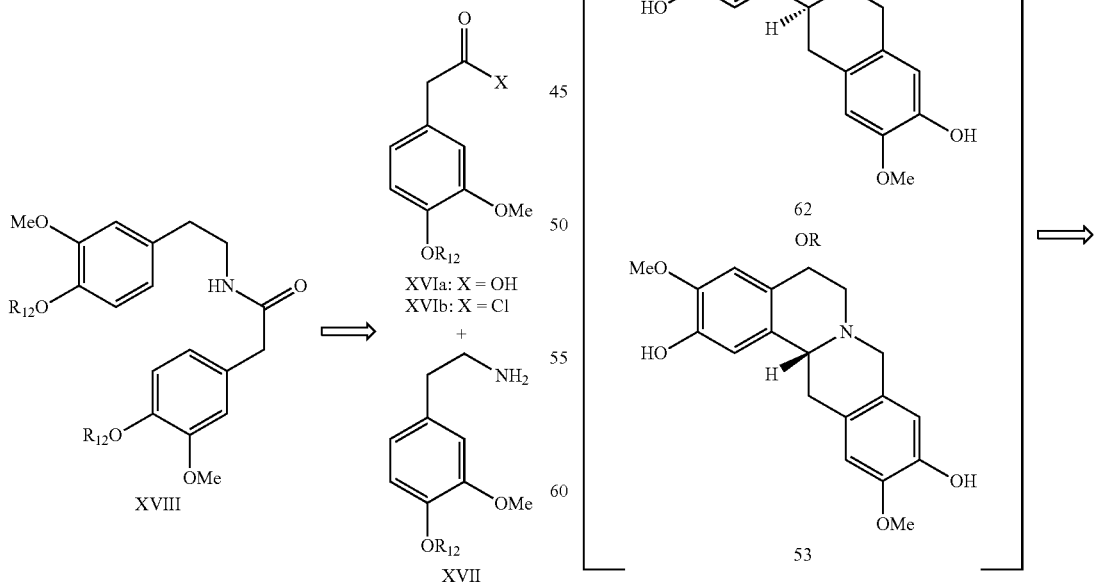

Scheme 5

Coupling of starting materials (XVIa,b) and (XVII) may be achieved by various methods known in the art for

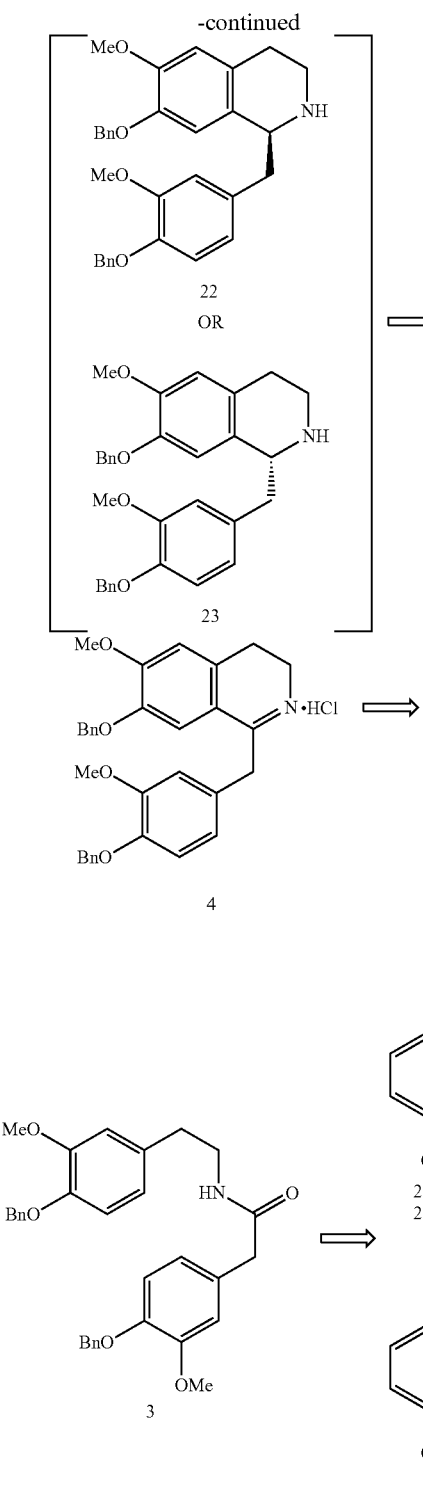

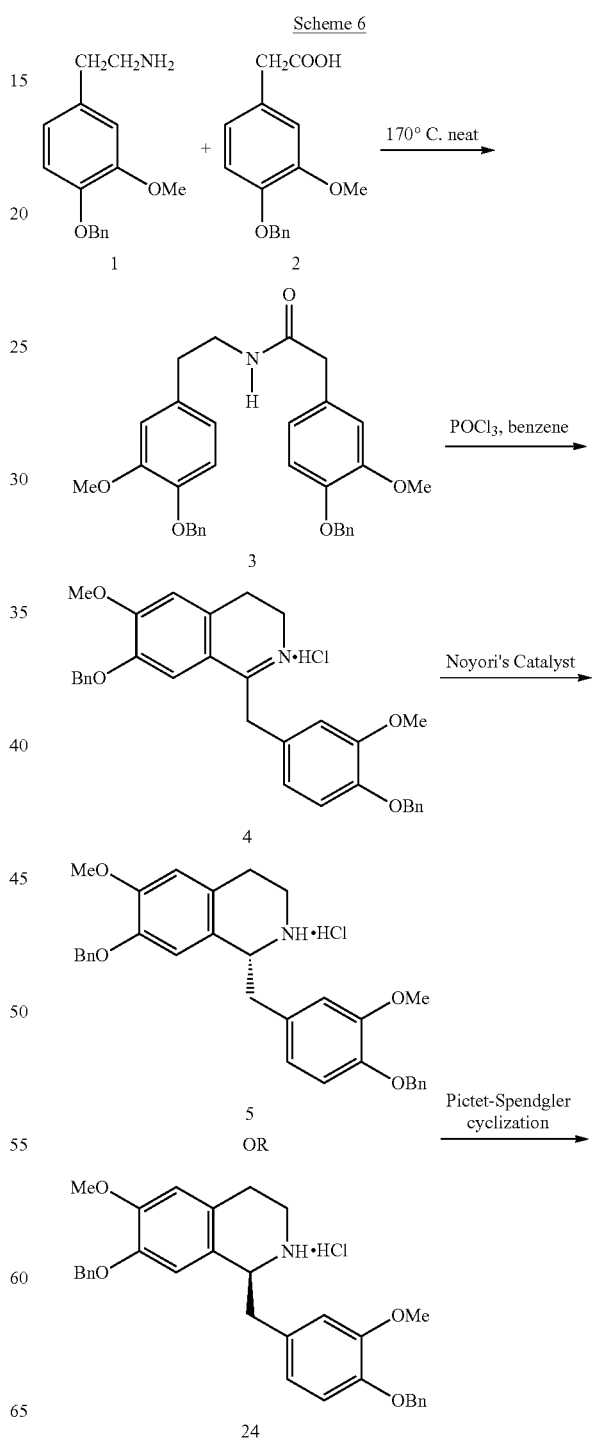

tion. The route is thus readily scalable as it does not require the use of flash chromatography. For example, preparation of intermediate (VI), intermediate (XVIII) or compound 3 by heating the respective starting (compounds (II) and (XIII), or (XVIa) and (XVII), or compounds 1 and 21a, in the absence of solvent, allows for the purification of intermediate (VI) or (XVIII), or compound 3 by crystallization.

In certain embodiments, the synthetic route comprises the steps set out in Scheme 6:

In certain embodiments, intermediate (VI), intermediate (XII), intermediate (XIV), intermediate (XV), compound 22 or compound 23 may be unstable and thus may be converted to an appropriate salt, for example, an HCl salt, by standard procedures prior to proceeding to the next step. In certain embodiments, the HCl salt may be recrystallized prior to proceeding to the next step.

In accordance with certain embodiments of the invention, the synthetic route shown in Schemes 3 to 5 can be designed such that each intermediate may be purified by crystalliza-

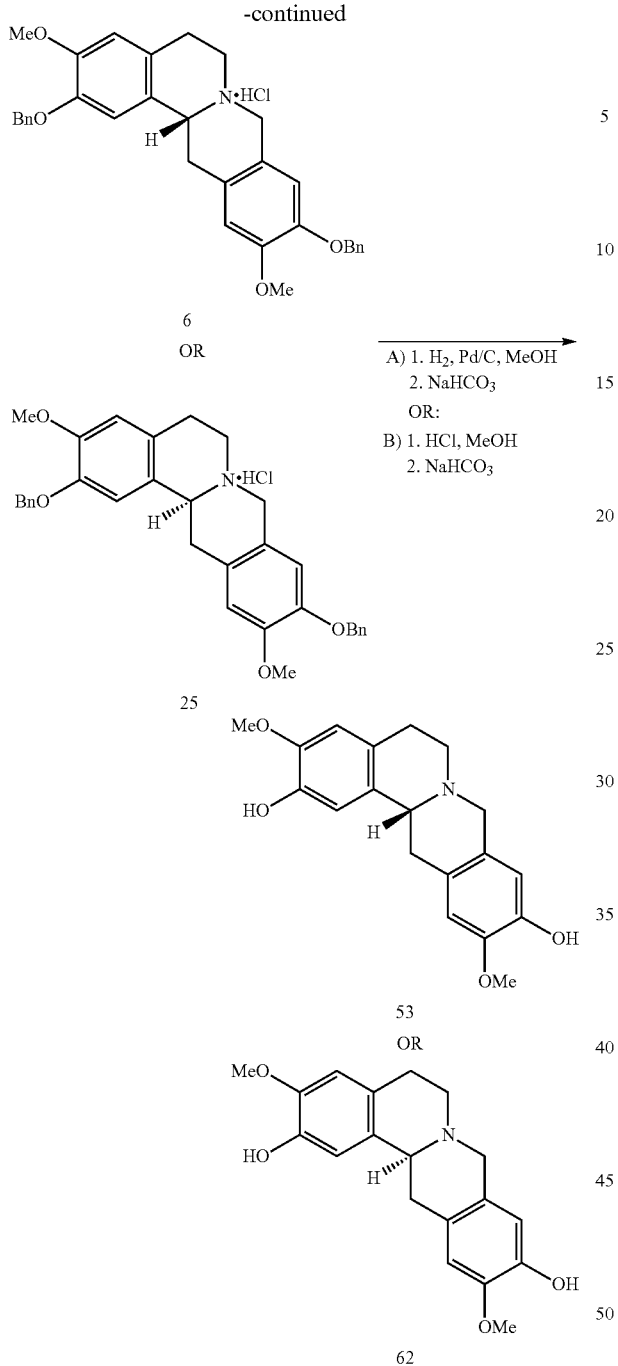

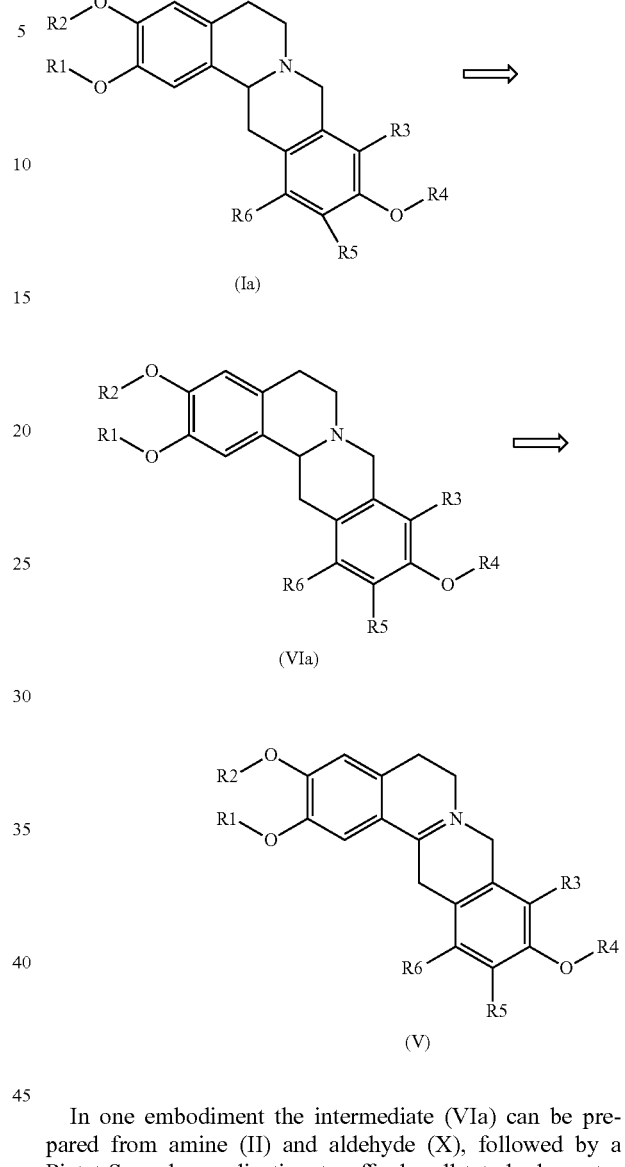

In one embodiment the intermediate (VIa) can be prepared from amine (II) and aldehyde (X), followed by a Pictet-Spengler cyclization to afford a dl-tetrahydroprotoberberine derivative which is then resolved to obtain stereochemically pure compounds, as shown in Scheme 8.

In certain embodiments in which the route depicted in Scheme 5 or 6 is carried out on a large scale, the benzyl protecting groups may be removed in a final step using HCl to minimize the possibility that some racemisation may occur.

As an alternative to the enantioselective synthesis described above, in some embodiments, intermediate (V) may be reduced using a non-chiral reducing agent, such as NaBH$_4$, to afford a racemic mixture of the compound (VIa), which is subjected to Pictet-Spengler cyclization to afford a racemic mixture of the compound of formula (Ia), which is then subjected to chiral resolution to obtain the stereochemically pure form of the compound (I), as shown in Scheme 7.

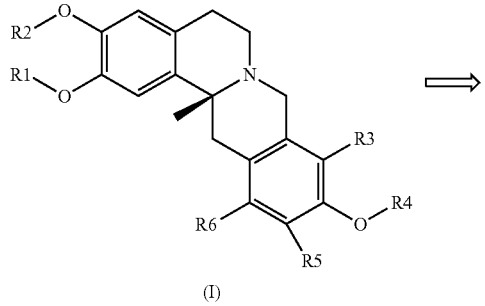

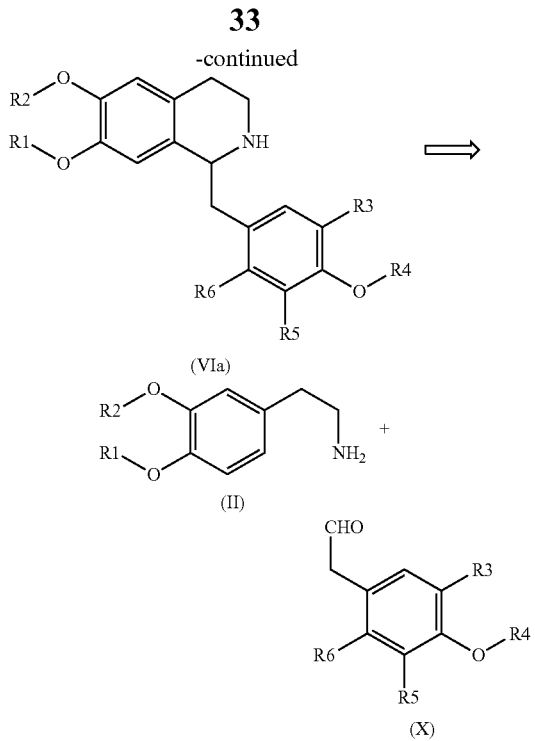

In some embodiments, the invention also encompasses the use of known stereochemically pure tetrahydroprotoberberine compounds, such as, compound 56 above. Compound 56 is commercially available from Sigma-Aldrich (St. Louis, Mo.).

In those embodiments that encompass 1-govadine, this compound may be prepared synthetically, for example, as outlined above in Schemes 5 and 6, or it may be isolated from natural sources using methods known in the art. Likewise, for those embodiments that encompass racemic govadine, this compound may be prepared as shown in Schemes 7 and 8, or by other methods known in the art.

Activity Testing

In accordance with certain embodiments of the present invention, govadine and/or compounds of formula (I) are able to increase dopamine release in the brain, and in certain embodiments are able to increase dopamine release specifically in the prefrontal cortex. This activity can be tested by the microdialysis method described in the Examples provided herein and/or other standard testing methods known in the art (see, for example in *Current Protocols in Neuroscience* (Ed. Crawley et al., John Wiley & Sons, Inc., Hoboken, N.J.).

In certain embodiments of the present invention, govadine and/or the compounds of formula (I) show a differential affinity for the $D_1$ and $D_2$ dopamine receptors. In one embodiment, compounds of formula (I) show a lower affinity for the $D_2$ receptor as compared to their affinity for the $D_1$ receptor. The affinity of the compounds for the $D_1$ and $D_2$ dopamine receptors can be assessed using standard methods known in the art, such as the methods described in the Examples provided herein.

In certain embodiments, govadine and/or the compounds of formula (I) are able to increase cognitive function. This activity can be tested by the delayed win-shift methods described in the Examples provided herein or other standard testing methods known in the art (see, for example, *Current Protocols in Neuroscience*, Ed. Crawley et al., John Wiley & Sons, Inc., Hoboken, N.J.).

Examples of the other tests that may be used to assess the activity of govadine and/or the compounds of formula (I) include, for example, the Novel Object Recognition (NOR) Test, the Pre-Pulse Inhibition Test, the Elevated X-Maze Test and the Water Maze Spatial Learning Test, as described briefly below, which test various cognitive functions. Other methods are known in the art, including those described in the Examples.

Novel Object Recognition (NOR) Test

This test is useful for evaluating the role of experimental manipulations on cognition. The recognition test is based on the natural tendency of rodents to investigate a novel object instead of a familiar one. The choice to explore the novel object reflects the use of learning and (recognition) memory processes. Novel Object Recognition (NOR) is based on the premise that rodents will explore a novel object more than a familiar one, but only if they remember the familiar one.

Description I: Before training the animals with objects, they are first allowed to acclimatize to the testing environment, which is typically a box (for example made from white Perspex) equipped with an overhead camera. After an acclimation session, the animals are ready for the training stage. This stage involves the introduction of two identical objects to the environment before allowing the rodent to explore for a suitable period (for example, about five minutes). Following the training period, the rodent is removed from the environment for a delay period which can range from 5 minutes to about 48 hours, depending on the type of memory being tested. After the delay, the rodent is returned to the arena, where one of the original objects has been replaced by a new one, such as a glass container.

Description II: In the two-trial novel object recognition task, a rodent is placed in an enclosure and exposed for a set length of time to two identical objects that are located a specified distance from each other. The rodent is then removed from the environment and a predetermined amount of time is allowed to pass. The subject is then retested in the same environment except that one of the two previously used (familiar) objects is replaced with a novel object that differs from the familiar object in shape, texture and appearance (such as, for example, plastic block is replaced with a metal ball), and the rodent's behaviour is recorded.

The amount of time that the rodents spends exploring each object can be calculated by hand or by using a computer program receiving input from the overhead camera. The literature describes a variety of methods for analyzing results. One technique involves dividing the time spent exploring the novel object by the total time spent exploring either object, yielding % novel exploration. An alternative technique is used to calculate the discrimination ratio, defined as the difference in exploration time for the objects divided by total exploration time. The method of analysis should be suited to the specific experimental setup.

Although simple by design, the NOR test is quite flexible. For instance, changing the duration of the delay period allows one to selectively test short-term or long-term memory. Alternatively, the NOR protocol can be used to selectively test the effects of an acute drug treatment on a specific stage of memory formation. The experimenter can manipulate memory encoding, consolidation or retrieval by injecting the drug prior to the training, delay or testing period, respectively. The desired result is a reduced exploratory time and enhanced spatial learning in response to a test agent in the NOR test.

Pre-Pulse Inhibition Test

The overall goal of this test is to evaluate the effect of an agent on sensory processing (which is a form of working memory). Pre-pulse inhibition is a procedure whereby a preceding stimulus attenuates the startle response. The reduced ability to filter out irrelevant auditory stimulation is a characteristic which is thought to contribute to certain manifestations of conditions including inattention, distractibility, and cognitive deficits. The test is useful for evaluating potential antipsychotic drugs.

Prepulse Inhibition (PPI) is a neurological phenomenon in which a weaker pre-stimulus (pre-pulse) inhibits the reaction of an organism to a subsequent strong startling stimulus (pulse). The stimuli are usually acoustic, but tactile, light, airpuff stimuli are also used. The reduction of the amplitude of startle reflects the ability of the nervous system to temporarily adapt to a strong sensory stimulus when a preceding weaker signal is given to warn the organism. PPI is detected in numerous species ranging from mice to humans. Although the extent of the adaptation affects numerous systems, the most comfortable to measure are the muscular reactions, which are normally diminished as a result of the nervous inhibition.

The following is an example of a PPI testing method. The test rodent is placed in a small chamber and exposed to a brief pulse of noise. The test is used to assess the subject's ability to "gate" or filter environmental information. In the acoustic (startle model) of sensorimotor gating, a weak acoustic stimulus (i.e. the pre-pulse) decreases the reflexive flinching response (startle) produced by a second, more intense, stimulus (the pulse). The main three parts of the procedure are pre-pulse, startle stimulus, and startle reflex. Different pre-pulse-to-pulse intervals, or lead intervals, can be used, for example 30, 60, 120, 240 and 480 ms. Lead interval counts from the start of pre-pulse to the start of the pulse. With the interval exceeding 500 ms, prepulse facilitation, such as increased response, is most likely to follow. Burst of white noise is usually used as acoustic startle stimulus. Typical durations are 20 ms for pre-pulse and 40 ms for pulse. Background noise of 30-40 dB is typically used in rodent experiments. Pre-pulse is typically set 3-12 dB louder than background. Startle response is measured in rodents using the so-called automated "startle chambers" or "stabilimeter chambers," with detectors recording whole-body reaction. "Pulse alone" results are compared to "pre-pulse plus pulse," and the percentage of the reduction in the startle reflex represents pre-pulse inhibition.

Elevated X-Maze Test

The elevated X-Maze, otherwise known as the Elevated Plus Maze, is a test that relies on the inherent conflict between exploration of a novel area and avoidance of its aversive features. The test may be used in male or female rats or mice, or in male gerbils. The maze consists of four arms in the form of an x or plus: two open arms and two arms of the same size, also with an open roof but enclosed by walls. The two open arms are opposite each other and converge into a central platform. The animal under investigating is observed by a video camera and its movements scored, for example by the tracking software. During the experiment the animal is placed on the central platform of the maze facing an open arm and is observed for a specified time period, for example 5 minutes, with the following being measured: number of entries into open arms, number of entries into closed arms, time spent in open arms, time spent in closed arms and finally the time spent in the central square (File et al., *Current Protocols in Neuroscience* (2004) 8.3.1-8.3.22).

Water Maze Spatial Learning Test

The Morris Water Maze (MWM) is a test of spatial learning for rodents that relies on distal cues to navigate from start locations around the perimeter of an open swimming arena to locate a submerged escape platform. Spatial learning is assessed across repeated trials and reference memory is determined by preference for the platform area when the platform is absent.

The test apparatus consists of a large circular pool (typical dimensions: about 1 m diameter and about 80 cm high, with the water at a temperature of about 26° C.) with a platform (for example, about 11 cm diameter) submerged approximately 1.5 cm below the surface. Both the pool and the platform can be constructed of black polyvinyl plastic, which offers no intra-maze cues. The experimental room may contain several extra-maze visual cues. During training, the platform is hidden in the same quadrant approximately 30 cm away from the edge of the maze. Several trials can be conducted, each beginning with the rat facing the wall of the maze in a different location. The time taken for the rat to find the platform within a specified time period is recorded. Probe trials where the platform is removed from the maze and the time the animal spent in the target quadrant can also be performed.

Govadine and compounds of formula (I) may also be tested for their efficacy in various animal models of neurological and neurodegenerative diseases, such as animal models of schizophrenia, Parkinson's disease, ADHD, dyskinesia, addiction and the like (see, for example, *Current Protocols in Neuroscience*, Ed. Crawley et al., John Wiley & Sons, Inc., Hoboken, N.J.).

Pharmaceutical Compositions

The compounds of the present invention are typically formulated prior to administration. The present invention thus provides pharmaceutical compositions comprising govadine or one or more compounds of Formula I and a pharmaceutically acceptable carrier, diluent, or excipient. The pharmaceutical compositions are prepared by known procedures using well-known and readily available ingredients.

Pharmaceutical compositions comprising the compounds may be administered orally (including, for example, buccally or sublingually), topically, parenterally, by inhalation or spray, or rectally in dosage unit formulations containing conventional non-toxic pharmaceutically acceptable carriers, adjuvants and vehicles. The term parenteral as used herein includes subcutaneous injections, intradermal, intra-articular, intravenous, intramuscular, intravascular, intrasternal, intrathecal injection or infusion techniques.

Compositions intended for oral use may be prepared in either solid or fluid unit dosage forms. Fluid unit dosage form can be prepared according to procedures known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations. An elixir is prepared by using a hydroalcoholic (for example, ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Solid formulations such as tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate: granulating and disintegrating agents for example, corn starch, or alginic acid:

binding agents, for example starch, gelatin or acacia, and lubricating agents, for example magnesium stearate, stearic acid or talc and other conventional ingredients such as dicalcium phosphate, magnesium aluminum silicate, calcium sulfate, starch, lactose, methylcellulose, and functionally similar materials. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Soft gelatin capsules are prepared by machine encapsulation of a slurry of the compound with an acceptable vegetable oil, light liquid petrolatum or other inert oil.

Aqueous suspensions contain active materials in admixture with excipients suitable for the manufacture of aqueous suspensions. Such excipients are suspending agents, for example sodium carboxylmethylcellulose, methyl cellulose, hydropropylmethylcellulose, sodium alginate, polyvinylpyrrolidone, gum tragacanth and gum acacia: dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example hepta-decaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl-p-hydroxy benzoate, one or more colouring agents, one or more flavouring agents or one or more sweetening agents, such as sucrose or saccharin.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oil phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

The pharmaceutical compositions may be in the form of a sterile injectable aqueous or oleaginous suspension. This suspension may be formulated according to known art using those suitable dispersing or wetting agents and suspending agents that have been mentioned above. The sterile injectable preparation may also be a sterile injectable solution or a suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. Adjuvants such as local anaesthetics, preservatives and buffering agents can also be included in the injectable solution or suspension.

Compositions formulated for rectal administration are usually in the form of suppositories. These compositions can be prepared by mixing the compound with a suitable non-irritating excipient which is solid at ordinary temperatures but liquid at the rectal temperature and will therefore melt in the rectum to release the compound. Such materials include cocoa butter and polyethylene glycols.

Other pharmaceutical compositions and methods of preparing pharmaceutical compositions are known in the art and are described, for example, in "*Remington: The Science and Practice of Pharmacy*" (formerly "*Remingtons Pharmaceutical Sciences*"); Gennaro, A., Lippincott, Williams & Wilkins, Philidelphia, Pa. (2000).

Administration

Govadine and compounds of Formula I may be administered to a subject by a variety of routes depending on the disease to be treated, for example, in various embodiments the compounds may be administered orally, topically, parenterally, by inhalation or spray, or rectally in dosage unit formulations.

The dosage to be administered is not subject to defined limits, but it will usually be an effective amount. It will usually be the equivalent, on a molar basis of the pharmacologically active free form produced from a dosage formulation upon the metabolic release of the active free drug to achieve its desired pharmacological and physiological effects. The compositions may be formulated in a unit dosage form. The term "unit dosage form" refers to physically discrete units suitable as unitary dosages for human subjects and other animals, each unit containing a predetermined quantity of active material calculated to produce the desired therapeutic effect, in association with a suitable pharmaceutical excipient. Examples of ranges for the compound(s) in each dosage unit are from about 0.05 to about 100 mg, or more usually, from about 1.0 to about 50 mg.

Daily dosages of the compounds of the invention will typically fall within the range of about 0.01 to about 100 mg/kg of body weight, in single or divided dose. However, it will be understood that the actual amount of the compound(s) to be administered will be determined by a physician, in the light of the relevant circumstances, including the condition to be treated, the chosen route of administration, the actual compound administered, the age, weight, and response of the individual patient, and the severity of the patient's symptoms. The above dosage range is given by way of example only and is not intended to limit the scope of the invention in any way. In some instances dosage levels below the lower limit of the aforesaid range may be more than adequate, while in other cases still larger doses may be employed without causing harmful side effects, for example, by first dividing the larger dose into several smaller doses for administration throughout the day.

The present invention also contemplates that govadine and the compounds of formula (I) may be administered as part of a combination therapy as described in more detail below.

Applications

In certain embodiments, the present invention provides for the use of govadine and compounds of general formula (I) in pharmacological contexts. The ability of compounds of formula (I), such as d-govadine, to increase dopamine release in the brain and increase cognitive function, indicates that these compounds will be useful in the treatment of neurological, psychiatric and neurodegenerative diseases, as well as to treat addiction, and as cognitive enhancers.

In certain embodiments, therefore, the invention contemplates the use of govadine and compounds of general formula (I) in the treatment of neurological and neurodegenerative diseases. Some embodiments of the invention contemplate the use of govadine and the compounds of general formula (I) in the treatment of psychiatric diseases or disorders. In certain embodiments, the invention c the use of compounds of formula (I), including d-govadine, as cognitive enhancers.

In certain embodiments, the invention provides for the use of compounds of general formula (I) in the treatment of neurological and neurodegenerative diseases in which dopamine agonistic activity and/or cognitive enhancement would be beneficial. Examples include, but are not limited to, Parkinson's disease, dementia related to Parkinson's disease, restless leg syndrome, schizophrenia, cognitive impairment associated with schizophrenia, attention deficit hyperactivity disorder (ADHD), sleep disorders, dementia and mild cognitive impairment.

Certain embodiments of the invention provide for the use of govadine and the compounds of formula (I) in the treatment of neurological and neurodegenerative diseases such as Parkinson's disease, dementia related to Parkinson's disease, subacute sclerosing panencephalitic parkinsonism, postencephalitic parkinsonism, L-dopa-induced dyskensia, pugilistic encephalitis, guam parkinsonism-dementia complex, Pick's disease, corticobasal degeneration, frontotemporal dementia, Huntington's Disease, AIDS associated dementia, dementia with Lewy bodies (DLB), restless leg syndrome, schizophrenia, cognitive impairment associated with schizophrenia, attention deficit disorder (ADD), attention deficit hyperactivity disorder (ADHD), sleep disorders, dementia, cognitive disorders, and mild cognitive impairment.

In certain embodiments, the present invention provides for the use of govadine and the compounds of formula (I) in the treatment of schizophrenia. In one embodiment, the present invention provides for the use of the compounds of formula (I) in the treatment of the negative symptoms of schizophrenia and/or cognitive deficits associated with schizophrenia.

In one embodiment, the present invention provides for the use of the compounds of formula (I) in the treatment of Parkinson's disease and/or dementia related to Parkinson's disease. In one embodiment, the present invention provides for the use of the compounds of formula (I) in the treatment of L-dopa-induced dyskensia.

In certain embodiments, the present invention provides for the use of the compounds of formula (I) in the treatment of cognitive disorders. As used herein, the term "cognitive" includes, but is not limited to, cognitive deficits such as deficits in different cognitive domains such as memory, visuospatial processing, attention, concept formation, and executive functions. Specific examples of cognitive disorders include, but are not limited to, autism, dyslexia, attention deficit hyperactivity disorder (ADHD), anxiety, schizophrenia, schizoaffective disorder, cognitive and attention deficit disorders associated with acquired immunodeficiency syndrome (AIDS), ischemic stroke, dystonia, Wilson's disease, inherited ataxia, cardiac bypass associated cognitive defects, obsessive compulsive disorders, psychosis, bipolar disorders, Tourette's syndrome, mild cognitive impairment (MCI) and disorders of learning in children, adolescents and adults, Age Associated Memory Impairment, Age Associated Cognitive Decline and Down's Syndrome.

In certain embodiments, the present invention provides for the use of govadine and the compounds of formula (I) in the treatment of mood disorders, emotions, mood swings and cognitive disorders related to psychiatric disturbances that are expressed, for example, as sleep disorders, anorexia, bulimia, post-partum depression, post-partum psychosis, pre-menstrual syndrome, manic depression, obsessive compulsive disorders, and delusional disorders. In certain embodiments the compounds of formula (I) can be used to prevent drug dependence or tolerance including that produced by nicotine, opioids such as morphine, cocaine and barbiturates such as diaxepam, and/or to prevent or treat emotional and/or cognitive disturbances or psychoses associated with drug withdrawal or cessation tolerance including that produced by nicotine, opioids such as morphine, cocaine and barbiturates such as diaxepam.

In certain embodiments, the present invention provides for the use of govadine and the compounds of formula (I) in the treatment of addiction. The addiction to be treated may be to a substance or to an activity. For example, in certain embodiments, the compounds of general formula (I) may be used to treat an addiction to a chemical substance, such as a drug, alcohol or tobacco. Examples of addictive chemical substances include stimulants (such as cocaine, amphetamines, methamphetamines, methylphenidate and related stimulants), opiates (such as heroin, codeine, hydrocodone and related opioid drugs), nicotine, alcohol, prescription medications (including medications prescribed for pain management such as Percodan® or Percocet®), and naturally-occurring plant-derived drugs (such as marijuana, tobacco, and the addictive agents therein). In certain embodiments, the compounds of general formula (I) can be used to treat patients being treated with methadone, for example, to help such patients step-down and discontinue use of methadone.

In some embodiments, the compounds of general formula (I) may be used to treat an addiction to an activity, such as gambling, sex, or eating. In certain embodiments, the present invention provides for the use of the compounds of general formula (I) to treat substance abuse.

In some embodiments, the invention provides for the use of d-govadine and racemic govadine as cognitive enhancers, and for the use of l-govadine and racemic govadine as antipyschotics.

Combination Therapy

Certain embodiments of the present invention also contemplate that govadine and the compounds of formula (I)

may be administered as part of a combination therapy. Accordingly, certain embodiments provide for combination therapies in which a subject is administered a compound of the invention in conjunction with a known neuropharmaceutical (i.e. an agent known to have an effect in the treatment of neurological or neurodegenerative diseases), for example, an antipsychotic, an antidepressant, a psychostimulant, a mood stabilizer, an anxiolytic, an Alzheimer's disease therapeutic, a Parkinson's disease therapeutic, and the like.

In certain embodiments (for example, for the treatment of schizophrenia, bipolar disorder, and the like) the neuropharmaceutical may be an antipsychotic drug. Examples of antipsychotic drugs include, but are not limited to, butyrophenone (for example, Haloperidol (HALDOL®) and Droperidol (DROLEPTAN®)); phenothiazine (for example, chlorpromazine (THORAZINE®), fluphenazine (PROLIXIN®), perphenazine (TRILAFON®), prochlorperazine (COMPAZINE®), thioridazine (MELLARIL®), trifluoperazine (STELAZINE®), mesoridazine, promazine, triflupromazine (VESPRIN®), levomepromazine (NOZINAN®) and promethazine (PHENERGAN®)); thioxanthene (for example, chlorprothixene (CLOXAN®, TARACTAN®, TRUXAL®), Clopenthixol (SORDINAL®), flupenthixol (DEPIXOL®, FLUANXOL®), thiothixene (NAVANE®) and zuclopenthixol (CLOPIXOL®, ACUPHASE®)); clozapine (CLOZARIL®); olanzapine (ZYPREXA®); risperidone (RISPERDAL®, RISPERDAL CONSTA®); quetiapine (SEROQUEL®); ziprasidone (GEODON®); amisulpride (SOLIAN®); asenapine (SAPHRIS®); paliperidone (INVEGA®); Iloperidone (FANAPT®); Zotepine (NIPOLEPT®, LOSIZOPILON®, LODOPIN®, SETOUS®); Sertindole (SERDOLECT®); Aripiprazole (ABILIFY®); dopamine partial agonists (BIFEPRUNOX®, NORCLOZAPINE® (ACP-104)); lamotrigine (LAMICTAL®); memantine (AXURA®, AKATINOL®, NAMENDA®, EBIXA®, ABIXA®); tetrabenazine (NITOMAN®, XENAZINE®); cannabidiol; LY2140023, and the like.

In certain embodiments (for example, for the treatment of depression, panic disorder, social phobia, generalized anxiety disorder (GAD), and the like) the neuropharmaceutical may be an antidepressant and/or mood stabilizer. Examples of antidepressants include, but are not limited to, a tricyclic antidepressant (for example, IMIPRAMINE® and variants); a selective serotonin reuptake inhibitor (SSRI) (for example, fluoxetine (PROZAC®), paroxetine (PAXIL®, SEROXAT®), escitalopram (LEXAPRO®, ESIPRAM®), citalopram (CELEXA®), sertraline (ZOLOFT®) and fluvoxamine (LUVOX®)); a serotonin-norepinephrine reuptake inhibitor (SNRI) (for example, venlafaxine (EFFEXOR®)); milnacipram and duloxetine (CYMBALTA®); a noradrenergic and specific serotonergic antidepressant (NASSA) (for example, mirtazapine (AVANZA®, ZISPIN®, REMERON®) and mianserin); a norepinephrine (noradrenaline) reuptake inhibitor (NRI) (for example, reboxetine (EDRONAX®)); a norepinephrine-dopamine reuptake inhibitor (for example, bupropion (WELLBUTRIN®, ZYBAN®)); Amitriptyline; Nortriptiline; Protriptyline; Desipramine; Trimipramine; Amoxapine; Bupropion; Bupropion SR; S-Citalopram; Clomipramine; Doxepin; Isocarboxazid; Velafaxine XR; Tranylcypromine; Trazodone; Nefazodone; Phenelzine; Lamatrogine; Lithium; Topiramate; Gabapentin; Carbamazepine; Oxacarbazepine; Valporate; Maprotiline; Mirtazapine; Brofaromine; Gepirone; Moclobemide; isoniazid; iproniazid, and the like.

In certain embodiments (for example, for the treatment of ADD or ADHD), the neuropharmaceutical may be an ADHD medication such as a statin, amphetamine, Modafinil, Desoxyn, methamphetamine, cocaine, arecoline, Dexmethylphenidate (Focalin, Focalin XR), dextroamphetamine (Dexedrine, Dexedrine Spansules, Dextroamphetamine ER, Dextrostat), methylphenidate (Concerta, Daytrana, Metadate CD, Metadate ER, Methylin, Methylin ER, Ritalin, Ritalin-LA, Ritalin-SR), lisdexamfetamine dimesylate (Vyvanse), mixed salts amphetamine (Adderall, Adderall XR), Atomoxetine (Strattera), clonidine hydrochloride (Catapres), guanfacine hydrochloride (Tenex), arecoline, or Pemoline.

In certain embodiments (for example, for the treatment of a cognitive disorder, and/or a condition characterized by neurodegeneration, such Alzheimer's disease or Parkinson's disease) the neuropharmaceutical can be, for example, Donepezil, Tacrine, Rivastigmine, memantine (AXURA®, AKATINOL®, NAMENDA®, EBIXA®, ABIXA®), aricept, physostigmine, nicotine, arecoline, huperzine alpha, selegiline, Rilutek® (riluzole), Levodopa with carbidopa (SINEMET® or SINEMET CR®), Levodopa with benserazide (PROLOPA® or MADOPAR®), entacapone (COMTAN® or TASMAR®), dopamine agonists (such as pramiprexole (MIRAPEX®), ropinerole (REQUIP®), bromocriptine (PARLODEL®) and pergolide (PERMAX®), amantadine (SYMMETREL®), benztropine (COGENTIN®), trihexphenydil (ARTANE®), deprenyl (ELDEPRYL®), and the like.

Certain embodiments of the invention provide for combination therapies in which a subject is administered govadine or a compound of formula (I) in conjunction with a drug commonly used to treat addiction, such as methadone, naltrexone, buprenorphine, acamprosate, ibogaine, topiramate, baclofen or modafinil. Combination of administration of a compound of general formula (I) with other treatments modalities, such as counseling and other behavioural therapies, for the treatment of addiction is also contemplated.

Kits

The present invention additionally provides for therapeutic kits containing govadine or one or more compounds of formula I, or pharmaceutical compositions comprising same. In those embodiments in which the compounds provided by the kit are intended for use as part of a combination therapy, the kit may optionally contain the other therapeutic(s) that makes up the combination. In certain embodiments, one or more of the components of the kit can be lyophilized and the kit can additionally contain a suitable solvent for reconstitution of the lyophilized components. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, for use or sale for human or animal administration.

In certain embodiments, the compounds are provided in the kit in the form of pharmaceutical compositions suitable for administration to a subject. In this case, if desired, the container may itself be an inhalant, syringe, pipette, eye dropper, or other such like apparatus, from which the composition may be administered to the subject.

To gain a better understanding of the invention described herein, the following examples are set forth. It will be understood that these examples are intended to describe illustrative embodiments of the invention and are not intended to limit the scope of the invention in any way.

EXAMPLES

Preparation of Compounds:

Materials

Tetrahydrofuran, diethyl ether, dichloromethane and benzene were purified using the MBRAUN MB-SPS solvent purification system. Thin layer chromatography (TLC) was performed on Whatman Partisil K6F UV$_{254}$ pre-coated TLC plates. All chemicals were purchased from commercial sources and used as received.

Instrumentation

Proton nuclear magnetic resonance ($^1$H NMR) spectra were recorded in deuterochloroform using a Bruker AV-300 or AV-400 spectrometer. Carbon nuclear magnetic resonance ($^{13}$C NMR) spectra were recorded in deuterochloroform or CD$_3$OD using a Bruker AV-400 spectrometer. Chemical shifts are reported in parts per million (ppm) and are referenced to the centerline of deuterochloroform (7.27 ppm $^1$H NMR; 77.0 ppm $^{13}$C NMR) or CD$_3$OD (3.31 ppm $^1$H NMR; 49.0 ppm $^{13}$C NMR). Low resolution mass spectra (LRMS) and high resolution mass spectra (HRMS) were recorded on either a Bruker Esquire-LC spectrometer (for LRMS) or a Waters/Micromass LCT spectrometer (for HRMS). Optical rotations were recorded with a Perkin-Elmer 241 polarimeter.

Example 1

Preparation of D-Govadine

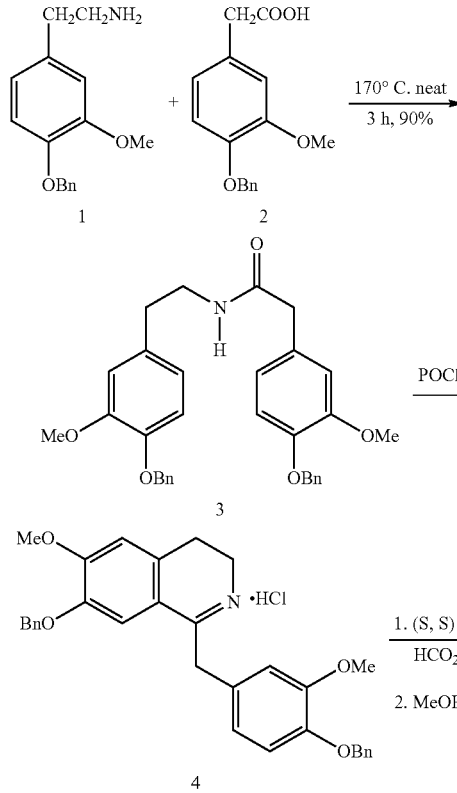

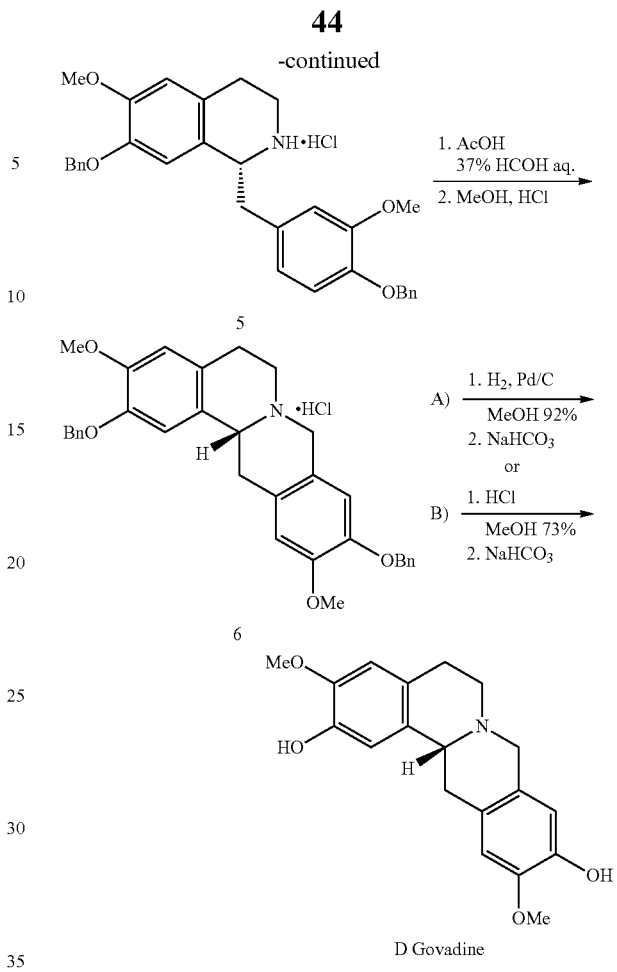

a) Synthesis of Amide 3:

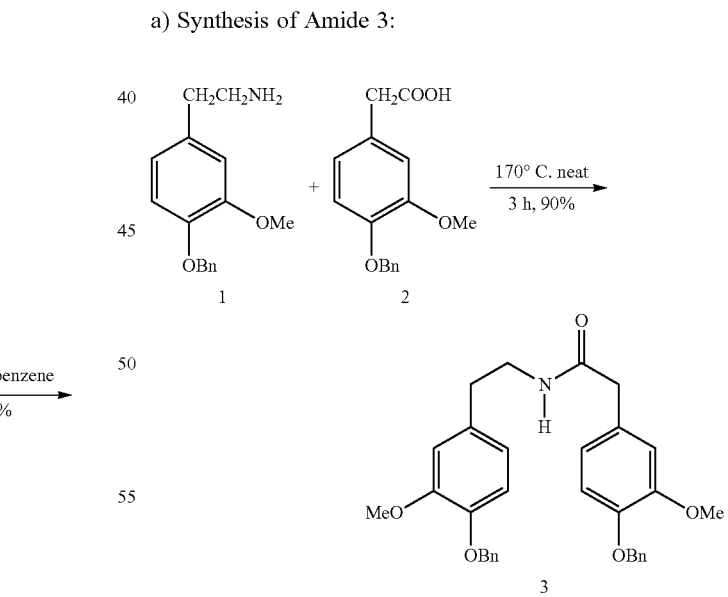

An intimate mixture of 10.88 g (40.0 mmol) of carboxylic acid 2, and 10.28 g (40.0 mol) of amine 1, contained in a 100 mL flask was evacuated and refilled with nitrogen. The flask was placed in an oil bath at 170° C. while passing a slow continuous stream of argon over the solid. When the solid had completely melted, the mixture was heated for 3.0 h while passing nitrogen over the melt to sweep out the H$_2$O formed. The melt was cooled to room temperature, and the residue was dissolved in CH$_2$Cl$_2$ (180 mL). The solution was washed with saturated aqueous NaHCO$_3$ (2×50 mL), aqueous HCl (10%, 2×40 mL), and brine (80 mL). The organic layer was dried over Na$_2$SO$_4$, filtered and concentrated by rotary evaporation to provide a yellow solid, which was recrystallized from hot ethyl acetate to provide the amide 3 (19.04 g, 90%) as a white solid. Mp: 118-120° C. (Lit.[1] mp: 129-130.5° C.). IR (neat) 2930, 2859, 2096, 1655 cm$^{-1}$; $^1$H NMR (400 MHz, CDCl$_3$) δ 7.48-7.29 (m, 10 H), 6.81 (d, J=8.4 Hz, 1 H), 6.73 (d, J=8.0 Hz, 1 H), 6.70 (d, J=1.6 Hz, 1 H), 6.65 (d, J=1.6 Hz, 1 H), 6.68 (dd, J=8.0, 1.6 Hz, 1 H), 6.45 (dd, J=8.0, 1.6 Hz, 1 H), 5.42 (s, br, 1 H), 5.14 (s, 2 H), 5.12 (s, 2 H), 3.84 (s, 3 H), 3.80 (s, 3 H), 3.46 (s, 2 H), 3.44 (t, J=6.8 Hz, 2 H), 2.66 (t, J=6.8 Hz, 2 H); $^{13}$C NMR (100 MHz, CDCl$_3$) δ 171.2, 149.9, 149.7, 147.4, 146.8, 137.2, 137.0, 131.7, 128.54, 128.48, 127.9, 127.8, 127.2, 121.5, 120.6, 114.3, 114.1, 112.9, 112.3, 71.0, 55.9, 43.4, 40.6, 34.9.

b) Synthesis of Imine Salt 4:

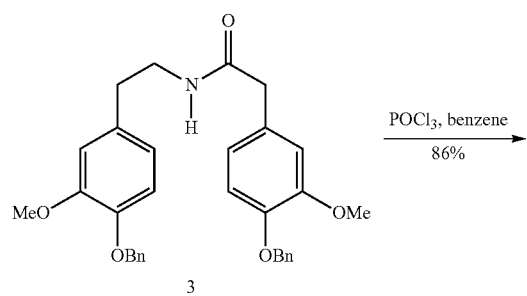

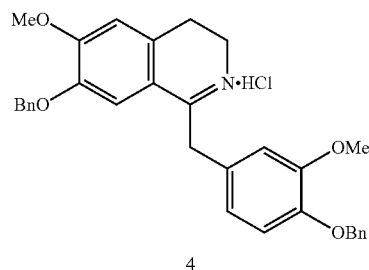

To a solution of the amide 3 (7.665 g, 15.0 mmol) in dry benzene (100 mL) was added POCl$_3$ (5 mL) then the mixture was refluxed for 2 h under nitrogen. The reaction mixture was cooled to room temperature and concentrated under vacuum. The residue was washed with petroleum ether (2×30 mL) and re-crystallized from MeOH/diether ether to afford the imine as the HCl salt 4 (6.84 g, 86%). Mp: 190-191° C. (lit.[1] Mp: 195-198° C.). IR (neat) 2930, 2859, 2096, 1655, 1257 cm$^{-1}$; $^1$H NMR (400 MHz, CDCl$_3$) δ 7.42-7.29 (m, 10 H), 7.21 (d, J=1.6 Hz, 1 H), 6.78 (s, 1 H), 6.62 (d, J=8.4 Hz, 1 H), 6.34 (dd, J=8.0, 1.6 Hz, 1 H), 5.11 (s, 2 H), 5.08 (s, 2 H), 4.37 (s, 2 H), 3.98 (s, 3 H), 3.88 (s, 3 H), 3.94-3.84 (m, 2 H), 2.96 (t, J=8.0 Hz, 2 H); $^{13}$C NMR (100 MHz, CDCl$_3$) δ 174.2, 156.8, 150.3, 147.7, 147.4, 136.9, 135.7, 134.1, 128.9, 128.5, 128.4, 127.8, 127.1, 126.9, 126.1, 120.9, 117.1, 115.0, 114.4, 113.1, 111.3, 71.4, 71.0, 56.50, 56.48, 40.7, 3737, 25.4.

c) Synthesis of Amine Salt 5:

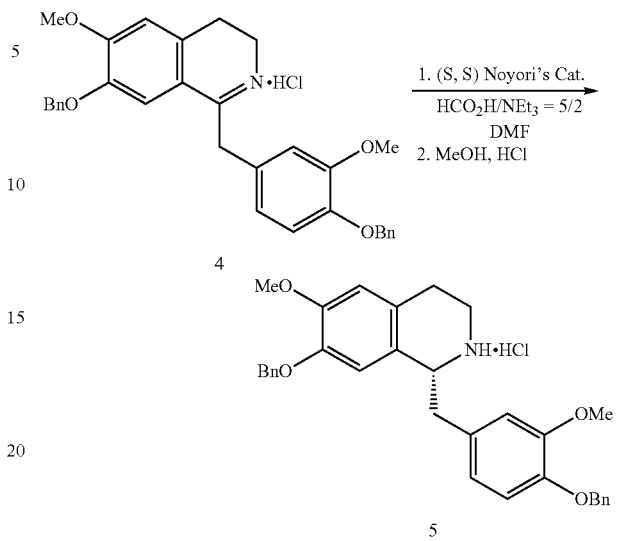

Imine salt 4 (3.174 g, 6 0 mmol) was suspensed in CH$_2$Cl$_2$ (100 mL), and washed with saturated aqueous NaHCO$_3$ (2×30 mL), brine, dried over MgSO$_4$, filtered and concentrated by rotary evaporation to provide a yellow solid. The free imine was dissolved in dry DMF (25 mL) and the solution was degassed for 15 min with nitrogen. RuCl[(S,S)-TsDPEN(P-cymene)] (38 mg, 1 mol %) was added followed by a 5:2 mixture of formic acid/triethylamine (5.0 mL), and the reaction mixture was stirred at room temperature for 9 h under nitrogen. The reaction was quenched with saturated aqueous NaHCO$_3$ (100 mL) and extracted with ethyl acetate (3×50 mL). The combined organic layers were washed with brine, dried over Na$_2$SO$_4$, filtered, and concentrated. The crude greenish product is reasonably pure, but unstable at room temperature. The crude greenish product was therefore converted into its HCl salt by treatment with conc. HCl-MeOH-diether ether solution at −20° C. to afford compound 5 as light greenish solid (2.59 g, 81%). Mp: 141-143° C. $^1$H NMR (400 MHz, CDCl$_3$) δ 10.18 (s, br, 1 H), 9.76 (s, br, 1 H), 7.45-7.20 (m, 10 H), 6.76 (d, J=8.4 Hz, 1 H), 6.73 (s, 1 H), 6.56 (s, 2 H), 5.09 (s, 2 H), 4.84 (d, J=12.4 Hz, 1 H), 4.73 (d, J=12.4 Hz, 1 H), 4.64 (s, br, 1 H), 3.84 (s, 3 H), 3.77 (s, 3 H), 3.44 (d, J=11.6 Hz, 1 H), 3.34-3.23 (m, 1 H), 3.20-3.05 (m, 3 H), 2.92-2.79 (m, 1 H); $^{13}$C NMR (100 MHz, CDCl$_3$) δ 149.7, 149.3, 147.4, 146.6, 137.0, 136.6, 128.54, 128.52, 128.4, 127.91, 127.87, 127.3, 127.1, 124.2, 122.7, 122.2, 114.0, 113.6, 112.5, 111.7, 71.0, 70.7, 56.1, 56.0, 54.8, 40.5, 38.7, 25.1.

d) Synthesis of Tetrahydroprotoberberine 6:

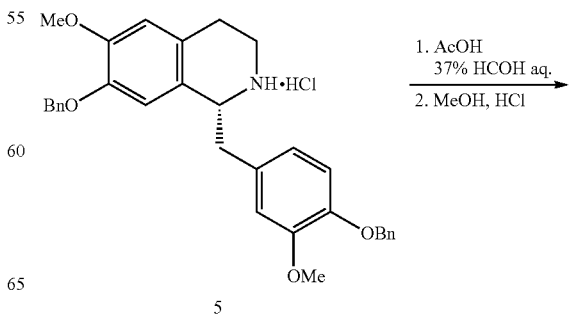

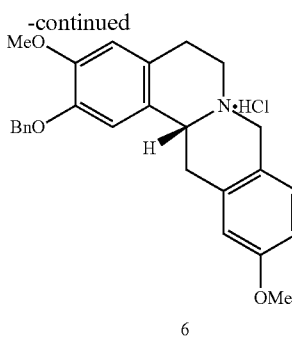

6

A mixture of aqueous CH₂O (12.0 mL, c=37%), HOAc (12.0 mL), and amine salt 5 (2.59 g, 4.71 mmol) was heated to 90° C. for 4 h. The reaction mixture was cooled to room temperature and concentrated to about 10 mL under reduced pressure and saturated aqueous NaHCO₃ was added until pH>7 was reached. The mixture was then extracted with CH₂Cl₂ (3×40 mL). The combined organic layers were washed with saturated aqueous NaHCO₃ (2×30 mL), water (30 mL), brine (30 mL), dried with MgSO₄ and the solvent was evaporated under vacuum. The crude yellow product was dissolved in MeOH and conc. HCl (1 mL) was added followed by adding diethyl ether. The solution was kept in the freezer to afford light yellow solid as HCl salt (2.12 g, 80%). Mp: 212-214° C. [α]$_D^{22}$=+145 (c 0.88, CHCl3). ¹H NMR shows broad peaks. Its free amine was characterized. [α]$_D^{22}$=+167 (c=0.90, CHCl3). IR (neat) 2822, 1610, 1505, 1257 cm-1; 1H NMR (400 MHz, CDCl3) δ 7.55-7.31 (m 10 H), 6.81 (s, 1 H), 6.69 (s, 1 H), 6.68 (s, 1 H), 6.63 (s, 1 H), 5.18 (s, 2 H), 5.16 (s, 2 H), 3.91 (s, 6 H), 3.96-3.84 (m, 1 H), 3.63 (d, J=14.4 Hz, 1 H), 3.54 (dd, J=10.8, 3.2 Hz, 1 H), 3.22-3.08 (m, 3 H), 2.77 (dd, J=15.6, 11.6 Hz, 1 H), 2.75-2.57 (m, 2 H); 13C NMR (100 MHz, CDCl3) δ 148.4, 148.3, 146.5, 137.3, 137.2, 129.7, 128.49, 128.46, 127.8, 127.7, 127.54, 127.47, 127.2, 127.0, 126.3, 112.08, 112.05, 112.0, 111.9, 71.6, 71.2, 59.4, 58.1, 56.1, 56.0, 51.3, 36.3, 23.0.

e) Synthesis of D-Govadine 53:

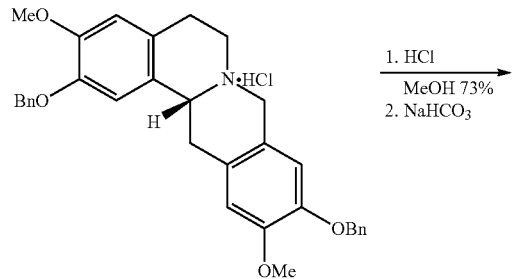

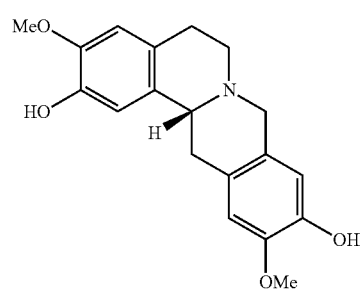

53

Compound 6 (1.422 g, 2.01 mmol) was refluxed in a mixture of concentrated hydrochloric acid (30 mL) and methanol (10 mL) for 2 h under nitrogen atmosphere. The reaction mixture was cooled to 0° C. and basified with concentrated ammonia solution (30 mL). The mixture was extracted with CH₂Cl₂. The combined organic layer was washed with brine, dried over Na₂SO₄, filtered, and concentrated to give the crude product, which was purified by column chromatography (CH₂Cl₂/CH₃OH=50/1) to yield 616 mg of the title compound (72%, >99% ee). Mp: 208-209° C. [α]$_D^{25}$=300 (c 0.5, EtOH). IR (neat) 3500, 2800, 1510, 1203 cm⁻¹; ¹H NMR (400 MHz, CDCl₃) δ 6.85 (s, 1 H), 6.65 (s, 2 H), 6.62 (s, 1 H), 5.52 (s, br, 2 H), 3.90 (s, 3 H), 3.89 (s, 3 H), 3.67 (d, J=14.4 Hz, 1 H), 3.60 (dd, J=11.2, 3.2Hz, 1 H), 3.25 (dd, J=16.0, 3.6 Hz, 1 H), 3.23-3.12 (m 2 H), 2.86 (dd, J=15.6, 11.6 Hz, 1 H), 2.75-2.60 (m 2 H). ¹³C NMR (100 MHz, CDCl₃) δ 145.3, 145.1, 143.9, 143.8, 130.5, 126.9, 126.0, 125.7, 111.8, 111.3, 110.7, 110.6, 59.5, 58.1, 56.0, 55.9, 51.4, 36.3, 29.0.

Example 2

Alternative Methods of Preparing Amide 3

Known peptide couplings between dopamine derivative 1 and homovanillic acid derivative 21 were investigated to determine which conditions provided the highest yields and which could be purified by crystallization. The results are shown in Table 1 below.

Conversion of carboxylic acid 21a to the corresponding acid chloride 21b using thionyl chloride was first explored, followed by coupling with amine 1 (Entry 1 in Table 1). This protocol only afforded modest yields (50-60%) of amide 3 and the reaction was not clean, thus necessitating purification by flash column chromatography. Peptide coupling using DCC and hydroxysuccinimide provided amide 3 in a slightly lower yield (40-50%), but the product could still not be isolated cleanly by crystallization (Entry 2). Next a thermal peptide coupling between amine 1 and acid 21a (Entry 3). Although these conditions have never been explored with either 1 or 21a, they have been demonstrated to be successful when coupling comparable dopamine and homovanillic acid derivatives. Gratifyingly, heating the two species neat at 180° C. provided clean conversion to the desired coupled product, which could readily be purified by re-crystallization. Thermal peptide couplings were also attempted using a microwave reactor, but there was significant decomposition (Entry 4).

TABLE 1

Preparation of Amide 3

| Entry | Homovanillic Acid Derivative | Conditions | Yield (%) |
|---|---|---|---|
| 1 | 21b | NEt₃, DCM | 59[a] |
| 2 | 21a | DCC, N-hydroxysuccinamide, DCM | 46[a] |
| 3 | 21a | Neat, 170° C. | 90[b] |
| 4 | 21a | μW, 170° C., DMSO | nd |

Example 3

Preparation of L-Govadine

L-Govadine was prepared following the synthetic route described in Example 1 but employing the opposite enantiomer of the Noyori catalyst. The overall yield was 39% and produced l-govadine with a >99% ee. Mp: 208-210° C. [α]D25=−301 (c 0.4, EtOH). IR (neat) 3500, 2800, 1510, 1203 cm−1; 1H NMR (400 MHz, CDCl3) δ 6.85 (s, 1 H), 6.65 (s, 2 H), 6.62 (s, 1 H), 5.52 (s, br, 2 H), 3.90 (s, 3 H), 3.89 (s, 3 H), 3.67 (d, J=14.4 Hz, 1 H), 3.60 (dd, J=11.2, 3.2Hz, 1 H), 3.25 (dd, J=16.0, 3.6 Hz, 1 H), 3.23-3.12 (m 2 H), 2.86 (dd, J=15.6, 11.6 Hz, 1 H), 2.75-2.60 (m 2 H). 13C NMR (100 MHz, CDCl3) δ 145.3, 145.1, 143.9, 143.8, 130.5, 126.9, 126.0, 125.7, 111.8, 111.3, 110.7, 110.6, 59.5, 58.1, 56.0, 55.9, 51.4, 36.3, 29.0.
Example 4
Synthesis of Racemic Govadine
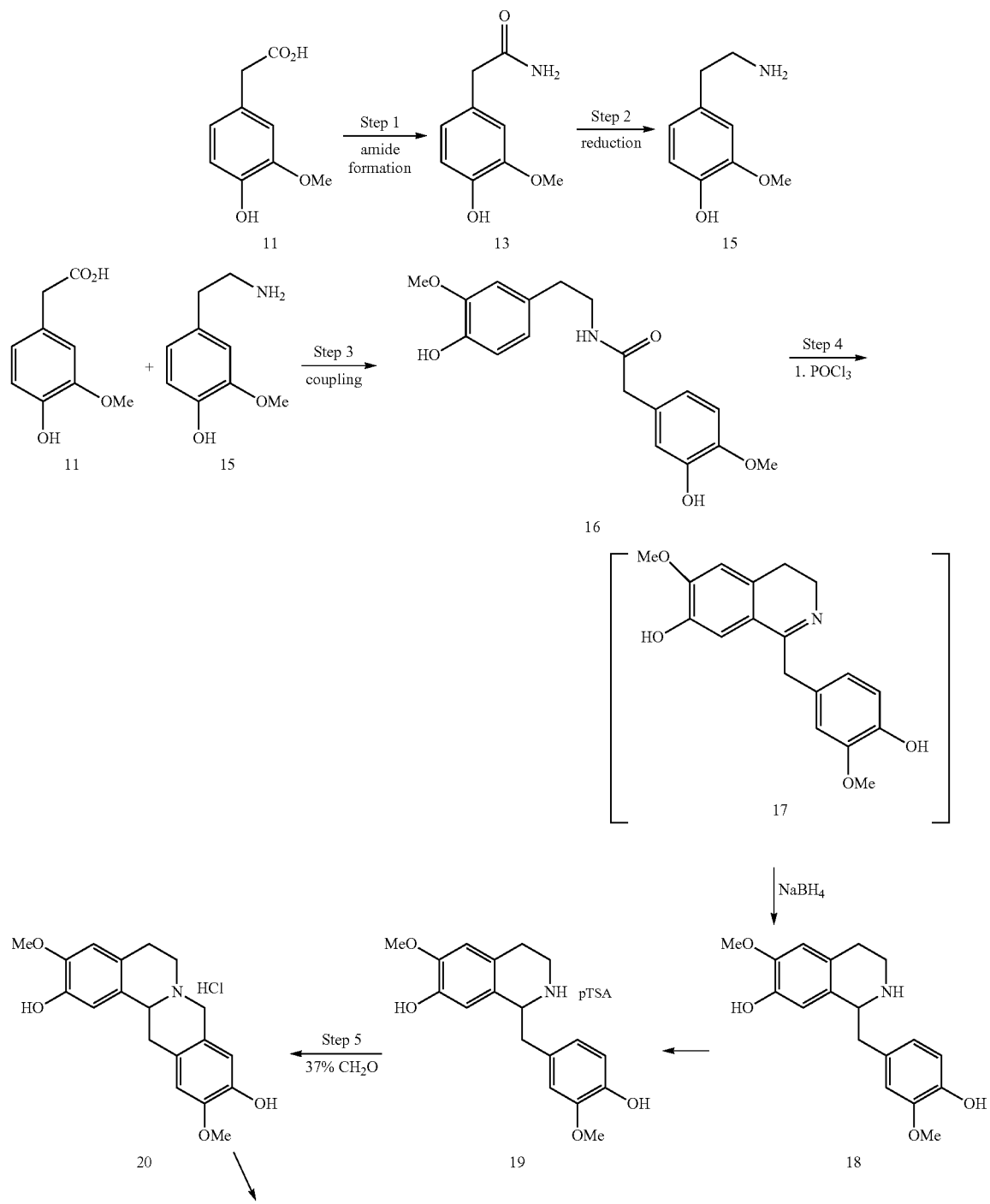

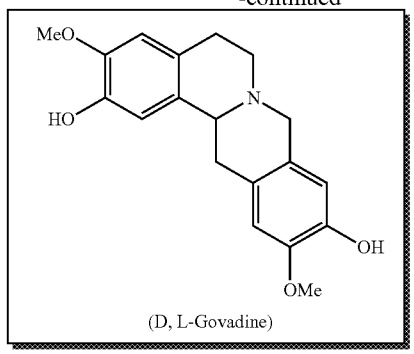

(D, L-Govadine)

a) Preparation of 2-(4-hydroxy-3-methoxyphenyl)acetamide 13:

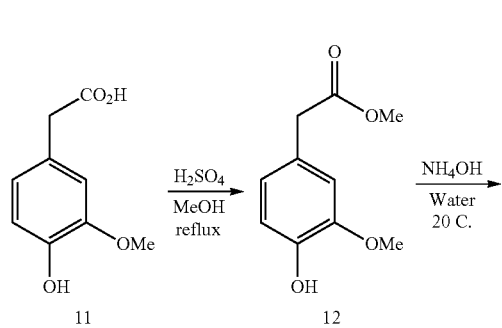

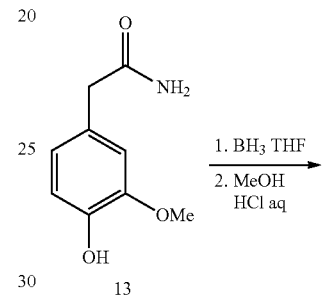

Sulfuric acid (5.8 mL, 0.11 mol) was added to a homogeneous solution of homovanillic acid 11 (400 g, 2.2 mol) in methanol (2.0 L) at room temperature. The solution was heated to reflux and stirred for 4 hours. The solvent was removed in vacuo to furnish the methyl ester as a viscous brown oil which was used directly in the subsequent step. $^1$H NMR (CDCl$_3$) δ 6.87-6.77 (m, 3H), 3.89 (s, 3H), 3.69 (s, 3H), 3.55 (s, 2H).

The methyl ester was added dropwise to concentrated ammonium hydroxide (1.53 L, 11 mole) at 10-15° C. over 75 minutes. The resulting slurry was warmed to room temperature and stirred for 3 days. Vacuum filtration afforded a clay-like product which was azeotroped to dryness three times with 1L portions of 2-methyltetrahydrofuran. Charged anhydrous tetrahydrofuran (1.0 L) and stirred for 1 hr at room temperature. Vacuum filtered and dried on the filter under nitrogen to furnish orange solid 2-(4-hydroxy-3-methoxyphenyl)acetamide 13 (293 g, 74% yield). $^1$H NMR (CDCl$_3$) δ 6.90-6.73 (m, 3H), 5.84 (br, 2H), 5.50 (br, 1H), 3.88 (s, 3H), 3.50 (s, 2H).

b) Preparation of 3-methoxytyramine 15:

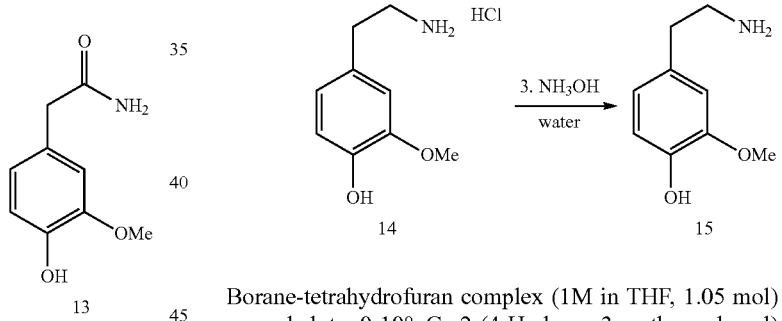

Borane-tetrahydrofuran complex (1M in THF, 1.05 mol) was cooled to 0-10° C. 2-(4-Hydroxy-3-methoxyphenyl)acetamide 13 (39.7 g, 0.219 mol) was added in small portions as a solid over 20 minutes while maintaining the temperature below 10° C. The reaction mixture was warmed to reflux and aged 8 hours. After cooling to room temperature, the reaction mixture was quenched with methanol (100 mL). Concentrated the reaction mixture to dryness in vacuo. Charged hydrochloric acid (37% aq., 79 mL), then heated back to reflux for 3 hours. Cooled the mixture to 0° C. Vacuum filtered to afford the amine hydrochloride salt 14 as a tan solid (54.2 g, 122% yield). $^1$H NMR (DMSO-d$_6$) δ 8.10 (br, 3H), 6.85-6.64 (m, 3H), 3.79 (s, 3H), 2.99 (m, 2H), 2.81 (m, 2H). Without drying, the hydrochloride salt was dissolved in water (90 mL) at 60-70° C. Ammonium hydroxide (17 mL, 0.127 mol) was added to the solution at 50° C. until a pH of 9-10 was acheived. Cooled to 0° C., vacuum filtered and washed with cold water (2×20 mL). Dried at room temperature under nitrogen to afford the amine freebase 15 (21.5 g, 59% yield from 2-(4-hydroxy-3-methoxyphenyl) acetamide). $^1$H NMR (MeCN-d3) δ 6.82-6.64 (m, 3H), 3.84 (s, 3H), 2.94 (br, 3H), 2.83 (t, J=7.14 Hz, 2H), 2.62 (t, J=6.96 Hz, 2H).

c) Preparation of amide 16:

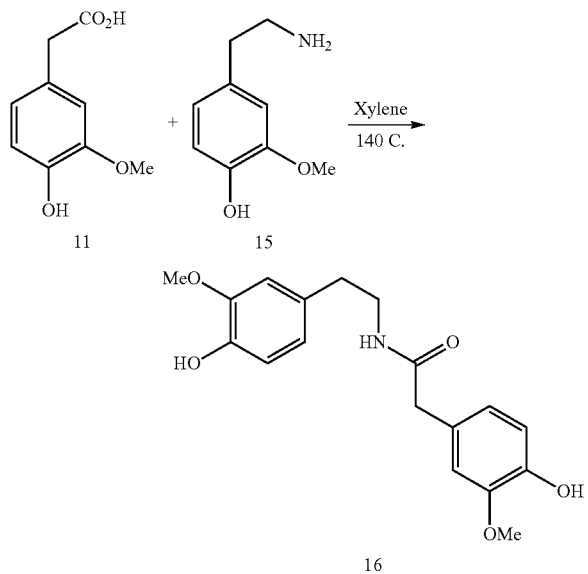

Homovanillic acid 11 (23.3 g, 0.128 mol) and 3-methoxy-tyramine 13 (21.4 g, 0.128 mol) were combined and heated to 200° C. under a nitrogen purge for 4 hours. Cooled the melt to room temperature to afford a brown tar which was used directly in the subsequent step. $^1$H NMR (MeCN-d3) δ 6.81-6.56 (m, 6H), 6.26 (br, 1H), 3.82 (s, 3H), 3.81 (s, 3H), 3.35 (t, J=6.96 Hz, 2H), 3.33 (s, 2H), 2.65 (t, J=6.96 Hz, 2H).

d) Preparation of 6-methoxy-1-vanillyl-1,2,3,4-tetrahydro-isoquinolin-7-ol 19:

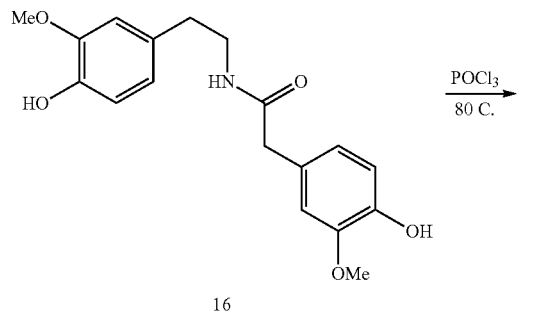

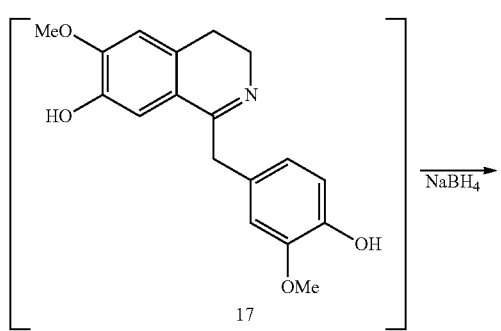

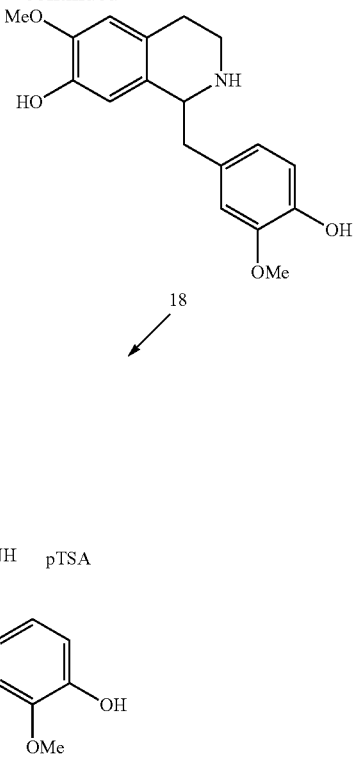

The crude amide 16 (40 g, 0.12 mol) was stirred with dichloromethane (600 mL). Charged phosphorus oxychloride (72 ml, 0.77 mol) and the mixture was purged with nitrogen. Heated to reflux and stirred 16 hrs, then evaporated the solvent and excess phosphorus oxychloride under nitrogen. Charged water (200 mL) over 10 minutes, then heated to reflux for 2 hrs resulting in a yellow slurry. Charged tetrahydrofuran (200 mL) and cooled to 0° C. while purging sub-surface with nitrogen. Adjusted the pH to 9 with concentrated ammonium hydroxide (80 mL). Charged sodium borohydride (3.6 g, 0.095 mol) and stirred under nitrogen at 0° C. for 1 hour. Warmed to 20° C. and stirred for another 16 hours. Extracted with dichloromethane (3×400 mL), then dried over anhydrous sodium sulfate, filtered and concentrated to give the amine freebase 18 as a pale yellow foam (32.0 g, 84% yield). $^1$H NMR (CDCl$_3$) δ 6.81-6.67 (m, 4H), 6.53 (s, 1H), 4.02 (dd, J=9.9, 4.0 Hz, 1H), 3.81 (s, 3 H), 3.80 (s, 3H), 3.19-3.08 (m, 2H), 2.88-2.61 (m, 4H).

Charged the amine freebase 18 (32.0 g, 0.10 mol), p-toluenesulfonic acid monohydrate (18.5 g, 0.097 mol) and heated to reflux in water (200 mL) and isopropanol (50 mL) to afford a fluid slurry. Cooled to 0° C., then filtered, washed with cold water (20 mL) and dried under nitrogen at 20° C. to give B371 pTSA salt 19 as a yellow solid (29.3 g, 50% yield). $^1$H NMR (Acetone-d6/D2O) δ 7.67 (d, J=8.2, 2H), 7.16 (d, J=7.9, 2H), 6.96 (s, 1H), 6.79 (m, 3H), 6.75 (s, 1H), 4.74 (dd, J=8.3, 5.4 Hz, 1H), 3.62-3.54 (m, 1H), 3.45-3.34 (m, 2H), 3.13-2.93 (m, 3H), 2.32 (s, 3H).

e) Pictet-Spengler Cyclization of Compound 19 to Form Compound 20:

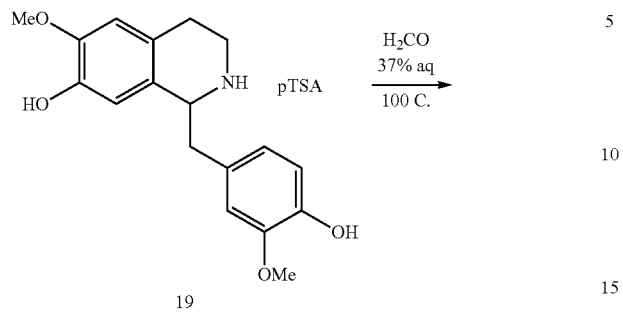

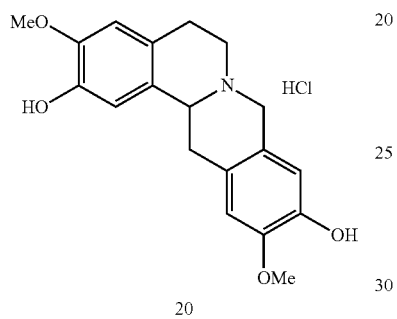

The salt 19 (27.3 g, 56 mmol) was heated to reflux for 5 hours in aqueous formaldehyde (13.6 mL, 185 mmol) and methanol (16.4 mL). Cooled to 20° C. and charged water (225 mL) and dichloromethane (750 mL). Adjusted the pH to 9 with concentrated ammonium hydroxide (11.5 mL). Warmed to ~35° C. and split phases, then extracted the aqueous with dichloromethane (6×250 mL). Combined the organic phases, dried over sodium sulphate and concentrated to give the crude freebase (17.85 g, 98% yield). Charged water (500 mL) then acidified with concentrated hydrochloric acid (5.8 mL, 70 mmol). Heated to reflux for 2 hours. Cooled to 0° C., filtered and washed with cold water (2×20 mL) and dried to afford compound 20 (18.4 g, 90% yield). $^1$H NMR (MeOD-d$_4$) δ 6.90 (s, 1H), 6.87 (s, 1H), 6.84 (s, 1H), 6.69 (s, 1H), 4.74 (dd, J=11.8, 4.8 Hz, 1H), 4.51 (br, 2H), 3.90 (s, 6H), 3.85-3.66 (m, 2H), 3.55 (dt, J=11.9, 4.7 Hz, 1H), 3.34-3.25 (m, 1H), 3.08 (dd, J=17.3, 11.7 Hz, 2H).

f) Formation of d,l-govadine 54:

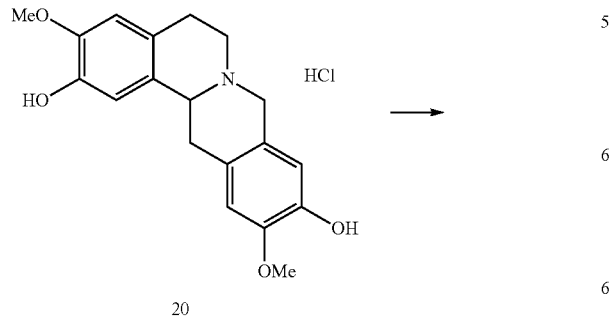

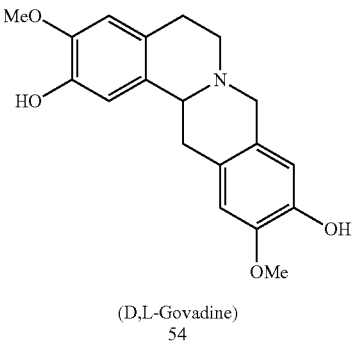

Govadine hydrochloride 20 (0.50 g, 1.37 mmol) was dissolved in water (15 mL) at 85-100° C. Charged ammonium hydroxide (0.25 mL, 1.79 mmol). After 1 hr at 85-100° C., cooled and held at 0° C. for 1 hr. Vacuum filtered and dried to afford d,l-govadine 54 (416 mg, 92% yield). $^1$H NMR (CDCl$_3$) δ 6.82 (s, 1H), 6.62 (s, 2H), 6.59 (s, 1H), 5.53 (br, 2H), 3.92-3.86 (m, 7H), 3.62 (d, J=14.6 Hz, 1H), 3.54 (dd, J=11.3, 3.7 Hz, 1H), 3.24-3.08 (m, 3H), 2.80 (dd, J=15.6, 11.3 Hz, 1H), 2.68-2.54 (m, 2H).

Example 5

Chiral Resolution of D,L-Tetrahydroprotoberbine

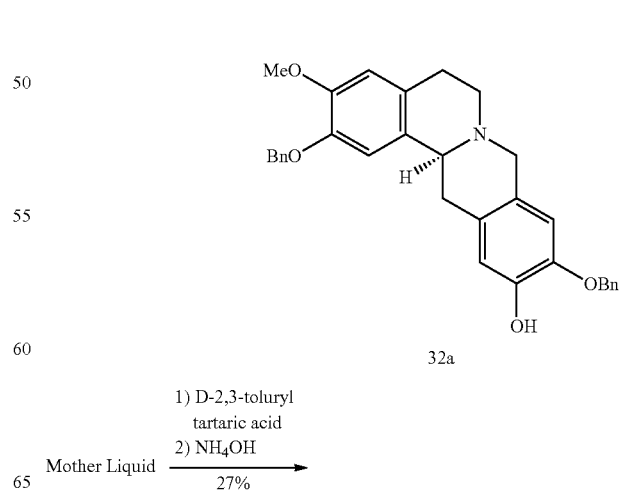

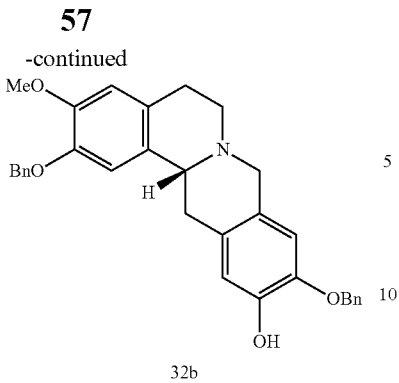

32b

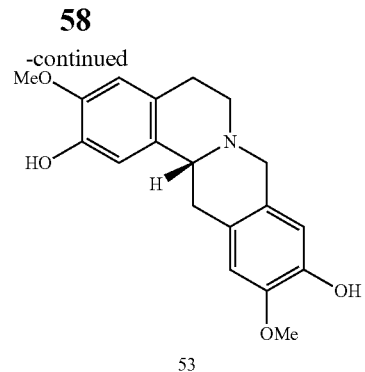

53

1.64 g of racemate amine 31 (3.33 mmol) in 50 mL of ethyl acetate was added 1.312 g (3.4 mmol) of 2,3-toluoyl-L-tartaric acid and refluxed for 4 h. The precipitated solid was filtered and recrystallized from MeOH/EtOAc to afford 960 mg white solid as the chiral salt. The salt was suspended in 40 mL of DCM and neutralized with aqueous ammonium. The organic layer was separated, dried over MgSO$_4$, filtered, and concentrated under reduced pressure to afford 486 mg (30%) of the L-amine 32a. The filtrate was washed with aqueous ammonium, dried over MgSO$_4$, filtered, and was added 1.158 g (3.0 mmol) of 2,3-toluoyl-D-tartaric acid and refluxed for 4 h. The precipitated solid was filtered and recrystallized from MeOH/EtOAc to afford 932 mg white solid as the chiral salt. The salt was suspended in 40 mL of DCM and neutralized with aqueous ammonium. The organic layer was separated, dried over MgSO$_4$, filtered, and concentrated under reduced pressure to afford 448 mg (27%) of the D-amine 32b.

Conversion of Compounds 32a and 32b to Govadine 53

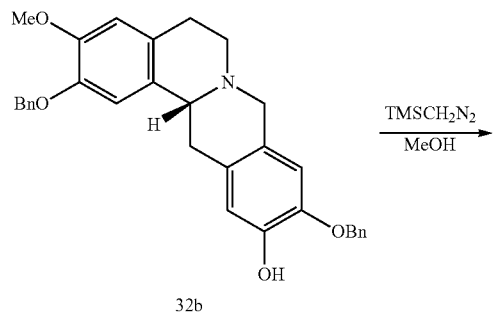

32b

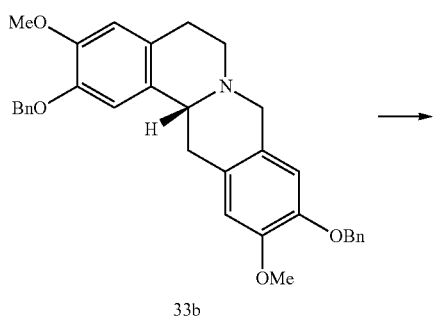

33b 32b (486 mg, 0.986 mmol) in MeOH (20 mL) was added 2.0 mL of TMSCH$_2$N$_2$ (1.0 M in hexane) dropwise over 5 min The yellow solution was stirred at room temperature for 40 h. The solvent was evaporated and the crude oil was purified by flash chromatography (hexanes:AcOEt=2:1, then hexanes:AcOEt=1:1) to afford 440 mg (95%) of the methylated compound (33b) as a yellow oil.

To a suspension of compound 33b (400 mg, 0.79 mmol) and 5% Pd—C (150 mg) in methanol (30 mL) was added 3 drops of concentrated hydrogen chloride aqueous solution and the mixture was stirred under hydrogen atmosphere for 4 h. After the Pd—C catalyst was filtered off through a pad of Celite, the filtrate was concentrated under reduced pressure. 40 ml of dichloromethane was added and the suspension was basified with saturated NaHCO$_3$ aqueous solution and the organic layer was washed with brine, dried over Na$_2$SO$_4$, filtered, and concentrated to give the crude product, which was purified by column chromatography (CH$_2$Cl$_2$/CH$_3$OH=50/1) to yield 238 mg of (+)-Govadine 53 (92%, >99% ee) as a light yellow solid. Mp: 208-209° C. $[\alpha]_D^{25}$ =+300 (c 0.5, EtOH). IR (neat) 3500, 2800, 1510, 1203 cm$^{-1}$; $^1$H NMR (400 MHz, CDCl$_3$) δ 6.85 (s, 1 H), 6.65 (s, 2 H), 6.62 (s, 1 H), 5.52 (s, br, 2 H), 3.90 (s, 3 H), 3.89 (s, 3 H), 3.67 (d, J=14.4 Hz, 1 H), 3.60 (dd, J=11.2, 3.2Hz, 1 H), 3.25 (dd, J=16.0, 3.6 Hz, 1 H), 3.23-3.12 (m 2 H), 2.86 (dd, J=15.6, 11.6 Hz, 1 H), 2.75-2.60 (m 2 H). $^{13}$C NMR (100 MHz, CDCl$_3$) δ 145.3, 145.1, 143.9, 143.8, 130.5, 126.9, 126.0, 125.7, 111.8, 111.3, 110.7, 110.6, 59.5, 58.1, 56.0, 55.9, 51.4, 36.3, 29.0.

Example 6

Receptor Binding Profile of D- and L-Govadine

The affinity of d- and l-govadine for dopamine and serotonin receptors was performed by MDS Pharma Services, Inc (King of Prussia, Pa.). All receptors tested were heterologously expressed CHO cells and IC50 values were determined by a non-linear, least squares regression analysis using MathIQ (ID Business Solution Ltd, UK). Ki was calculated using the equation of Cheng and Prusoff (1973, Biochem. Pharmacol 22:23099-3108) derived from the observed IC$_{50}$ of the tested compound, the concentration of radioligand employed in the assay, and the historical values for the Kd of the ligand (obtained experimentally at MDS Pharma Services).

The results of this experiment are shown in Table 2 and demonstrate that a different percentage of the two enantiomeric forms of govadine present different binding affinity to the D2 receptors. d-govadine presents strong binding affinity to the D1 receptor and weak affinity to the D2 receptor, whereas l-govadine presents strong affinity to both the D1 and D2 receptors.

TABLE 2

Receptor Binding for l- and d-Govadine (Ki in nM or % Inhibition at 10 μM)

| Receptor | l-Govadine | d-Govadine |
|---|---|---|
| 5HT1A | 15,200 | 18,200 |
| 5HT2A | 11,100 | 11,800 |
| 5HT2C | 45,200 | 46,500 |
| 5HT3 | 5% | −8% |
| 5HT4 | 2470 | 42% |
| 5HT6 | 12% | 9% |
| D1 | 5.77 | 8.75 |
| D2L | 165 | 1340 |
| D3 | 548 | 606 |
| D4.2 | 21% | 20% |
| D5 | 10.5 | 13.4 |

Example 7

Receptor Binding Profile of D- and L-Govadine: Functional Assay

Methods employed in this Example were adapted from Liu et al (1992, *Mol Endocrinol* 92:1815-1824) and Zhou et al (1990, *Nature* 347:76-79) to maximize reliability and reproducibility. Reference standards were run as an integral part of each assay to ensure the validity of the results obtained. Dopamine D1 receptors are generally known to couple only to Gs and increase cAMP production. The Dopamine D1 receptor Adenylyl Cyclase Cellular Assay for d- and l-govadine was performed by MDS Pharma Services, Inc (King of Prussia, Pa.). Dopamine D1 receptors were heterologously expressed CHO cells and test articles (d-govadine or l-govadine) were tested at concentrations that range from 10 mM to 1 nM. Basal levels of cAMP production were measured and compared to the levels of cAMP in response to d- and l-govadine treatment (incubation buffer HBSS, 5 mM HEPES, 0.1% BSA, 100 μM IBMX, pH7.4, for 30 minutes at 37° C.). (+)-Butaclamol was used as a positive control for the assay assessing antagonism. Homogeneous fluorescence methodology HTRF homogeneous fluorescence quantitation methodology was used to measure the levels of cAMP.

The criterion for significant agonist activity is ≥50% increase in cAMP relative to dopamine response. The criteria for significant antagonist activity ≥50% inhibition of dopamine-induced cAMP increase.

The results of this experiment are shown in Table 3. A significant antagonistic response was noted for d-govadine with an $IC_{50}$ of 2.38 mM and for l-govadine with an $IC_{50}$ of 0.0166 mM. The data suggest that, although differing in efficacy, both d- and l-govadine are only weak dopamine D1 receptor antagonists and would not be expected to function as cognitive enhancers.

TABLE 3

Receptor Binding of d- and l-Govadine

| | % Response | | |
|---|---|---|---|
| | Agonist | Antagonist | $IC_{50}/EC_{50}$ |
| d-govadine | 2 | 82 | 2.38 μM |
| l-govadine | 2 | 87 | 16.6 nM |

Example 8

Effect of D- and L-Govadine on Amphetamine-Induced Locomotion

Animals were habituated to the locomotor arena for 1 hr on 4 consecutive days prior to testing. Locomotor activity was assessed on day 1 of habituation and treatment groups were assigned in a counter balanced fashion depending on locomotor activity on this day.

Animals received IP injections of: 3.0 mg/kg d-govadine (N=8), 10.0 mg/kg d-govadine (N=6), 0.3 mg/kg l-govadine (N=6), 1.0 mg/kg l-govadine (N=6), 3.0 mg/kg l-govadine (N=6), 5.0 mg/kg clozapine (N=6), 10 mg/kg clozapine (N=6), 15 minutes before 1.5 mg/kg d-AMPH on day 5. After d-AMPH/SAL injection, distance travelled was assessed for 1 hr. Distance travelled was recorded with Noldus Ethovision XT (Noldus, Leesburg, Va.) and analyzed off-line.

Figure 2:
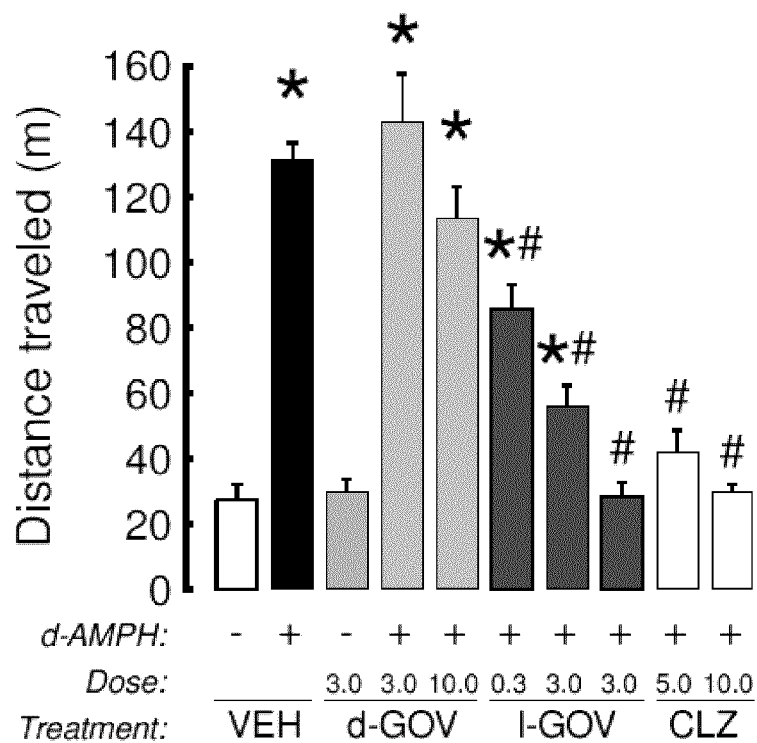
FIG. 2 presents the results of the analysis of amphetamine-induced locomotion in rats treated with d- or l-govadine: d-AMPH (black bars), pre-treatment with d-govadine (light gray bars), pre-treatment with l-govadine (dark gray bars), pre-treatment with clozapine (white bars) (control). All data are presented as the mean±SEM (*comparison with Saline+VEH, Tukey's post hoc, $p<0.05$; # comparison with d-AMPH+VEH, Tukey's post hoc, $p<0.05$).

The results are shown in FIG. 2. A robust increase in locomotion was observed with a 1.5 mg/kg dose of d-AMPH (black bars). Pre-treatment with d-govadine (light gray bars) was without effect whereas pre-treatment with l-govadine (dark gray bars) robustly suppressed amphetamine-induced locomotion (AIL). Injection of clozapine (white bars) completely ameliorated AIL. All data are presented as the mean±SEM (*comparison with Saline+VEH, Tukey's post hoc, p<0.05; # comparison with d-AMPH+VEH, Tukey's post hoc, p<0.05).

These data suggest that d-govadine is an unlikely candidate for effectively addressing the psychomotor abnormalities that characterize psychosis, whereas l-govadine would appear to address these pathologies and possess a pharmacological profile consistent with an antipsychotic.

Example 9

Effect of D- and L-Govadine on Conditioned Avoidance Responding

Conditioned avoidance responding (CAR) was performed in a two-way avoidance procedure with drug naive rats in four shuttle boxes (Med Associates, Vt., USA) each consisting of two compartments separated by an open door. Each compartment contained a wall-mounted speaker, house light and 5 photocells to detect the location of the animal. All experimental protocols and data acquisition were controlled by custom programs written in MED-PC.

Before training, each animal received two acclimation sessions lasting 30 min with only the house light illuminated. On the training day, rats were placed in the box 15 min before the trial commenced for acclimation. Pairings of the conditioned stimulus (CS) (white noise, ~60 dB) and the unconditioned stimulus (US) (footshock, 0.75 mA) were presented at random intervals with a mean of 60 sec. The CS was presented for 10 sec. During this time, if the animal moved to the opposite side of the box, the white noise was silenced, no foot shock delivered, and an avoidance response was scored. Upon termination of the 10 sec tone, if the animal had not moved to the opposite side of the box, a foot-shock was administered for 2 sec. Movement to the opposite compartment during this period resulted in termination of both the CS and US and an escape was scored. Failure to avoid or escape constituted a response failure and was scored accordingly. After reaching a criterion of 90% avoidances for a block of 20 trials, usually achieved with ~100 CS-US pairings, each animal advanced to the drug-testing phase. Animals not meeting the criterion by 120 pairings were excluded from the study.

On the subsequent drug-test day, animals were injected subcutaneously with either vehicle (N=8), 1.0 mg/kg d-govadine (N=6), 3.0 mg/kg d-govadine (N=6), 10.0 mg/kg d-govadine (N=6), 0.3 mg/kg l-govadine (N=6), 1.0 mg/kg l-govadine (N=7), 3.0 mg/kg l-govadine (N=6), or 5.0 mg/kg clozapine (N =8), then placed immediately into the 2 way-avoidance chamber with house lights illuminated. After 15 min of acclimation in the chamber, the CS-US pairings began. Pairings were presented just as during training and were scored in the same fashion. The test trial consisted of 100 CS-US pairings.

Figure 3:
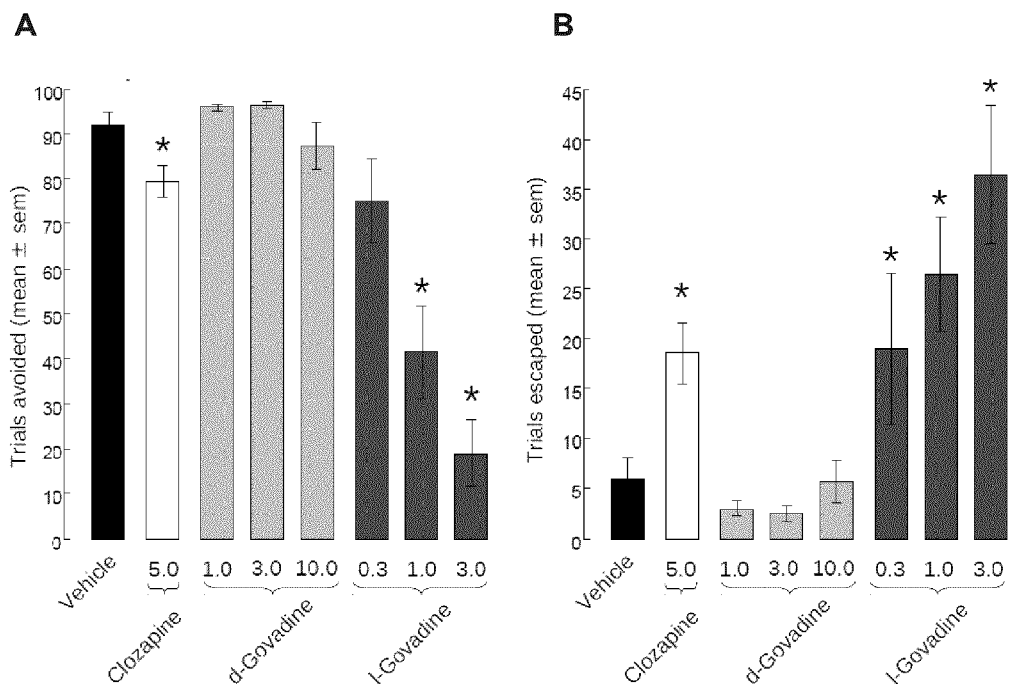
FIG. 3 presents the results of the analysis of conditioned avoidance responding in rats treated with d- or l-govadine: (A) shows the number of avoidances and (B) shows the number of escapes for animals treated with d-govadine (light gray bars), l-govadine (dark gray bars), and clozapine (white bar). (*comparison with VEH group, Tukey's post hoc, $p<0.05$).

The results are shown in FIG. 3. Suppression of conditioned avoidance responding was observed in l-govadine (dark gray bars) and clozapine (white bar) treated animals but not in d-govadine (light gray bars) treated animals. A decrease in avoidances was accompanied by an increase in escapes ruling out the possibility that this compound induced a motor impairment. (*comparison with VEH group, Tukey's post hoc, p<0.05).

These data suggest that l-govadine can be used as an antipsychotic due to its D2 antagonistic activity whereas d-govadine would be much less effective as an antipsychotic.

Example 10

Effect of D- and L-Govadine on Dopamine Levels in the Brain

On surgery day, rats (275-300 g) were anesthetized using 4% isoflurane (AErrane, Baxter Co., Toronto, Canada) mixed with oxygen, and then maintained with 1.5-2.5% isoflurane for the remainder of the surgery. Rats received subcutaneous injections of an analgesic (ketoprofen 0.05 mL or buprenorphine, 0.1 mL) and sterile saline (0.9% NaCl, ~3 mL). Once shaved and cleaned, the heads were secured in the stereotaxic frame in flat skull position for bilateral implantation of stainless steel microdialysis guide cannulae (19 gauge×15 mm) in the nucleus accumbens (NAc) (from bregma +1.7 mm anterior and ±1.1 mm medial; from dura −1.0 mm ventral) or medial prefrontal cortex (mPFC) (+3.0 mm anterior, ±0.6 mm medial; −1.0 mm ventral). All coordinates were determined using the atlas of Paxinos and Watson (1997, *The Rat Brain in Stereotaxic Coordinates*, Academic Press, London (ISBN 0 12 547623)). Rats were allowed to rest with heat support until they regained consciousness, and then given a one-week recovery period.

Microdialysis probes were assembled 1-2 days prior to microdialysis experiments. Probes were concentric in design, constructed from Filtral 12 AN69HF semi-permeable hollow fibres (2 mm length, 340 μm OD×4 mm, 65 kDalton molecular weight cut-off; Hospal, Neurnberg, Germany) and silica inlet-outlet lines (75/150 um ID/OD). Typical in vitro probe recoveries of external standard solutions at room temperature (21° C.) were: 12% for dopamine (DA), 9% for 3,4-dihydroxyphenylacetic acid (DOPAC) and 8% for 5-hydroxyindoleacetic acid.

The day prior to microdialysis experiments, probes were connected to an Instech dual-channel liquid swivel (Plymouth Meeting, Pa.) and flushed with artificial cerebrospinal fluid (aCSF). The aCSF consisted of a 10.0 mM sodium phosphate buffer with 147.0 mM NaCl, 3.0 mM KCl, 1.0 mM $MgCl_2$ and 1.2 mM $CaCl_2$ (pH 7.4). Following DA recovery tests, probes were implanted via the guide cannulae (dialysis membrane spanned −4.8 to −6.8 mm ventrally for NAc; −1.6 to −3.6 mm for mPFC). Rats remained in the testing chamber overnight (14-16 hr) with aCSF perfusing continuously through the probes at 1 μL/min In the morning, microdialysis samples were collected at 10 min intervals and assayed for DA, DOPAC, homovanillic acid (HVA) and 5-HIAA content. Once baseline levels were determined to be stable for four consecutive samples (less than 10% fluctuation), the drug treatment phase of each experiment was initiated.

Microdialysis samples were analyzed immediately after collection using high pressure liquid chromatography (HPLC) with electrochemical detection. Two systems were used, each consisting of an ESA 582 pump (Bedford, Mass., USA), a pulse damper (Scientific Systems Inc., State College, Pa.), a Rheodyne Inert manual injector (model 9125i, 20 μL injection loop; Rohnert Park, Calif.), a Tosoh Bioscience Super ODS TSK column (2 μm particle, 2 mm×10 mm; Montgomeryville, Pa.) and an Antec Leyden Intro Electrochemical detector and VT-03 flow cell with a Ag/AgCl reference electrode (Vapplied=+650 mV; Leyden, The Netherlands). The mobile phase [70 mM sodium acetate buffer, 40 mg/L EDTA and 50 mg/L of sodium dodecyl sulfate (adjustable), pH 4.0, 10% methanol] flowed through the system at 0.17 mL/min EZChrome Elite software (Scientific Software, Pleasanton, Calif.) was used to acquire and analyze chromatographic data.

Figure 4:
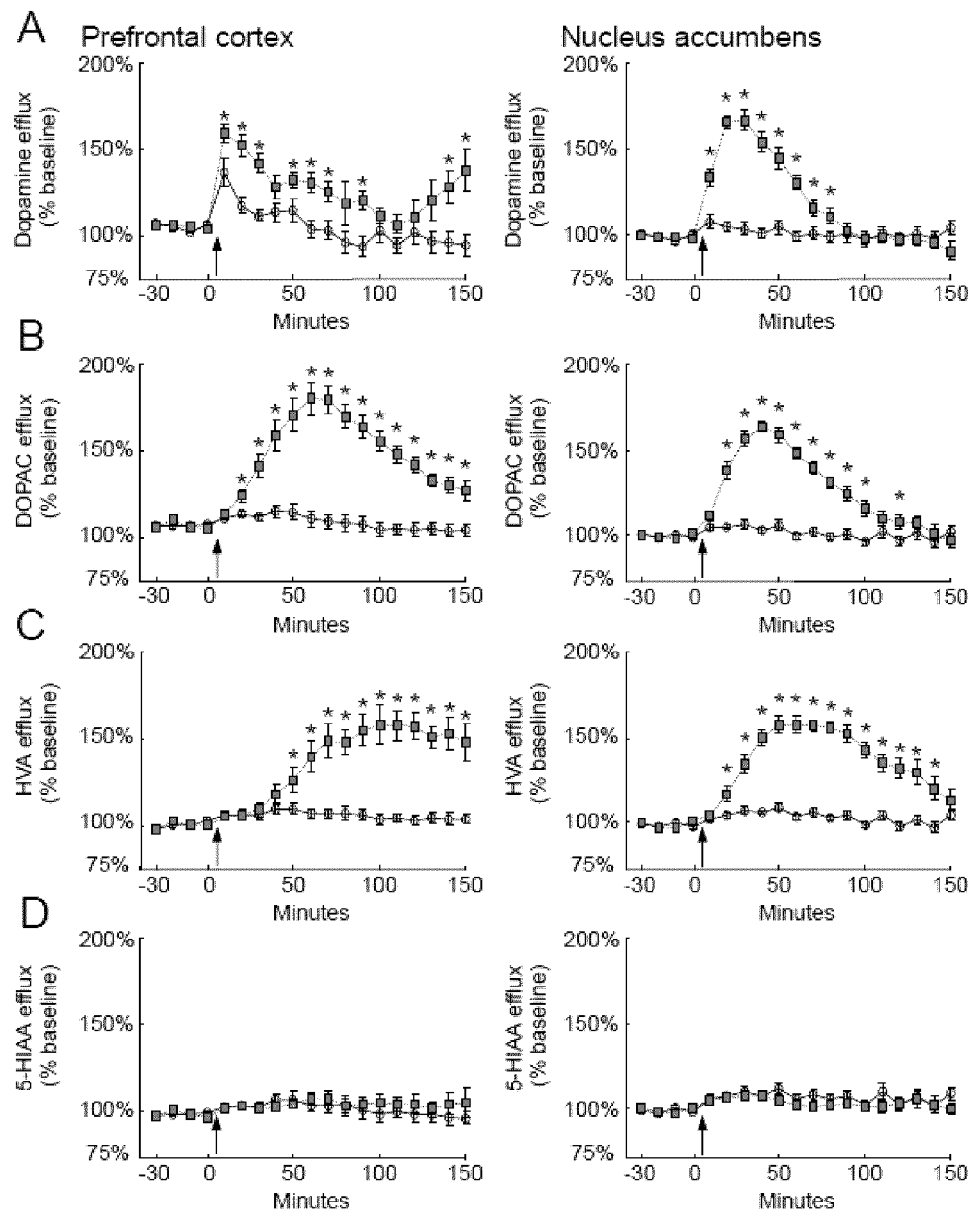
FIG. 4 presents the results of microdialysis analysis of levels of dopamine (A); 3,4-dihydroxyphenylacetic acid (DOPAC) (B); homovanillic acid (HVA) (C), and 5-hydroxyindoleacetic acid (5-HIAA) (D) in the prefrontal cortex and nucleus accumbens in rats treated with l-govadine.
Figure 5:
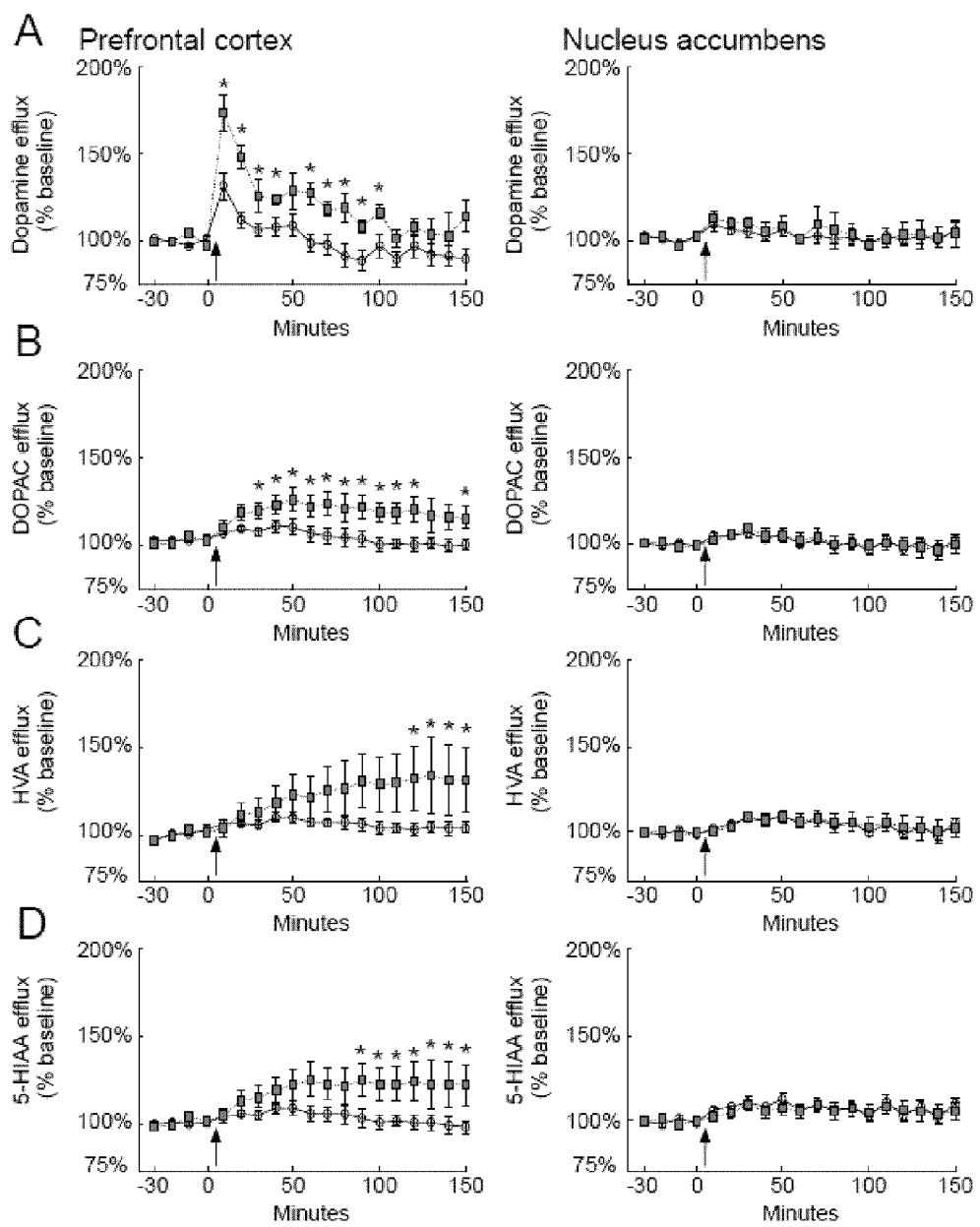
FIG. 5 presents the results of microdialysis analysis of levels of dopamine (A); 3,4-dihydroxyphenylacetic acid (DOPAC) (B); homovanillic acid (HVA) (C), and 5-hydroxyindoleacetic acid (5-HIAA) (D) in the prefrontal cortex and nucleus accumbens in rats treated with d-govadine.

The results are shown in FIG. 4 (l-govadine treated animals) and FIG. 5 (d-govadine treated animals). Injection with l-govadine increased dopamine levels in both the PFC and the NAc (FIG. 4: panel A). An increase in both dopamine metabolites, DOPAC and HVA, in the PFC and NAc was also observed (FIG. 4: panels B and C). No increase in the serotonin metabolite, 5-HIAA, was observed (FIG. 4: panel D). In contrast, injection with d-govadine selectively increased dopamine in the PFC but not in the NAc (FIG. 5: panel A). d-govadine also increased both dopamine metabolites, DOPAC and HVA, in the PFC, with no increase observed in the NAc (FIG. 5: panels B and C). In addition, d-govadine increased the serotinin metabolite, 5-HIAA, in the PFC but not the NAc (FIG. 5: panel D).

The results thus demonstrated the differential function of l- and d-govadine in inducing dopamine release in the prefrontal cortex and nucleus accumbens.

Example 11

Effect of D- and L-Govadine on Temporal Order Recognition

The task exploits a rat's natural preference for novel locations. Each animal received 3 separate trials where access to two arms of an eight arm radial arm maze was granted. During the first trial, two arms were selected at random for exploration, and animals were allowed to explore these arms for 2 min After this time, they were taken off the maze and returned to their home cage. 1 hour later they were placed back on the maze and two new arms were randomly selected for 2 min of exploration. At the conclusion of this 2 min, animals were again returned to their home cage for either a 45 min or 4 hr delay.

Animals were injected 15 min before the start of the third "test" trail (45 min delay: 1.0 mg/kg d-govadine (N=7), 1.0 mg/kg l-govadine (N=6), 5.0 mg/kg clozapine (CLZ) (N=8), vehicle (VEH) (N=7); 4 hour delay: 1.0 mg/kg d-govadine (N=6), 1.0 mg/kg l-govadine (N=8), 5.0 mg/kg CLZ (N=6), VEH (N=6) At the completion of the delay, one arm from the first trial and one arm from the second trial was opened and the animal was placed on the maze and allowed to freely explore. Time spent in each arm (recent and old) was recorded as well as total distance traveled and the total number of arm entries in Noldus EthoVision 3.1 (Leesburg, Va.). Temporal order recognition is expressed as an increase in the time spent "old" arm relative to the "new" (Hannessan et al., 2004, *J Neurosci.*, 24(19):4596-604; Hotte et al., 2005, *Neurobiol Learn Mem.* 84(2):85-92).

Figure 6:
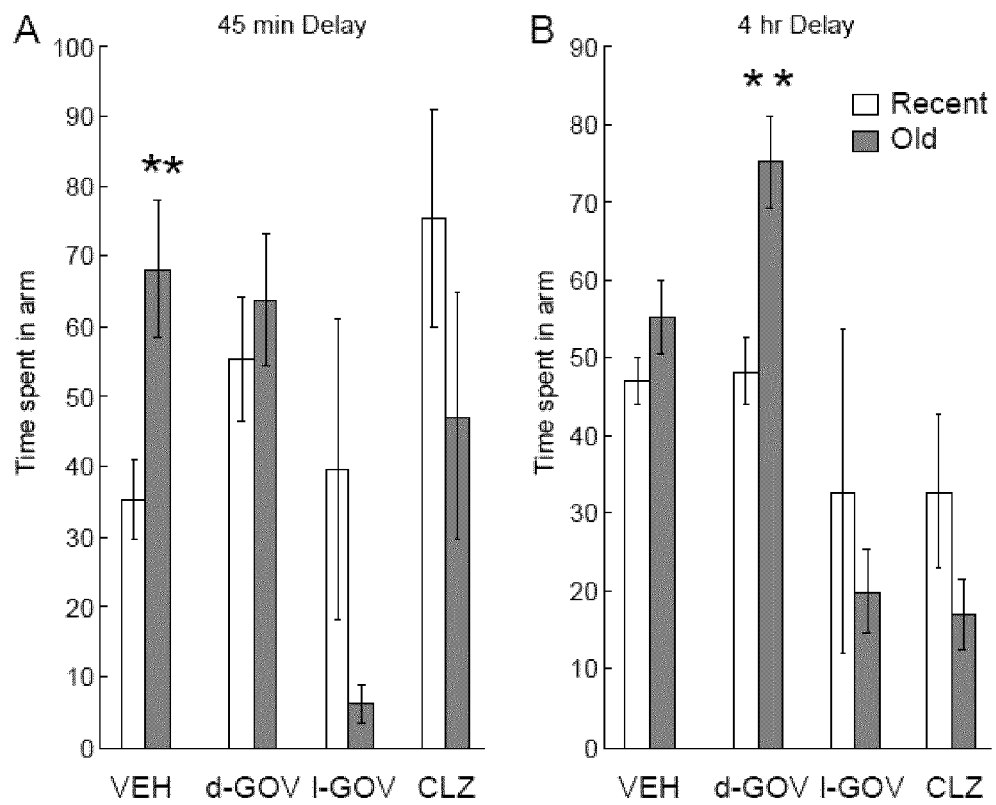
FIG. 6 presents the results of the analysis of temporal order recognition in animals treated with d- or l-govadine: (A) temporal order effect after 45 min delay, and (B) temporal order effect after 4 hr delay, in animals treated with vehicle (VEH), 1.0 mg/kg d-govadine (d-GOV), 1.0 mg/kg l-govadine (l-GOV), or 5.0 mg/kg clozapine (CLZ). **recent vs old comparison, Tukey's post hoc, $p<0.01$.

The results are shown in FIG. 6 (**recent vs old comparison, Tukey's post hoc, p<0.01). At the 45 min delay, a robust temporal order effect was observed in VEH treated animals and was abolished by 1.0 mg/kg d-govadine, 1.0 mg/kg l-govadine, and 5.0 mg/kg CLZ (FIG. 6A). At the 4 hr delay, no temporal order effect was observed in VEH treated animals, as well as l-govadine and CLZ treated animals (FIG. 6B). However, treatment with d-govadine restored temporal order recognition at the 4 hr delay. The nature of the l-govadine and CLZ-evoked temporal order deficit was different than the d-govadine mediated deficit, as the locomotor profiles of these animals were very different (see Table 4). VEH and d-govadine treated animals made more arm entries and moved further than l-govadine or CLZ treated animals. It is likely that the motor suppression observed in the l-govadine and CLZ groups was meditated by the D2 antagonism of these compounds.

TABLE 4

Temporal Order Recognition Table

| Compound | Distance Travelled | | Arm Entries | |
| --- | --- | --- | --- | --- |
| | 45 min. | 4 hr. | 45 min. | 4 hr. |
| Vehicle | 1625 ± 265 | 2160 ± 142 | 8.6 ± 2.2 | 11 ± 1.0 |
| d-Govadine | 2433 ± 363 | 2091 ± 114 | 14.8 ± 1.9 | 11 ± 1.1 |
| l-Govadine | 587.7 ± 109 | 824 ± 135 | 3.67 ± 1.9 | 3.5 ± 0.9 |
| Clozapine | 1286 ± 177 | 1098 ± 74 | 7.0 ± 1.9 | 6.0 ± 1.6 |

These data suggest that d-govadine has potential as a cognitive enhancer, whereas the strong D2 antagonism activity of l-govadine makes it an unlikely candidate as a cognitive enhancer.

Example 12

Psychopharmacological Assessment of DL-Govadine

Animals: All experiments were performed with male Long-Evans rats (Charles River, Saint Constant, Quebec) weighing 250-400 grams. All animals were maintained on a reverse light cycle with the dark cycle beginning at 8 am and ending at 8 pm. Animals were pair housed, except in the delayed win shift experiments where they were single housed in order to control feeding and maintain rats at 85% free-feeding weight. All protocols were approved by the University of British Columbia Animal Care Committee and conducted in accordance with policies outlined by the Canadian Council on Animal Care.

Drug Preparation: In each experiment, dl-govadine was used as a racemic mixture containing 50% of each the d- and l-isomer. dl-govadine was dissolved in isotonic saline solution with 30% dimethylformamide (Sigma-Aldrich, St Louis, Mo.) and 1% Acetic Acid (Sigma-Aldrich, St Louis, Mo.). Mass spectrometry confirmed these solvents did not alter dl-govadine. Clozapine (Sigma-Aldrich, St Louis, Mo.) was dissolved in saline containing 1% acetic acid. d-AMPH (US Pharmacopeia, Rockville, Md.) was dissolved in isotonic 0.9% saline.

Pharmacology: The affinity of dl-govadine for dopamine (DA), serotonin, and noradrenaline receptors was assessed by MDS Pharma Services, Inc (King of Prussia, Pa.). All receptors were heterologously expressed CHO cells and $IC_{50}$ values were determined by a non-linear, least squares regression analysis using MathIQ (ID Business Solution Ltd, UK). $K_i$ was calculated (Y. Cheng & Prusoff 1973) from the observed $IC_{50}$ of the tested compound, the concentration of radioligand employed in the assay, and the historical values for the $K_d$ of the ligand (obtained experimentally at MDS Pharma Services).

Behavioral Assays

Catalepsy: In order to assess the cataleptic effect of dl-govadine, a dose-response curve was established in naïve animals. Testing occurred in a plexiglas box (28 cm×45 cm×20 cm) containing a horizontal steel bar located 8 cm above floor level. Each animal was allowed 1 hr acclimation to the box prior to testing and then injected subcutaneously (SC) with either vehicle (N=8), or dl-govadine 6 mg/kg (N=5), 3 mg/kg (N=5), 1.5 mg/kg (N=5), or 1.0 mg/kg (N=6). After injection animals were returned to the test box and catalepsy testing occurred at 1, 15, 30, and 45 minutes after injection. Testing at each time point lasted 2 min after the forepaws of each rat was placed on the bar. Behavior was recorded with a video camera (Cohu, Poway, Calif.) and scored off-line. The cumulative time spent immobilized with both forelimbs on the horizontal bar was scored for each 2 min test epoch. Videos selected at random were scored independently by a second observer and a high inter-rater reliability was observed ($R^2$=0.93, F=393.4, p<0.05). The $ED_{50}$ was calculated from the number of animals that exhibited 60 sec of contact time across each dose at the 45 min time point.

Amphetamine induced locomotion (AIL): Animals were habituated to locomotor arenas for 1 hr on 4 consecutive days prior to testing. Locomotor activity was assessed on day 1 of habituation and treatment groups were assigned in a counter-balanced manner determined by distance traveled on day 1. Animals received intraperitoneal (IP) injections of dl-govadine at 0.3 mg/kg (N=7), 1.0 mg/kg (N=6), 3.0 mg/kg (N=6), or vehicle (VEH) (N=7) 15 minutes before d-AMPH on day 5. dl-govadine/VEH was injected 15 minutes before 1.5 mg/kg d-AMPH or SAL and distance traveled was assessed for 1 hr post d-AMPH/SAL injection. A separate group of animals received dl-govadine (N=8) or VEH (N=7) on days 3 and 4 previous to d-AMPH testing on day 5 to assess if previous experience with dl-govadine to suppressed AIL. Distance traveled was recorded with Noldus Ethovision XT (Noldus, Leesburg, Va.) and analyzed off-line. The $ED_{50}$ was calculated as the dose necessary to inhibit d-AMPH induced locomotion by 50% over 1 hr in animals which received VEH.

Conditioned avoidance responding: Conditioned avoidance responding (CAR) was assessed as described in Example 10. On the drug test day, animals were injected SC with either vehicle (N=8), or dl-govadine (0.3 mg/kg, N=7; 1.0 mg/kg, N=8; 3.0 mg/kg, N=7) then placed in the avoidance box with house lights illuminated. After 15 min, the presentation of the 100 CS-US pairings began and were scored as during training.

Sensitization: Animals were removed from the colony and taken to a holding room where they received either IP d-AMPH or saline every Monday, Wednesday, and Friday. Doses started at 1 mg/kg and increased 1 mg/kg each week over 5 weeks to 5 mg/kg. 25 days after the induction phase, behavioral sensitization was assessed over 3 days in locomotor chambers (plexiglass box, 40 cm×40 cm×40 cm) where speed and distance traveled were recorded using Noldus Ethovision XT (Noldus, Leesburg, Va.). The first day consisted of a 2 hr acclimation session, and prior to counter balanced injections of either 0.5 mg/kg d-AMPH or saline on days 2 and 3 animals were acclimated for 1 hr. Experiments were run in two separate cohorts of 30 animals to minimize the time between testing sensitization and LI.

Latent Inhibition: LI tests were performed in rats treated with 1.0 mg/kg acute d-AMPH, sensitized rats, and drug-naive rats. LI testing began 5 days post-challenge of the escalating dose regime. Animals in both conditions (chronic saline or sensitized) were randomly assigned to either non-pre-exposed (NPE) or pre-exposed (PE) groups. Testing took place over 3 consecutive days. Sensitized or saline animals were randomly assigned to VEH or 1.0 mg/kg dl-govadine groups and received SC injections 15 min before each pre-exposure trial. Animals in the PE group received 50 presentations of the CS (10 sec duration) per day at a variable interval for the first two days. Animals in the NPE group were placed in the chamber for an equal time as the PE animals. Conditioning (COND) consisted of 100 CS-US pairings. Latency to cross into the other compartment and the number of total beam breaks were recorded. Drug-naïve animals receiving acute 1.0 mg/kg AMPH were injected IP 45 min before the COND trial.

Delayed Spatial Win-Shift Task: The delayed spatial win-shift was performed in sensitized and drug-naive animals. Briefly, the delayed spatial win-shift (DSWSh) procedure consisted of 3 phases; training, delay, and test. During the training phase animals were placed on the maze with four of eight arms open. After the fourth food pellet (Noyes, Lancaster, N.H.) was consumed, the animal was confined to the last arm visited for the delay period with the light extinguished. After the delay, the light was turned on, all 8 arms opened, and food was available only in the 4 arms blocked during the training phase. Re-entry into an arm constituted an error and a criterion of 1 error or less for 2 consecutive days was required to advance to the next delay or the test day. Animals were trained to criterion at a 1, 5, and 30 min delay. When an animal reached criterion at the 30 min delay, it was then assigned to the 30 min or 12 hr delay test group. Prior to each test, rats received counter-balanced SC injections of either VEH or 1.0 mg/kg dl-govadine 30 min before the test phase. After the first test trial, criterion performance was re-established and the second counter-balanced injection was delivered.

Microdialysis: Microdialysis experiments were conducted as described in Example 11. Drug treatment phase was initiated with a 1.0 mg/kg SC injection of dl-govadine or VEH. After the experiments, rats were deeply anesthetized, brains were removed and stored in 20% w/v sucrose and 4% v/v paraformaldehyde. Brains were sliced into 50 um coronal sections, stained with cresyl violet and examined for probe placement.

Data Analysis: Data were imported into Matlab (Mathworks, Nantick, Mass.) or R (see r-project website) for statistical analysis. Each data set was subjected to analysis of variance (ANOVA) testing. ANOVA testing of DSWSh data employed a between/within design: treatment was as a within subjects measurement as every animal received a test day with either VEH or dl-govadine; delay (30 min, 12 hour) and background (saline, sensitized) were treated as between subjects variables as each animal was only received one of these. Microdialysis data was assessed via two-way ANOVA and treatment (dl-govadine, VEH) was an independent variable, and time was a within subjects repeated variable. When appropriate, Tukey's post-hoc testing was applied for multiple comparisons with an alpha=0.05. A general linear model using a probit kernel was applied to the data to determine the $ED_{50}$ of dl-govadine on catalepsy, CAR, and AIL.

Results dl-Govadine Exhibits a High Affinity for Dopamine Receptors dl-govadine exhibited high affinity for DA receptors, moderate affinity for noradrenaline receptors, and relatively weak affinity for serotonin receptors (Table 5). Higher affinity for D1 receptors compared to D2 was observed for dl-govadine which is reflected as a low D1/D2 ratio (Table 6).

TABLE 5

Receptor Binding for dl-Govadine
($K_i$ in nM or % Inhibition at 10 μM)

| Receptor | Affinity ($K_i$)/mM |
|---|---|
| α1A | 0.44 |
| α1B | 2.10 |
| α1D | 0.28 |
| α2B | 0.31 |
| D1 | 0.0064 |
| D2L | 0.28 |
| D2S | 0.56 |
| D3 | 0.58 |
| D5 | 0.01 |
| 5-HT1 | 2.87 |
| 5-HT1A | 19.30 |
| 5-HT2A | 18.70 |
| 5-HT2C | 56.50 |

TABLE 6

Pharmacological Efficacy of dl-Govadine Compared to Clozapine and l-Stepholidine

| Compound | D1/D2 | D1 ($K_i$)/μM | D2L ($K_i$)/μM | CAR ($ED_{50}$)/ mg/kg | AIL ($ED_{50}$)/ mg/kg | Catalepsy ($ED_{50}$)/ mg/kg |
|---|---|---|---|---|---|---|
| dl-Govadine | 0.023# | 0.0067†# | 0.283‡# | 0.720# | 1.70# | 4.70# |
| Clozapine | 0.438*** 0.660* | 0.189†*** | 0.431‡*** 1.400‡** | 7.70* | 4.27* | n/a |
| l-Stepholidine | 0.150** 0.850* | 0.013†** | 0.085‡** | 0.270* | 2.36* | 3.60* |

Figure 7:
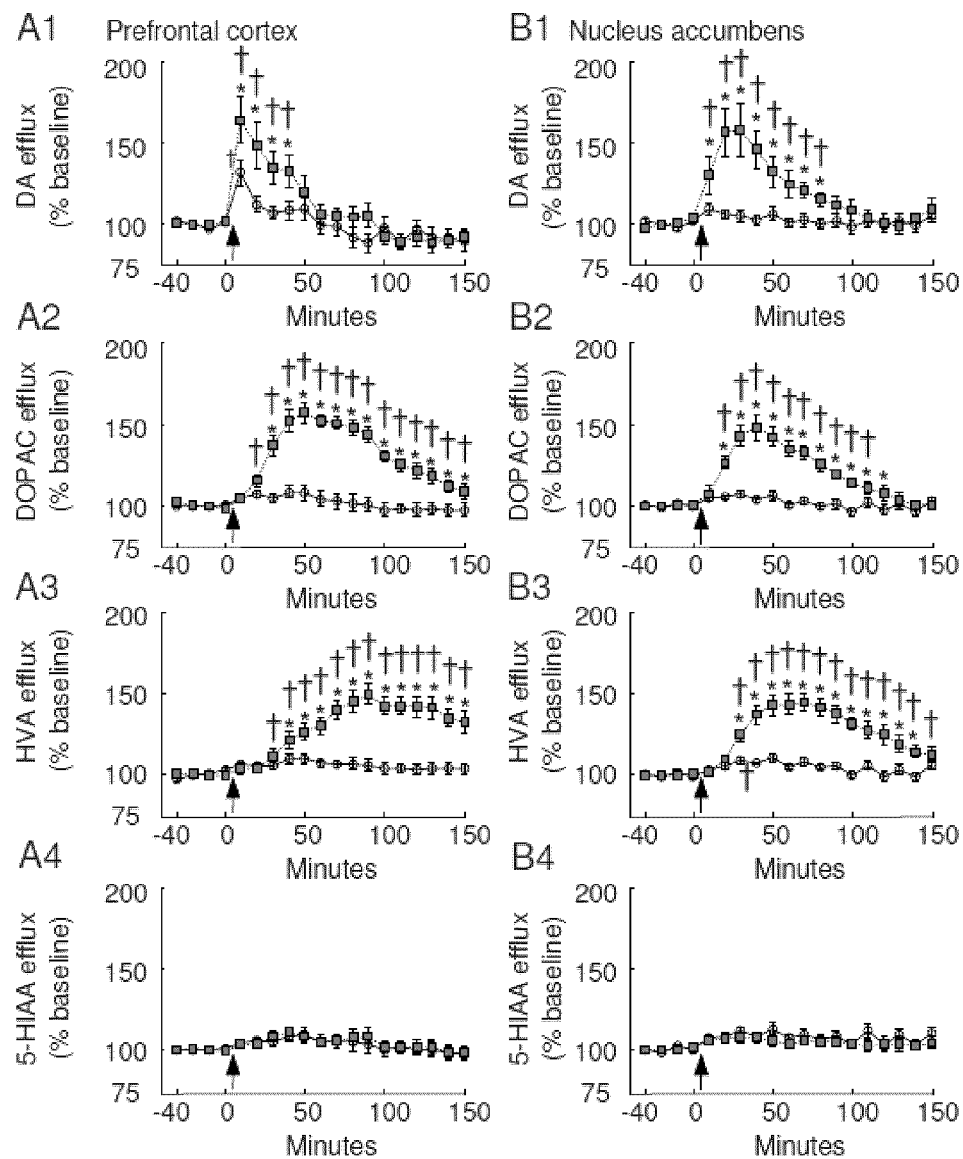
FIG. 7 presents the results of microdialysis analysis of levels of dopamine (A1, B1); 3,4-dihydroxyphenylacetic acid (DOPAC) (A2, B2); homovanillic acid (HVA) (A3, B3), and 5-hydroxyindoleacetic acid (5-HIAA) (A4, B4) in the prefrontal cortex (A series) and nucleus accumbens (B series) in rats treated with dl-govadine (grey squares) or vehicle (open circles). (vehicle vs dl-govadine, *Tukey's post hoc, p<0.05; Tukey's post hoc, p<0.05)

Present data
*Natesan et al., 2008, Psychopharmacology, 199: 275-289
**Xu, S. X. et al., 1989, Acta Pharmacol. Sin. 10, 104-110
***NIMH PDSP Database certified data
†Comparison ligand = 0.14 nM SCH-23390
‡Comparison ligand = 0.16 nM Spiperone dl-Govadine Increases Dopamine Efflux in the Prefrontal Cortex and the Striatum Typical in vitro probe recoveries of external standard solutions at room temperature (21° C.) were: 12% for DA, 9% for DOPAC, 9% for HVA, and 8% for 5-HIAA. Basal DA levels were detected as 0.18+/−0.03 and 0.17+/−0.02 nM in the PFC; 1.59+/−0.20 nM and 1.97±0.34 nM in the NAc for VEH and dl-govadine treated animals, respectively. A single injection of 1.0 mg/kg SC dl-GOV increased DA in both the PFC (two-way ANOVA, main effect of treatment, $F(1,300)=9.07$, $p=0.0028$) and NAc (two-way ANOVA, main effect of treatment $F(1,243)=18.64$, $p<0.0001$) relative to VEH injection. In the PFC, DA levels peaked during the first 10 min after injection where as the NAc peak was observed 20-30 min post injection (FIG. 7 A1, B1). Increases in both DA metabolites were observed in the PFC (DOPAC, two-way ANOVA, main effect of treatment, $F(1,300)=6.01$, $p=0.0148$; HVA, two-way ANOVA, main effect of treatment, $F(1,300)=5.34$, $p=0.0215$) and the NAc (DOPAC, two-way ANOVA, main effect of treatment, $F(1,243)=16.92$, $p=0.001$; HVA, two-way ANOVA, treatment× time interaction, $F(1,243)=18.48$, $p<0.0001$). A transient increase in DA was also observed in the PFC in response to VEH injection which was not observed in the NAc (FIG. 7 A1). No increase in the serotonin metabolite, 5-HIAA, was observed in either brain region (FIG. 7 A4, B4).

Catalepsy is Observed with High Doses of dl-Govadine

Figure 8:
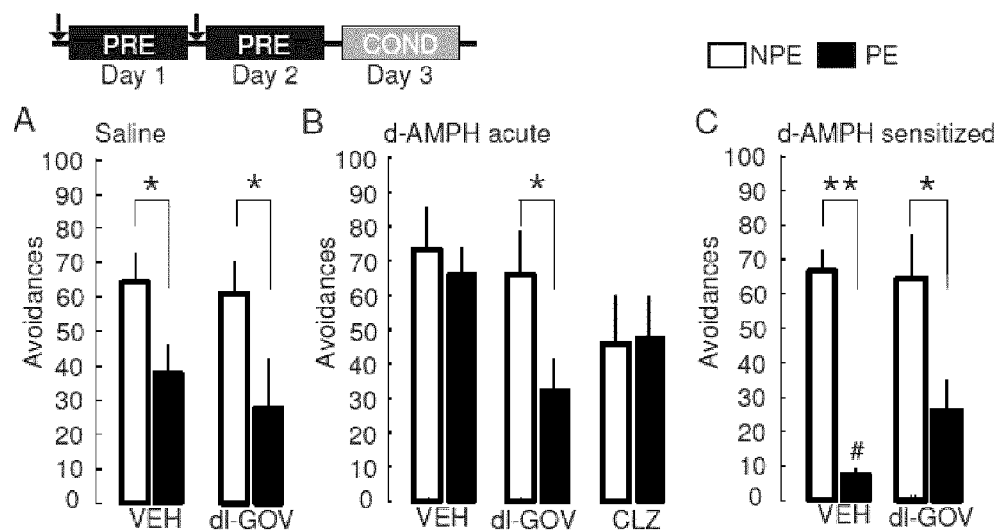
FIG. 8 presents the results of analysis of latent inhibition in rats treated with dl-govadine: a graphic describing the experimental protocol is shown at the top of the Figure. Data shown are the mean number of avoidances±SEM during conditioning in animals treated with vehicle (VEH) or 1.0 mg/kg dl-govadine 15 minutes before each PRE trial. Black bars represent pre-exposed animals and white bars represent animals that were not pre-exposed to the conditioning stimulus. (two-way ANOVA, main effect of exposure, $F_{(1,94)}=9.38$, $p=0.0029$; NPE vs PE, *Tukey's post hoc, $p<0.05$; **Tukey's post hoc, $p<0.01$; VEH+PE$_{saline}$ vs VEH+PE$_{sensitized}$ #Tukey's post-hoc, $p<0.05$).

A dose-dependent increase ($R^2=0.91$, $F=28.41$, $p<0.05$) in immobilized contact time was observed with increasing doses of dl-govadine. Strong and extended catalepsy was observed at the 6.0 mg/kg dose while mild motor suppression was observed at 1.0 mg/kg without any sign of overt catalepsy. Furthermore, this dose did not induce a spike in cataleptic-like behavior at 15 min post-injection, unlike the 1.5 mg/kg and 3.0 mg/kg doses (multiple comparison, $p<0.05$). The $ED_{50}$ value calculated at 45 min from the four doses of dl-govadine used yielded a value of 4.7 mg/kg, which is comparable to the value of 3.6 mg/kg observed for 1-SPD (see Table 6).

dl-Govadine Impairs Conditioned Avoidance Responding dl-govadine dose-dependently suppressed avoidances ($R^2=-0.5$, $F=29.02$ $p<0.0001$) in animals proficient with CAR. Decreased avoidance behavior was accompanied by an increase in escapes in dl-govadine and CLZ treated animals (dose×measure interaction $F(4,75)=16.56$ $p<0.001$), providing strong evidence that the disruption of avoidance behavior was not due to motor impairment. The $ED_{50}$ value calculated at 20 min post-injection from the three doses of dl-govadine used yielded a value of 0.723 mg/kg, which is higher than the value of 0.27 mg/kg for 1-SPD, obtained at the same time point post-treatment (see Table 6).

dl-Govadine Dose Dependently Inhibits d-Amphetamine Induced Locomotion 1.5 mg/kg IP d-AMPH increased locomotor activity relative to saline injection, and was dose-dependently suppressed ($R^2=-0.4$, $F=18.87$, $p=0.00022$) with increasing doses of dl-govadine prior to d-AMPH. An $ED_{50}$ of 1.7 mg/kg was calculated for dl-govadine mediated suppression of AIL (see Table 6).

dl-Govadine Treatment at Pre-Exposure Reverses the Bidirectional Effects of Sensitization and Acute d-Amphetamine on Latent Inhibition Injections of VEH or dl-govadine immediately before each pre-exposure session had no subsequent effect on LI in non-sensitized animals as both treatments produced an indistinguishable number of avoidances in pre-exposed animals (FIG. 8A). Acute d-AMPH has been repeatedly shown to abolish LI, and this effect was replicated in the current study (FIG. 8B, left). Remarkably, administration of dl-govadine prior to each pre-exposure session ameliorated this effect and restored LI in acute d-AMPH-treated animals (FIG. 8B, middle).

To address the possibility that pretreatment with dl-govadine blunts the motor-stimulant effect of d-AMPH, thereby mediating the decreased number of avoidances observed, a separate group of animals were pretreated with either dl-govadine or VEH on two consecutive days and placed in an open field. On the third day animals were injected with 1.5 mg/kg d-AMPH and placed back in the open field where speed and distance traveled were recorded. No effect of dl-govadine pretreatment was observed on this measure of AIL (d-AMPH+prior dl-govadine, 12,798±1,504 versus d-AMPH+prior VEH, 12,158±1971 (mean±SEM); Student's t-test, $p>0.05$), suggesting that dl-govadine pretreatment did not suppress the motor-stimulant effect of d-AMPH but rather suppressed the ability of d-AMPH to facilitate the association between the CS and the US. We next assessed if pretreatment with 5.0 mg/kg SC clozapine (CLZ) restored LI in the same manner as dl-govadine. We observed that CLZ pretreatment decreased the number of avoidances in PE animals, however, NPE animals also showed a similar decrease in the number of avoidances relative to other NPE animals (FIG. 8B, right). No statistical difference ($p>0.05$) was found between NPE or PE animals receiving CLZ indicating a lack of LI, thus CLZ pretreatment does not offset acute d-AMPH induced deficits in LI in the same manner as dl-govadine.

Figure 9:
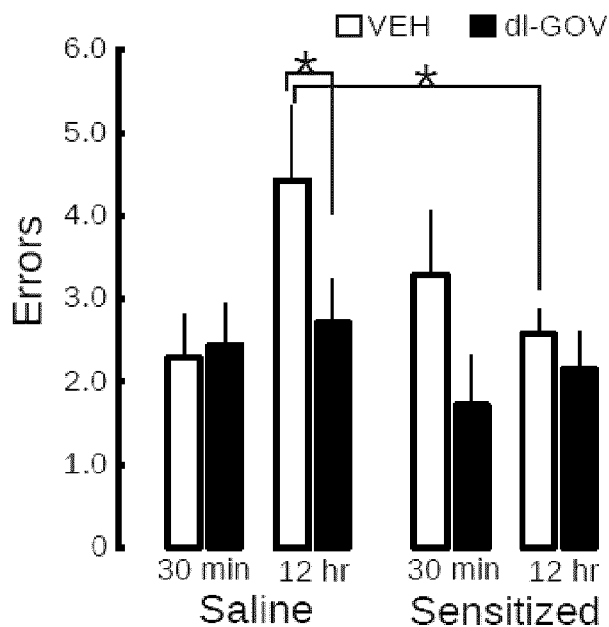
FIG. 9 presents the results of the analysis of delayed spatial win-shift in rats treated with dl-govadine: cognitive performance was assessed as the mean number of test phase errors±SEM for vehicle (VEH; white bars) and dl-govadine (dl-GOV; black bars) treated animals for chronic saline and d-AMPH sensitized rodents performing the delayed spatial win shift. (*Tukey's post hoc, p<0.05).
Figure 9:
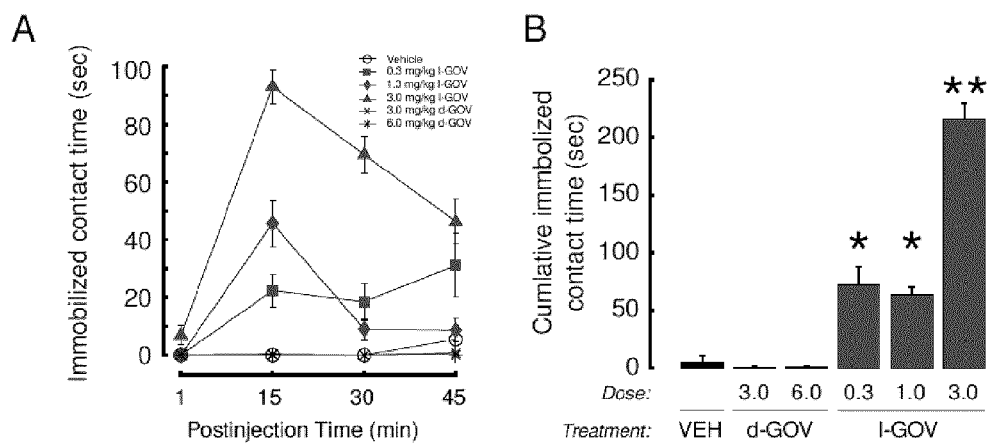

Finally, the consequences of the 5-week escalating dose d-AMPH sensitization regime on the expression of LI were explored (FIG. 8C). Sensitization was confirmed in animals receiving repeated d-AMPH as an increase locomotion to 0.5 mg/kg IP d-AMPH challenge relative to those who received repeated saline (saline 178±16% versus sensitized, 247±22% (mean±SEM); students t-test, $p<0.05$). The 5-week increasing-dose regime of d-AMPH had the unanticipated effect of significantly decreasing the number of avoidances in the PE group, indicative of increased in LI (FIG. 8C, left). Sensitized PE animals pretreated with dl-govadine exhibited the same number of avoidances observed in non-sensitized PE animals (FIG. 8C, right) showing that dl-govadine restored LI to levels observed in controls (FIG. 8A). It is noteworthy that in each of the groups tested, an inverse relationship was observed between avoidances and escapes (exposure×measure interaction, $F(1,189)=28.4$, $p<0.001$), indicating intact motor performance in rats treated with either dl-govadine or CLZ.

dl-Govadine Improves Cognitive Performance on the Delayed Spatial Win-Shift Task A significant main effect of treatment (three-way ANOVA, main effect of treatment, $F(1,48)=4.40$, $p<0.041$) was observed in this experiment, confirming that dl-govadine improved the ability of rodents to use a memory-based foraging strategy. In large part, this effect was attributable to a significant increase in errors at the 12 hr delay in non-sensitized animals that was blocked by treatment with dl-govadine 30 min prior to the test phase (FIG. 9, left). However, dl-govadine had no effect at the 30 min delay in non-sensitized animals. In the current study, sensitized animals make significantly fewer errors at a 12 hr delay (three-way ANOVA, background×delay interaction, $F(1,48)=4.74$, $p<0.05$, FIG. 6, right) than their non-sensitized counterparts indicating that sensitization may have improved working memory performance. Furthermore, a tendency for increased errors at 30 min in sensitized animals was observed which was suppressed by dl-govadine (three-way ANOVA, treatment×background×delay interaction, F(1,48)=3.11, p<0.08, FIG. 9). Taken together, these data reveal the complex nature of sensitization-evoked perturbations on working memory and establish the ability of dl-govadine to improve performance of this complex cognitive task.

The study presented in this Example demonstrates that dl-govadine at a dose of 6 mg/kg induced strong catalepsy, whereas only transient bouts of inactivity were observed briefly with the lower doses tested. These lower, non-cataleptic doses were therefore selected for all subsequent experiments. Importantly, non-cataleptic doses of dl-govadine suppressed AIL, consistent with an ability to mitigate behavioral abnormalities arising from hyperdopaminergia, including the positive symptoms of schizophrenia. In addition, dl-govadine at doses of 1.0 and 3.0 mg/kg suppressed avoidance behavior without affecting escape responses. The efficacy of dl-govadine on measures of catalepsy and antipsychotic efficacy was comparable to 1-SPD evidenced by their similar $ED_{50}$ values (Table 4). When compared with CLZ, both dl-GOV and 1-SPD exhibited a lower $ED_{50}$ to suppress AIL and CAR, indicating that both these compounds may provide an effective treatment option for the positive symptoms of schizophrenia.

This study also demonstrated that systemic administration of CLZ or dl-govadine during CS pre-exposure blocked the increase in avoidance responses normally produced by acute d-AMPH in animals pre-exposed to the CS. Importantly, CLZ also disrupted avoidance behavior in NPE rats given acute d-AMPH, suggesting a more general effect on the formation of a CS-US association, but this general impairment was not observed with dl-govadine treatment indicating that dl-govadine may more selectively target the compromised attentional processes which disrupt LI than CLZ. These data thus establish that dl-govadine exhibits a different profile than clozapine on this measure and may more effectively target cognitive pathologies than this currently approved antipsychotic.

Together, these data indicate that dl-govadine may have the unique ability to influence both positive and negative symptom poles of schizophrenia.

Example 13

Effect of D- and L-Govadine on Catalepsy and Latent Inhibition

Catalepsy testing was conducted as described in Example 12. After the 1 hr acclimation to the box, rats were injected subcutaneously (SC) with either vehicle (N=6), 0.3 mg/kg l-govadine (L-GOV) (N=6), 1.0 mg/kg L-GOV (N=6), 3.0 mg/kg L-GOV (N=6), 3.0 mg/kg d-govadine (D-GOV) (N=6), or 6.0 mg/kg D-GOV (N=5).

Figure 10:
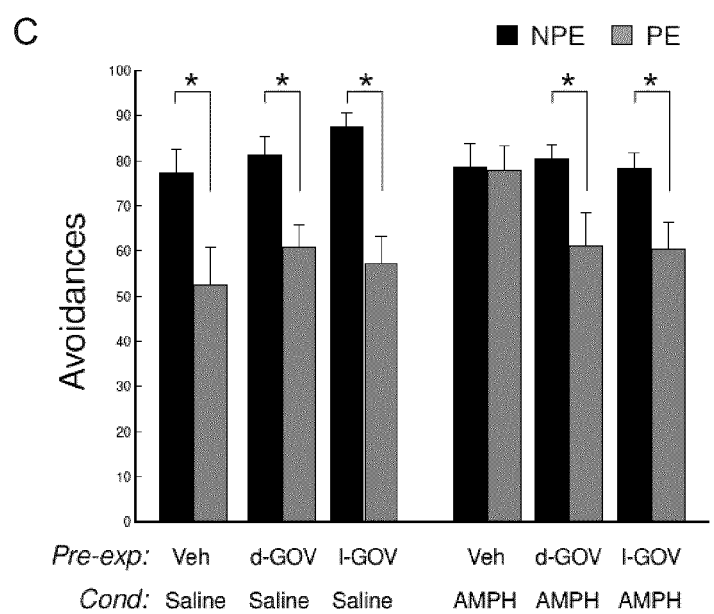
FIG. 10 presents the results of analysis of cataleptic behavior (A, B) and latent inhibition (C) in rats treated with d-govadine (d-GOV), l-govadine (l-GOV) or with vehicle (VEH); (A) immobilized contact time as a function of postinjection time, and (B) total amount of immobilized contact time summed across each time point (All data are presented as mean±SEM. (*comparison with VEH group, Tukey's post-hoc, p<0.05)), and (C) number of avoidances for animals pretreated with saline or 1.0 mg/kg AMPH prior to conditioning and injected with Vehicle, D-GOV or L-GOV prior to each pre-exposure session (*Tukey's post hoc, p<0.05).

The results are shown in FIG. 10. Catalepsy was observed in L-GOV treated animals, but not D-GOV treated animals (dose X time interaction, two-way ANOVA F(20,149)=10.64, p<0.0001). Cataleptic behavior peaked in L-GOV treated animals 15 min post injection (FIG. 10A). An increase in the total amount of immobilized contact time summed across each time point was observed with each dose of L-GOV relative to vehicle (VEH) and D-GOV (FIG. 10B). No evidence of catalepsy was observed in D-GOV treated animals.

The effects of the two individual enantiomers of govadine on latent inhibition (LI) were also tested as described in Example 12. The results indicated that, similar to the racemic compound, treatment with either D- or L-GOV during pre-exposure restored LI in animals given d-AMPH prior to conditioning (see FIG. 10C).

Example 14

Effect of D- and L-Govadine on Social Interaction

Prior to social interaction testing all animals (experimental and partner) were separately acclimated to the social interaction environment for 10 min on 2 consecutive days. Experimental rats were neonatal ventral hippocampal lesioned (NVHL) and control (Sham) animals. All partner rats were handled daily for 10 minutes one week prior to SI testing. The SI environment consisted of a 83×90×30 cm open field with each surface painted black. On the day of social interaction testing, experimental rats were injected IP with either VEH (Sham, N=17; NVHL, N=15), 1.0 mg/kg l-govadine (L-GOV) (Sham, N=18; NVHL, N=13), or 1.0 mg/kg d-govadine (D-GOV) (Sham, N=17; NVHL, N=15) 15 minutes prior to SI testing. For testing, partner rats were placed in the environment first and then experimental animals (Sham or NVHL) were introduced for 10 minutes. Partner and experimental rats were matched for weight, size, and age. Behavior was recorded by a camera mounted over the environment and scored offline. The time spent interacting between the two animals was scored as described in Sams-Dodd, F., 1999, *Review in Neurosciences*, 10:59-90.

Vehicle treated NVHL rats exhibited a robust decrease in social interaction time. However, for both D-GOV or L-GOV treated animals, comparable levels of SI were observed in NVHL rats and Sham controls.

Example 15

Effect of D- and L-Govadine on Dopamine Neurons

In this Example, the ability of individual isomers to reverse the $D_2$ receptor-mediated decreases in firing of midbrain dopamine (DA) neurons was investigated. DA efflux in both the Nucleus Accumbens (NAc) and medial prefrontal cortex (mPFC) was also measured in vivo using microdialysis and HPLC-ED.

Horizontal midbrain slices (220 µm) were prepared from male Sprague Dawley rats (3-4 weeks old). Cell-attached voltage-clamp recordings were used to examine tonic firing rate of DA neurons at 31-32° C. using patch pipette and bathing solutions consisting of physiological saline. Putative DA neurons were identified by spontaneous pacemaker firing (1-3 Hz) with broad APs (≥2.0 ms). Identified cells not responsive to Quinpirole (500 nM), a $D_2$ DA receptor agonist, were excluded from further recording. Cells were also filled with biocytin or Alexa for posthoc-identification using TH immunostaining. Microdialysis probes (2 mm active membrane) were implanted in the NAc and mPFC ~16 hrs prior to start of the experiment and continuously perfused aCSF. Dialysates were collected at 10 min intervals and assayed for DA content by HPLC-EC. l- or d-govadine (1 mg/kg) was administered once stable DA levels were established.

Figure 11:
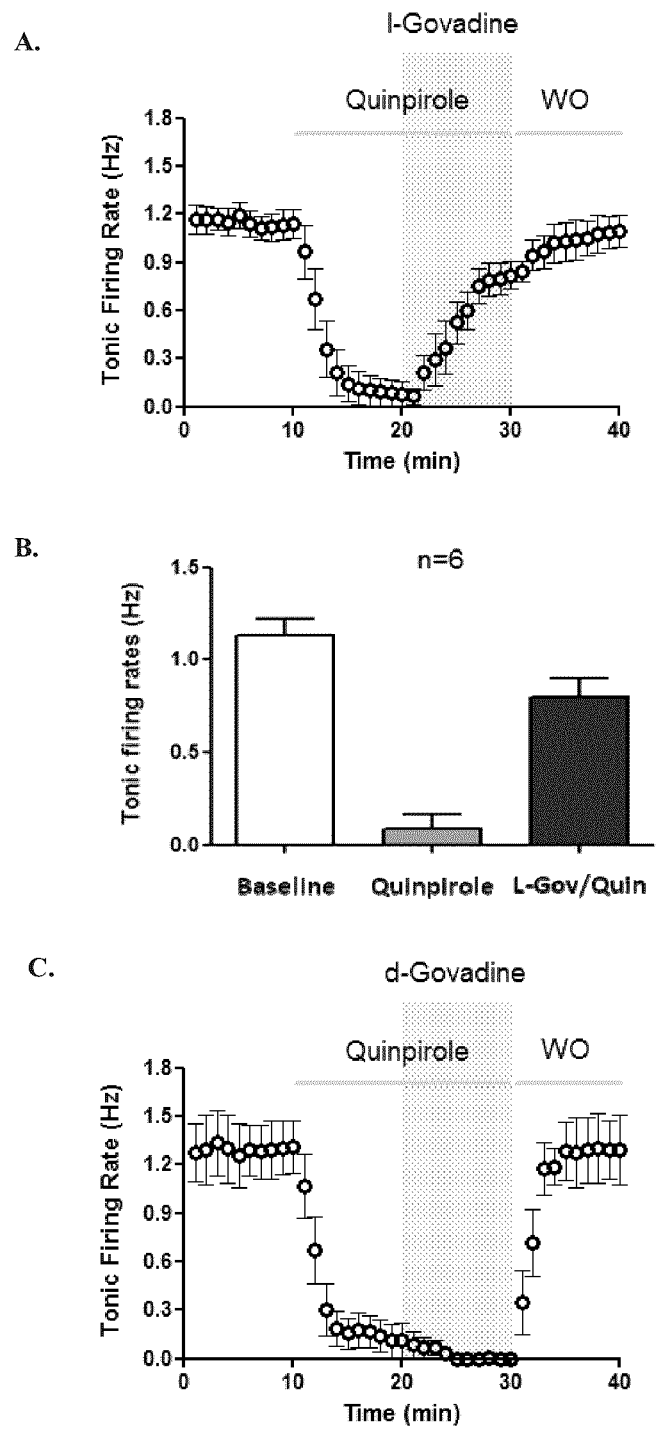
FIG. 11 presents the results of analysis of the effect of l-govadine (A,B) and d-govadine (C,D) on firing of midbrain dopaminergic neurons in the presence of quinpirole (500 nM), a D2 dopamine receptor agonist, and the dose-dependency (100 mM to 10 µM) of this effect (E).

The results are shown in FIG. 11. Neither l-govadine (FIGS. 11A,B) nor d-govadine (FIGS. 11 C,D) alone had an effect on the spontaneous firing activity of midbrain DA neurons. Consistent with previous findings, Quinpirole stimulated $D_2$ autoreceptors thereby decreasing the tonic firing activity through GIRK activation. Co-application of l-govadine, but not d-govadine, during the peak inhibitory effect of Quinpirole antagonized the $D_2$ autoreceptor-mediated decreases in tonic firing of DA neurons.

The microdialysis experiments confirmed enhanced DA efflux in NAc and mPFC following injections of l-govadine and dl-govadine, but not d-govadine, when compared to control (FIG. 11E). This effect was dose-dependent (100 nM to 10 μM).

The data shown in FIG. 11 indicate that d- and l-govadine have differential effects. Specifically, l-govadine, but not d-govadine, can antagonize $D_2$ receptors in midbrain DA neurons in a dose-dependent manner, suggesting that l-govadine, and not d-govadine, possesses antipsychotic activity. The effects of l-govadine are likely mediated by direct blockade of $D_2$ autoreceptors or possibly inhibition of intracellular signalling including G protein binding.

Example 16

Effect of D- and L-Govadine on Conditioned Avoidance Responding #2

Figure 12:
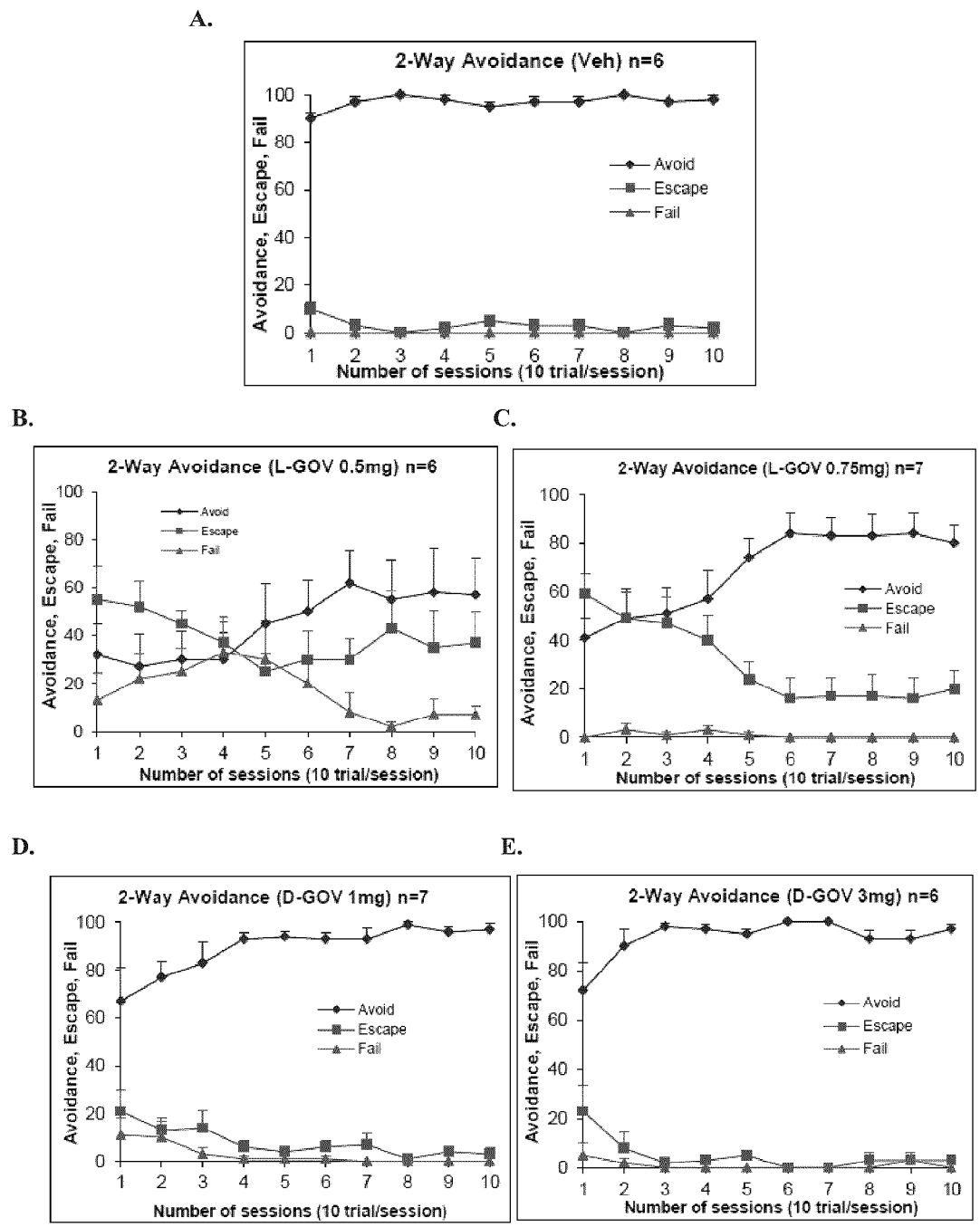
FIG. 12 presents the results of the analysis of conditioned avoidance responding in rats treated with vehicle (Veh) (A), 0.5 mg/kg l-govadine (L-GOV) (B), 0.75 mg/kg L-GOV (C), 1 mg/kg d-govadine (D-GOV) (D) or 3 mg/kg D-GOV (E).
Figure 13:
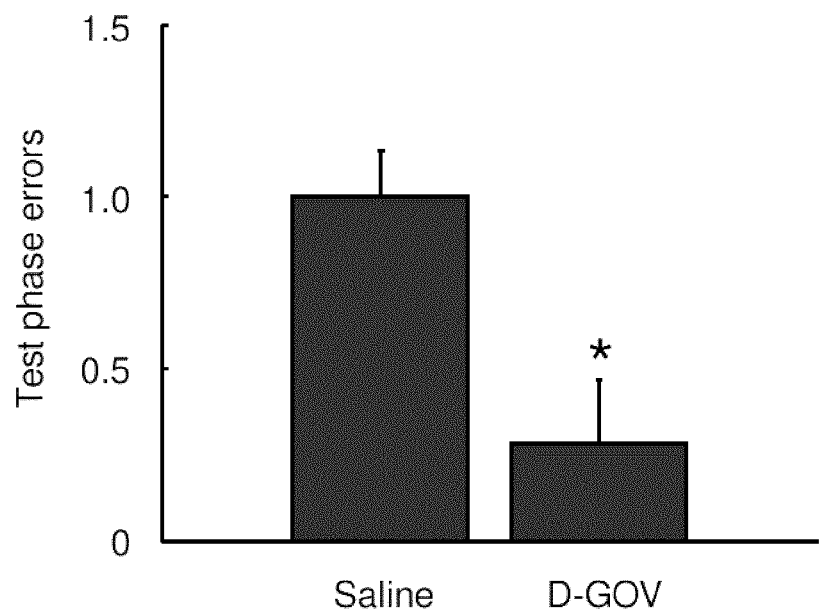
FIG. 13 presents the results of a delayed spatial win-shift experiment using rats that received an injection of 1.0 mg/kg D-GOV or vehicle. *Paired T-test, p=0.0082, (n=7).

The effect of d- and l-govadine in the conditioned avoidance responding (CAR) test was investigated as described in Example 9, but using dosages of 1.0 mg/kg or 3.0 mg/kg d-govadine and 0.5 mg/kg and 0.75 mg/kg of l-govadine. The results are shown in FIG. 12 and confirm that l-govadine, but not d-govadine, suppresses CAR.

Example 17

Effect of D-Govadine on Delayed Spatial Win-Shift

The effect of d-govadine was investigated in a prospective coding version of the delayed spatial win-shift experiment. Animals received 6 training phase arms that biases the use of prospective foraging strategy (see Seamans, J. K., et al., 1998, *J. Neuroscience*, 18(4):1613-1621; Cook, R. G., et al., 1985, *Animal Behavior Processes*, 11:453-469). Each rat received an injection of 1.0 mg/kg d-govadine (D-GOV) or vehicle (VEH) 15 minutes prior to the training phase and a 15 min delay was employed between the training and test phase. The rat must visit the remaining two arms in the test phase to complete the task.

The results are shown in FIG. 15 and demonstrate that d-Govadine dramatically improved this strictly PFC-dependent foraging strategy (*Paired T-test, p=0.0082, (n=7)). This data indicates that d-govadine improves prospective memory.

Example 18

Comparison of Effect of D,L-Govadine, Olanzapine and Clozapine on Conditioned Avoidance Responding The effects of repeated treatment with dl-govadine, olanzapine and clozapine in the conditioned avoidance responding (CAR) test were investigated as described in Example 9, using the following dosages:

dl-Govadine: 0.3 mg/kg (N=6) or 1.0 mg/kg (N=8)
Olanzapine: 0.5 mg/kg (N=6) or 1.0 mg/kg (N=8)
Clozapine: 2.5 mg/kg (N=6) or 5.0 mg/kg (N=10)

Figure 14:
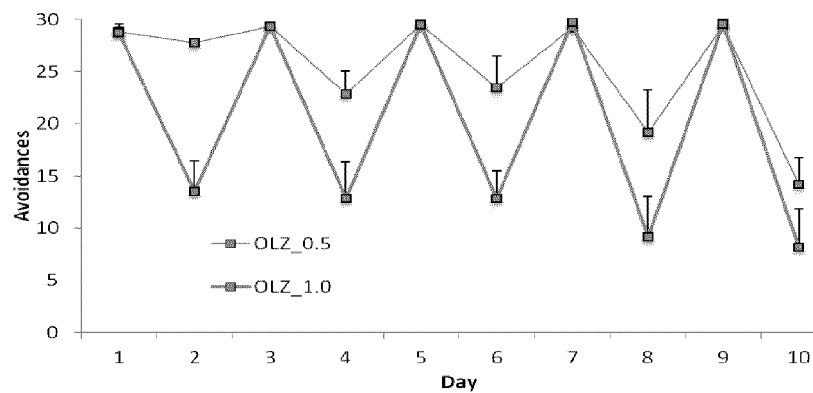
FIG. 14 presents the results of the analysis of conditioned avoidance responding in rats treated with (A) 0.5 or 1.0 mg/kg olanzapine, (B) 2.5 or 5.0 mg/kg clozapine, and (C) 0.3 or 1.0 mg/kg dl-govadine.
Figure 14:
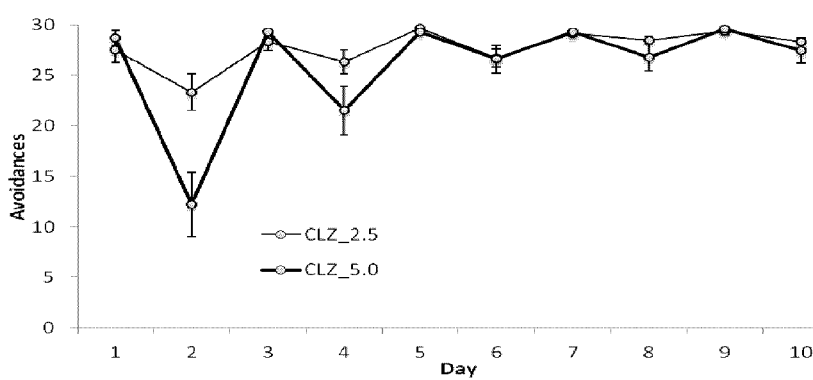
Figure 14:
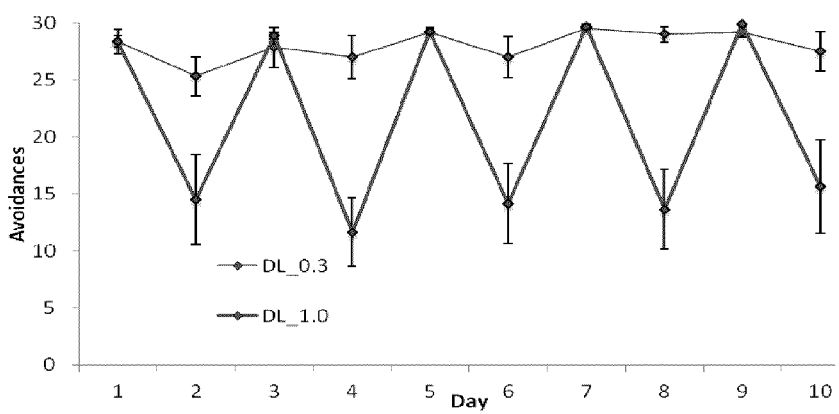

The results are shown in FIG. 14. A rapid development of tolerance was observed with clozapine at 5 mg/kg and sensitization with the low dose of olanzapine. Neither of these effects was observed with dl-govadine.

The disclosure of all patents, publications, including published patent applications, and database entries referenced in this specification are expressly incorporated by reference in their entirety to the same extent as if each such individual patent, publication, and database entry were expressly and individually indicated to be incorporated by reference.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

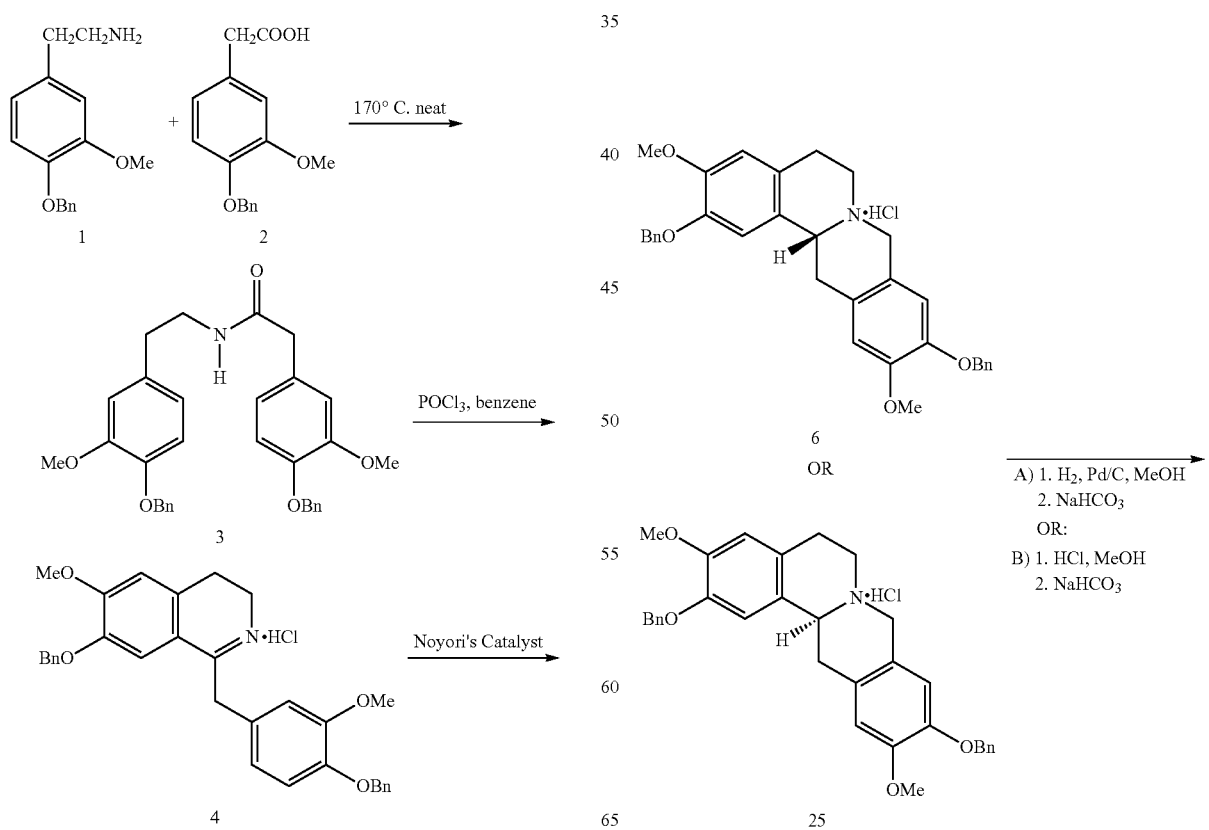

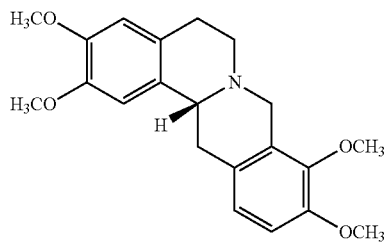
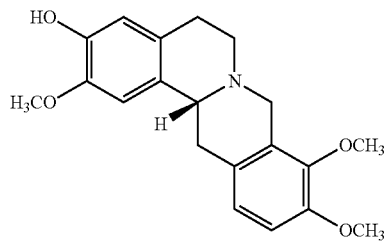
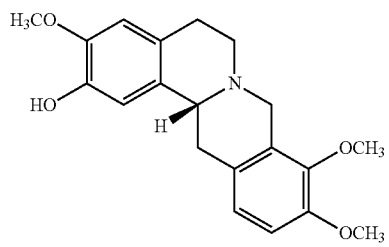
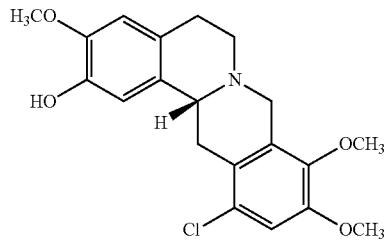
12. The method according to claim 1, wherein the compound is
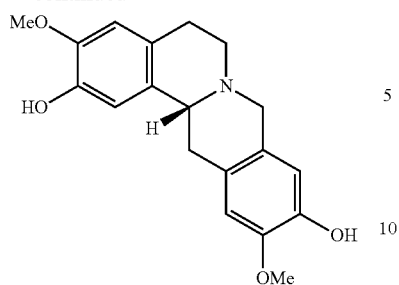
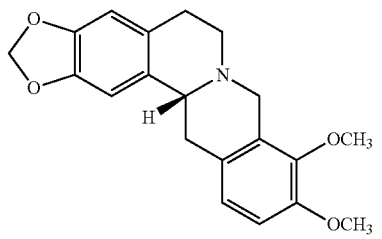
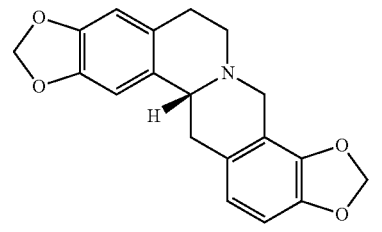

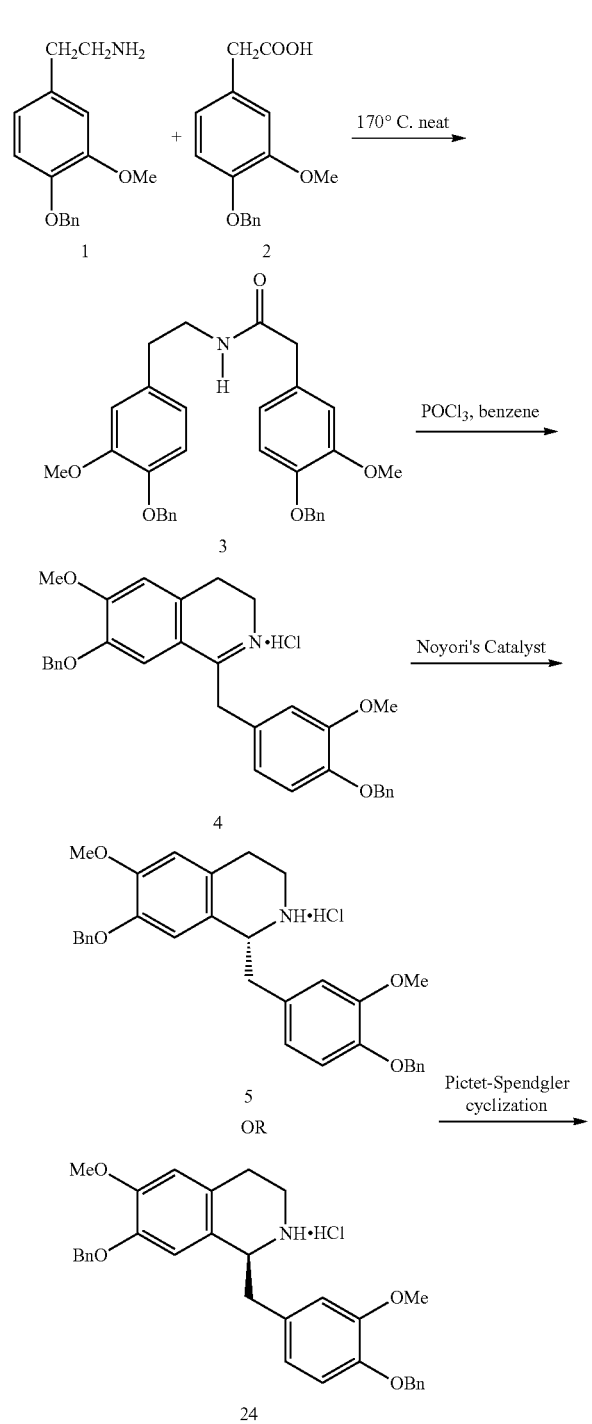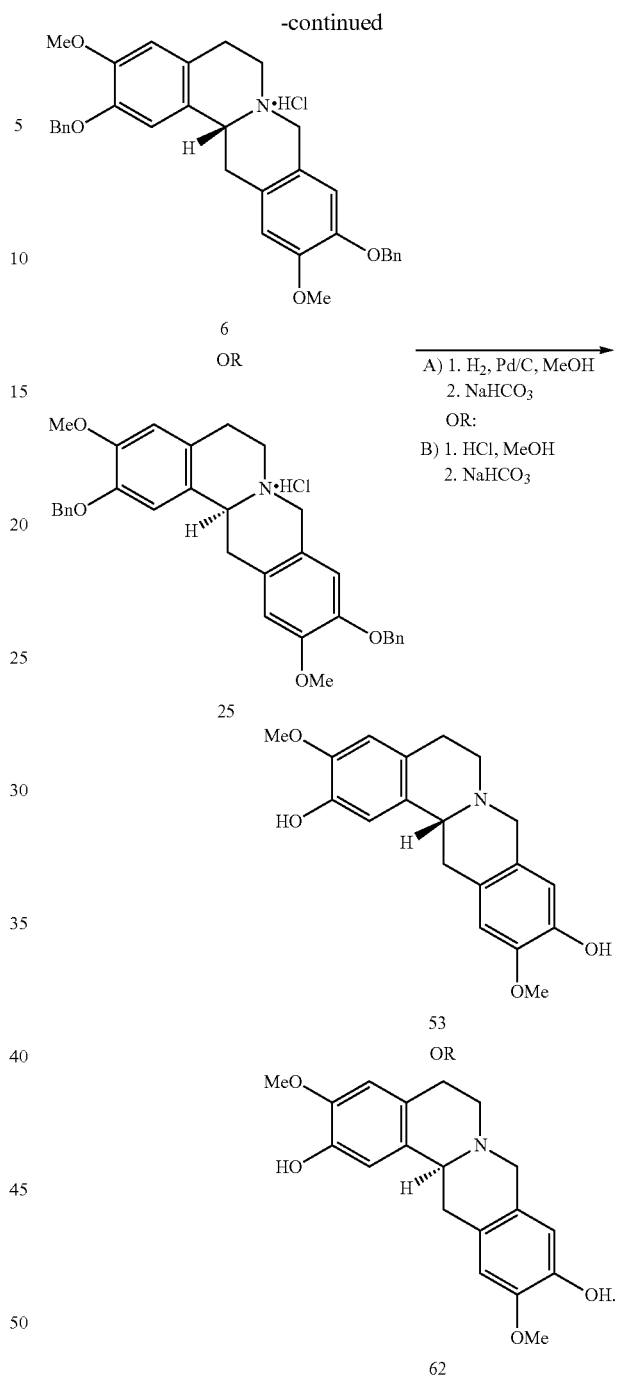

The invention claimed is:

1. A method of increasing dopamine release in the prefrontal cortex comprising administering to a subject in need thereof an effective amount of a compound of formula (I):

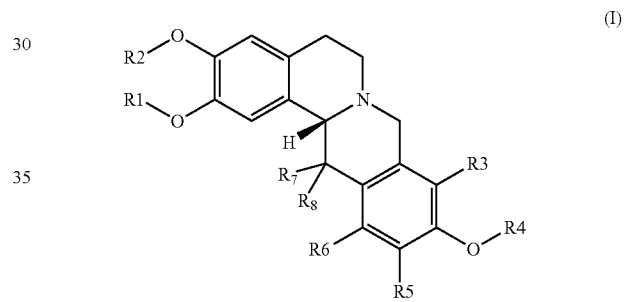

or a pharmaceutically acceptable salt, solvate or prodrug thereof, wherein:
R1 and R2 are independently H, alkyl, benzyl or —COR9; or R1 and R2 together form $(CH_2)_m$;
R4 is H, alkyl, benzyl, or —COR9;
R3 is H or OR10, wherein R10 is H, alkyl, benzyl or —COR9, or R10 taken together with R4 forms $(CH_2)_m$;
R5 is H or OR11, wherein R11 is H, alkyl, benzyl or —COR9, or R11 taken together with R4 forms $(CH_2)_m$;
R6 is H or halogen;
R9 is H or alkyl;
m is 1 or 2, and
wherein when R10 taken together with R4 forms $(CH_2)_m$, then R5 is H or OR11,
wherein R11 is H, alkyl, benzyl or —COR9, and
wherein when R11 taken together with R4 forms $(CH_2)_m$, then R3 is H or OR11,
wherein R11 is H, alkyl, benzyl or —COR9, and
wherein at least one of R3 and R5 is other than H.

2. The method according to claim 1, wherein the increasing dopamine release in the prefrontal cortex is effective in the treatment of cognitive impairment arising from hypodopamine function associated with the related conditions of schizophrenia and major depression.

3. The method according to claim 1, wherein the compound is administered in conjunction with one or more other therapeutic agents.

4. The method according to claim 1, wherein R3 is H and R5 is OR11.

5. The method according to claim 1, wherein R5 is H and R3 is OR10.

6. The method according to claim 1, wherein
R1 and R2 are independently H or alkyl, or R1 and R2 together form $(CH2)_m$;
R5 is H or O-alkyl;
R6 is H or halogen;
R7 is H;
R8 is H or alkyl; and
either R3 is H or O-alkyl, and R4 is H, or
R3 is OR10 and R10 and R4 together form $(CH2)_m$.

7. The method according to claim 1, wherein
R1 and R2 are independently H or alkyl, or R1 and R2 together form $(CH2)_m$;
R3 is H or O-alkyl;
R6 is H or halogen;
R7 is H;
R8 is H or alkyl; and
either R4 is H, and R5 is H or O-alkyl, or
R5 is OR11 and R11 and R4 together form $(CH2)_m$.

8. The method according to claim 1, wherein
R1 and R2 are independently H or alkyl;
R3 and R5 are independently H or O-alkyl;
R4 and R7 are H;
R6 is H or halogen; and
R8 is H or alkyl.

9. The method according to claim 1, wherein
R1 and R2 are independently H or alkyl;
R3 and R5 are independently H or O-alkyl;
R4, R6 and R7 are H; and
R8 is H or alkyl.

10. The method according to claim 1, wherein each alkyl is a $C_1$-$C_4$ alkyl.

11. The method according to claim 1 wherein administration involves an effective amount of enantiomerically pure d-govadine derived from a process comprising the steps:

(a) performing a coupling reaction between compounds (XVI) and (XVII) to provide amide (XVIII);

(b) performing a Bischler-Napieralski reaction on the amide (XVIII) to provide dihydroisoquinoline intermediate (XIX);

(c) reducing the dihydroisoquinoline intermediate (XIX) with a chiral catalyst to provide compound (XIV) or (XV);

(d) performing a Mannich-type cyclization on compound (XIV) or (XV) to obtain d- or l-govadine, wherein the synthesis route is as follows:

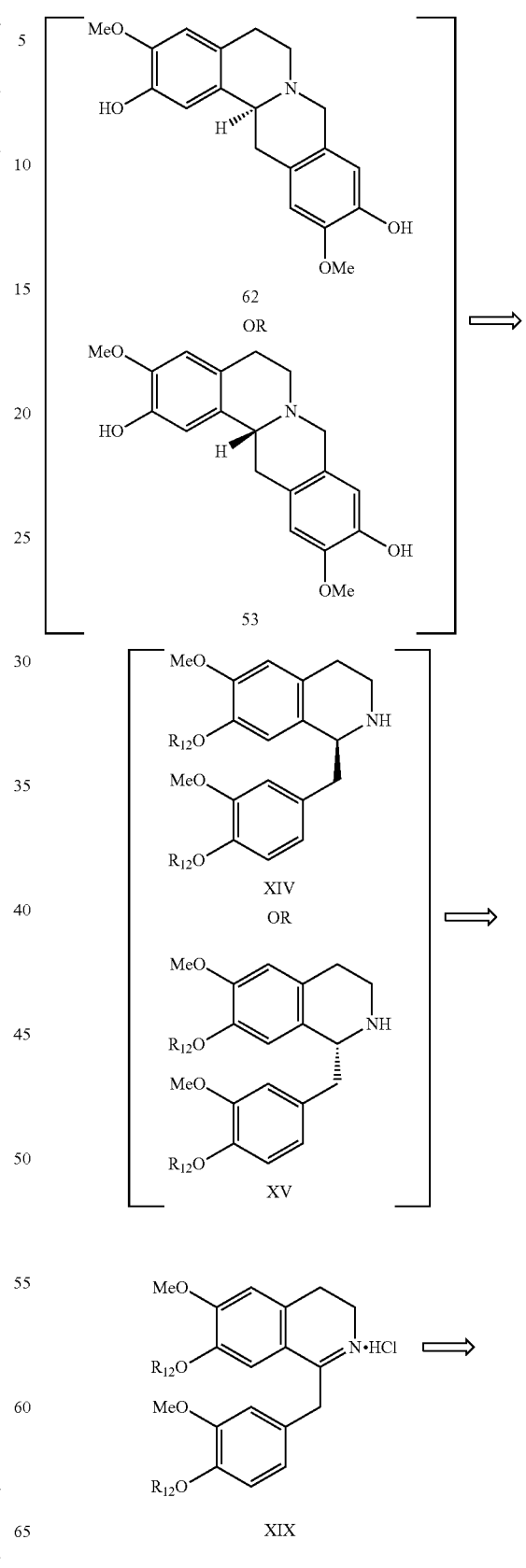

75
-continued

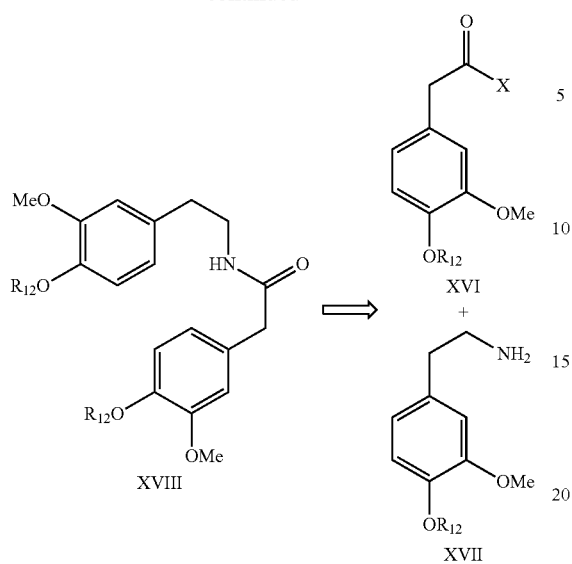

XVIII

76
-continued

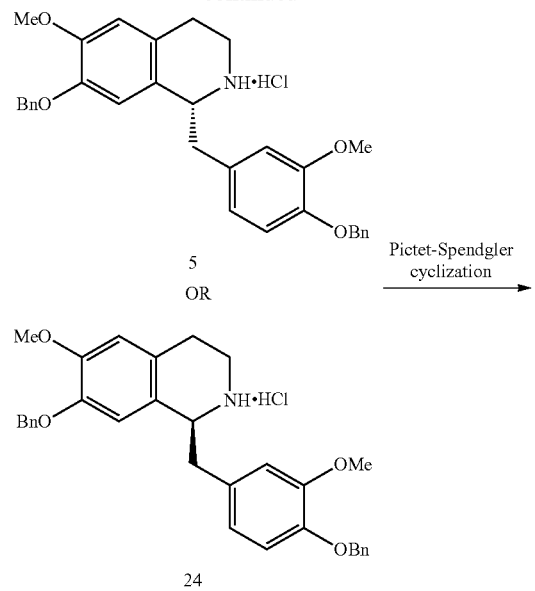

5
OR

24

Pictet-Spendgler cyclization → and wherein X is Cl or OH, and R12 is a protecting group
or wherein X is OH, and the coupling reaction is a thermal coupling reaction in the presence or absence of solvent; wherein the Bischler-Napieralski reaction uses POCl$_3$; wherein the chiral catalyst is Noyori's catalyst; wherein the Mannich-type cyclization is a Pictet-Spengler cyclization and wherein the synthesis route is as follows: